(12) United States Patent
Ouckama et al.

(10) Patent No.: US 12,159,488 B2
(45) Date of Patent: Dec. 3, 2024

(54) SYSTEM, METHOD AND COMPUTER-READABLE MEDIUM FOR MEASURING ATHLETIC PERFORMANCE

(71) Applicants: BAUER HOCKEY LLC., Exeter, NH (US); BAUER HOCKEY LTD., Blainville (CA)

(72) Inventors: Ryan Ouckama, Kingston (CA); Carolyn Steele, Portsmouth, NH (US)

(73) Assignee: BAUER HOCKEY LLC, Exeter, NH (US)

(*) Notice: Subject to any disclaimer, the term of this patent is extended or adjusted under 35 U.S.C. 154(b) by 367 days.

(21) Appl. No.: 17/594,226

(22) PCT Filed: Apr. 9, 2020

(86) PCT No.: PCT/US2020/027470
§ 371 (c)(1),
(2) Date: Oct. 7, 2021

(87) PCT Pub. No.: WO2020/210492
PCT Pub. Date: Oct. 15, 2020

(65) Prior Publication Data
US 2022/0180665 A1    Jun. 9, 2022

Related U.S. Application Data

(60) Provisional application No. 62/832,593, filed on Apr. 11, 2019.

(51) Int. Cl.
*G09B 19/00* (2006.01)
*A61B 5/00* (2006.01)
(Continued)

(52) U.S. Cl.
CPC .......... *G06V 40/23* (2022.01); *A61B 5/02438* (2013.01); *A61B 5/1113* (2013.01);
(Continued)

(58) Field of Classification Search
None
See application file for complete search history.

(56) References Cited

U.S. PATENT DOCUMENTS

| 10,928,412 B2 | 2/2021 | Bundock |
| 2008/0191864 A1* | 8/2008 | Wolfson ............... G06F 3/04815 434/323 |

(Continued)

FOREIGN PATENT DOCUMENTS

| CA | 3088611 | 2/2021 |

OTHER PUBLICATIONS

International Search Report and Written Opinion issued by the International Searching Authority in connection with PCT application No. PCT/US2020/027470 on Jul. 28, 2020, 13 pages.
(Continued)

*Primary Examiner* — Sunit Pandya

(57) ABSTRACT

A non-transitory computer-readable storage medium storing computer-readable instructions which, when executed by a processor of a computing device, cause the computing device to carry out a method. The method comprises obtaining sensor data indicative of a parameter sensed by a sensor associated with an article of sports equipment; obtaining position data indicative of a spatial position of the sensor or of the article of sports equipment; jointly processing the sensor data and the position data to derive a hybrid metric; and outputting a signal conveying the hybrid metric on a network or storing the hybrid metric in a computer-readable memory. The sensor data and the position data may be time-aligned to a common time reference, so that the jointly processing is carried out on the time-aligned sensor data and position data. The hybrid metric measures properties that are not derivable from the sensor data alone or the position data alone.

60 Claims, 56 Drawing Sheets

(51) Int. Cl.
*A61B 5/024* (2006.01)
*A61B 5/11* (2006.01)
*G06V 20/40* (2022.01)
*G06V 40/20* (2022.01)

(52) U.S. Cl.
CPC .......... *A61B 5/1128* (2013.01); *A61B 5/6895* (2013.01); *G06V 20/42* (2022.01); *A61B 2503/10* (2013.01); *A61B 2562/0219* (2013.01); *A61B 2562/08* (2013.01)

(56) References Cited

U.S. PATENT DOCUMENTS

| | | |
|---|---|---|
| 2014/0228649 A1 | 8/2014 | Rayner et al. |
| 2016/0038788 A1* | 2/2016 | McMillan ............ A43B 5/0401 73/488 |
| 2016/0059075 A1* | 3/2016 | Molyneux .......... A63B 24/0021 700/91 |
| 2016/0098941 A1* | 4/2016 | Kerluke ................ G06F 3/017 700/91 |
| 2017/0004358 A1 | 1/2017 | Bose et al. |
| 2019/0046857 A1* | 2/2019 | Sellers, III ........ A63B 69/0024 |
| 2019/0091541 A1 | 3/2019 | Schulte et al. |
| 2020/0306602 A1* | 10/2020 | Ducharme ......... G09B 19/0038 |
| 2020/0384329 A1 | 12/2020 | Bartels |
| 2020/0398111 A1 | 12/2020 | Near et al. |
| 2020/0398134 A1 | 12/2020 | Bartels |
| 2021/0093916 A1* | 4/2021 | Lowe ....................... A63C 1/30 |

OTHER PUBLICATIONS

Eline van der Kruk & Marco M. Reijne (2018) Accuracy of human motion capture systems for sport applications; state-of-the-art review, European Journal of Sport Science, 18:6, 806-819, DOI: 10.1080/17461391.2018.1463397, Published May 9, 2018, 15 pages.

Ashley Hannon (2010) Comparisons of calibre and stick shaft stiffness, published May 2010, 134 pages.

Xcitex MidasDA brochure, Record Sensor Data with Video from any Camera, 2 pages.

Terrell R. Bennett, Nicholas Gans, and Roozbeh Jafari (2015) Multi-Sensor Data-Driven Synchronizarion Using Wearable Sensors, published Sep. 11, 2015, 4 pages.

HockeyTutorial.com, Track your hockey on Apple Watch!, published Apr. 3, 2019, 2 pages.

Wei-Lwun Lu (2007) Tracking and Recognizing Actions of Multiple Hockey Players using the Boosted Particle Filter, publishes Apr. 2007, 86 pages.

* cited by examiner

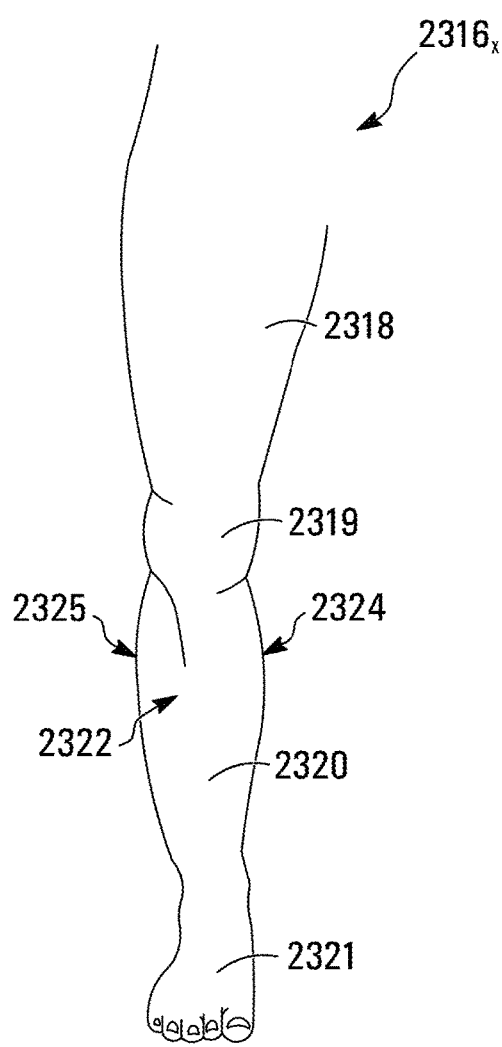
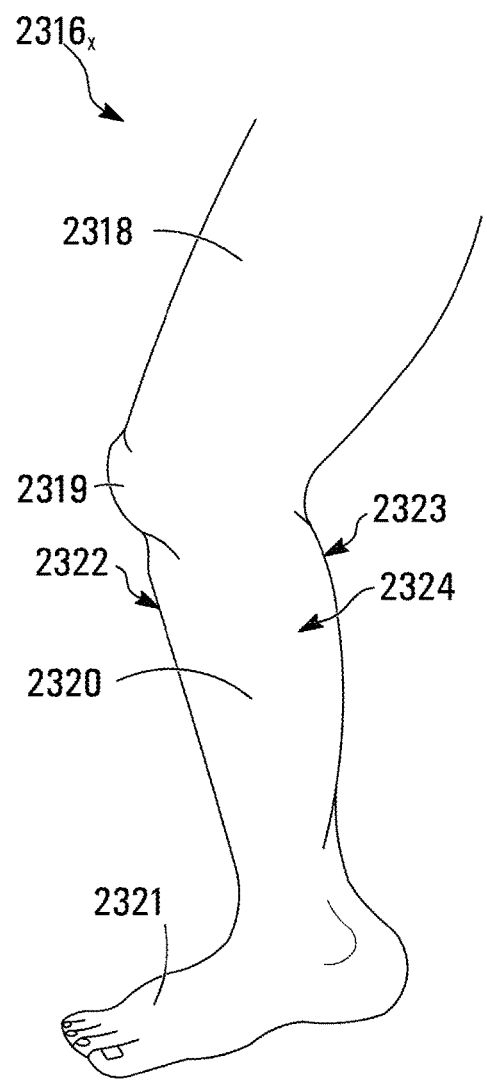
FIG. 13F    FIG. 13G

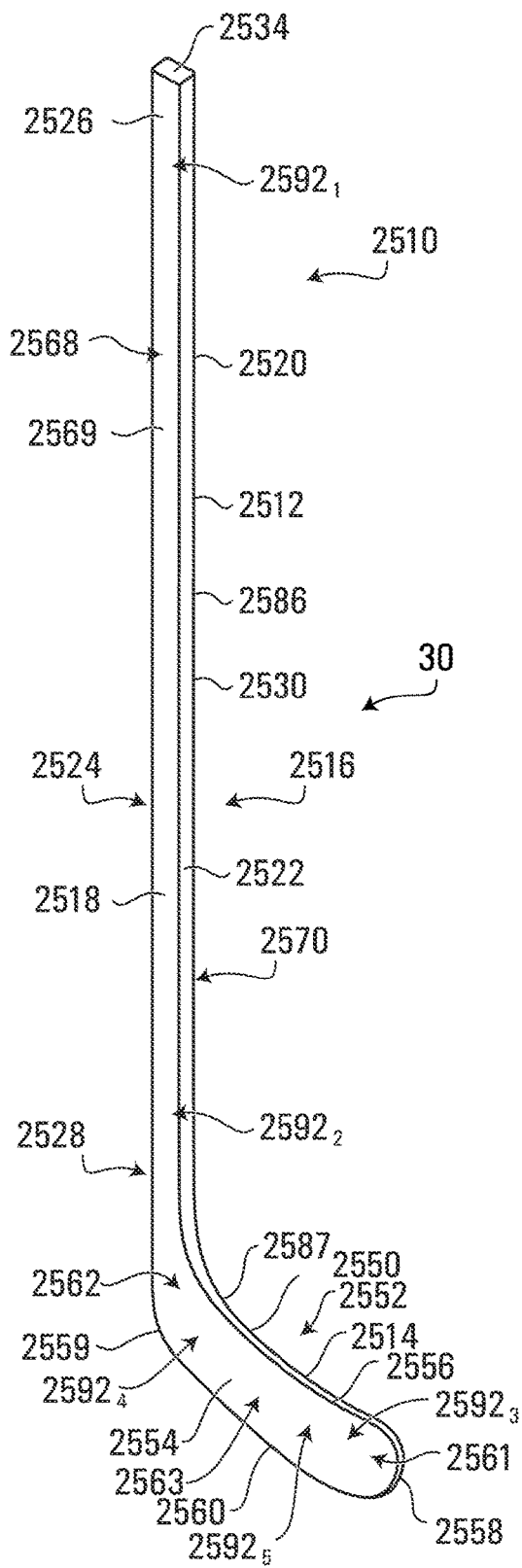
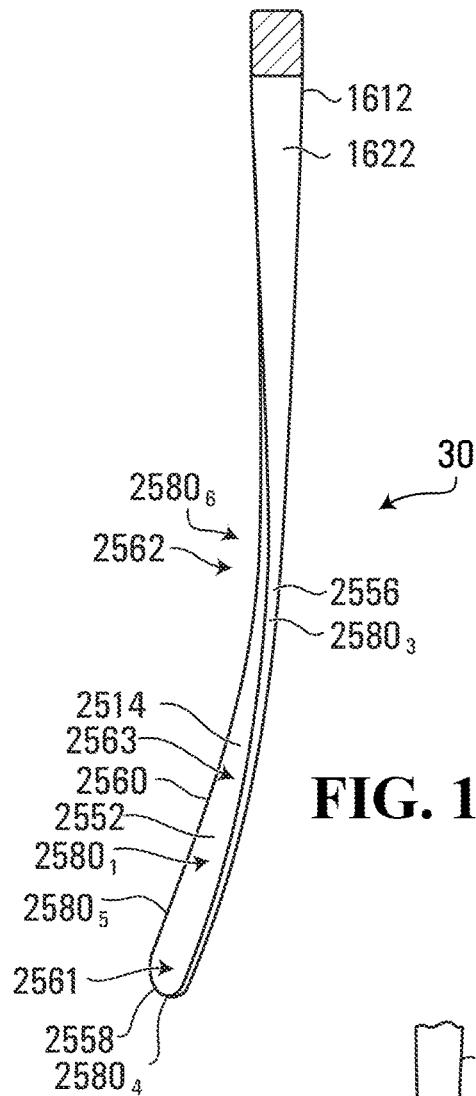
FIG. 15D
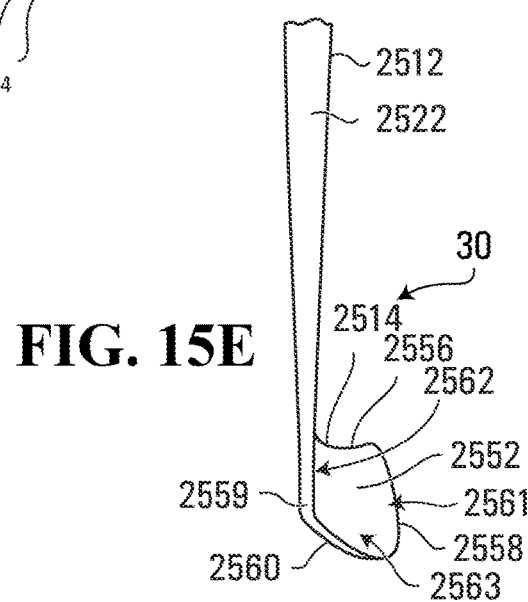
FIG. 15E
FIG. 15C

2700

Prompting user for ice surface size
2710

Prompting user to confirm the placement of the beacons
2720

Processing received signals and determining positions of the players or articles of equipment containing tags and/or sensors
2730

FIG. 27

SYSTEM, METHOD AND COMPUTER-READABLE MEDIUM FOR MEASURING ATHLETIC PERFORMANCE

CROSS-REFERENCE TO RELATED APPLICATION

The present application claims the benefit of U.S. Provisional Application Ser. No. 62/832,593, filed on Apr. 11, 2019, which is hereby incorporated by reference herein.

FIELD

The present disclosure relates to a system and method for improving athletic performance, in particular through the processing of data of multiple types.

BACKGROUND

Increasingly, technology is used by athletes to improve their performance. This includes the use of video cameras, which can be used to record athlete responses and techniques and used for training purposes. Also, apps can be installed to measure heart rate and other biometric features. Each of these elements may provide some benefit in terms of feedback and subsequent performance improvement. However, such technologies fail to reveal certain key underlying aspects of an athlete's performance that occur during only brief periods or in certain specific game scenarios. As such, the industry would welcome a more sophisticated, data-driven approach for assisting athletes in monitoring and improving their performance.

SUMMARY

In some embodiments, position data is captured by a position determining system and sensor data captured by a player's equipment are processed to extract performance metrics about the player. Such performance metrics can be useful for training and/or competitive purposes. Certain embodiments are particularly adapted to non-professional ice hockey environments.

Accordingly, a first broad aspect of the disclosure seeks to provide a computer-implemented method, which comprises obtaining sensor data indicative of a parameter sensed by a sensor associated with an article of sports equipment; obtaining position data indicative of a spatial position of the sensor or of the article of sports equipment; jointly processing the sensor data and the position data to derive a hybrid metric; and outputting a signal conveying the hybrid metric on a network or storing the hybrid metric in a computer-readable memory. The sensor data and the position data may be time-aligned to a common time reference, so that the jointly processing is carried out on the time-aligned sensor data and position data. A hybrid metric may be viewed as being a metric that is not derivable from the actual sensor data alone or the position data alone. The position of the sensor, article of equipment or player emitting the sensor data is required together with the sensor data (for one or more sensors) to generate the hybrid metric. This position may be obtained by triangulating the signal that contains the sensor data, or by using an independent position determining system.

Also provided are a computer-readable medium and a computing device configured for implementing the aforesaid method.

These and other aspects and features of the present invention will now become apparent to those of ordinary skill in the art upon review of the following description of specific embodiments of the invention in conjunction with the accompanying drawings.

BRIEF DESCRIPTION OF THE DRAWINGS

In the drawings:

FIG. 27 is a flowchart illustrating steps of a position determining program run by the computing device, in accordance with a non-limiting example;

It is to be expressly understood that the description and drawings are only for the purpose of illustration of certain embodiments of the invention and are an aid for understanding. They are not intended to be a definition of the limits of the invention.

DETAILED DESCRIPTION

Figure 1:
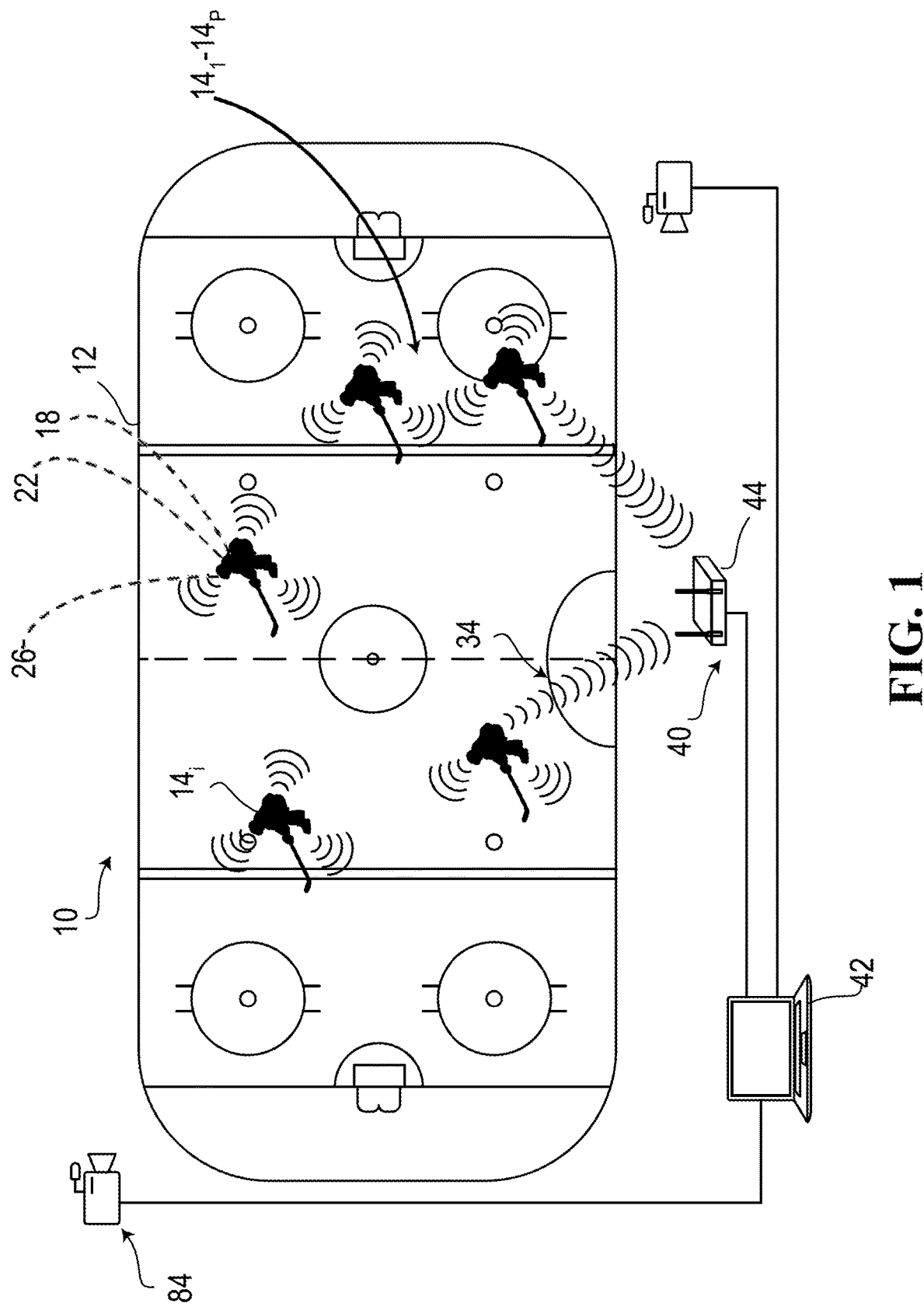
FIG. 1 illustrates an ice hockey environment, in accordance with a non-limiting embodiment.

FIG. 1 shows an ice hockey environment 10 in which there is provided an ice surface 12 on which a plurality of players $14_1$-$14_P$ play ice hockey. Each individual player $14_i$ has equipment 30 that comprises one or more sensor modules 18. A given sensor module 18 may include one or more sensors 22. Examples of sensors 22 that could be used include accelerometers, gyroscopes, magnetometers, inertial measurement units, pressure sensors, strain gauges, body motion sensors, heart rate monitors and thermometers, to name a few non-limiting possibilities. A given sensor module 18 collects data sensed by the sensor 22 and transmits it wirelessly to a receiver system 40 or stores it for later extraction by the receiver system 40.

In the present environment 10, the sensor modules 18 are embedded in, or attached to, equipment 30 used by the players $14_1$-$14_P$. The term "equipment" (see, for example, FIGS. 6A to 17B, among others) is meant to encompass a broad range of articles, including (i) articles used primarily to protect (e.g., helmet, gloves, protective pants, leg pads, shoulder pads), (ii) articles with a generally utilitarian function (e.g., skates, stick) and (iii) articles that are primarily worn as apparel (e.g., jersey, undergarment, socks). The sensor modules 18 may be embedded in the equipment 30 or attached to the inside or to the outside of the equipment 30.

Different player roles may be associated with different player equipment 30 and therefore different sensors 22. Specifically, some sensors are more suitable for a goalie and others for a non-goalie. For example, in the sport of hockey, some sensors 22 may be particularly suited to the skates, helmet, stick, gloves, jersey, shorts, leg pads and shoulder pads of a non-goalie. Similarly, other sensors 22 may be particularly suited to the skates, helmet, facemask, stick/paddle, gloves/blocker, jersey, shorts, leg pads and shoulder pads of a goalie. In other examples, one or more sensors 22 may be embedded into the base layer of an undergarment.

Figure 28:
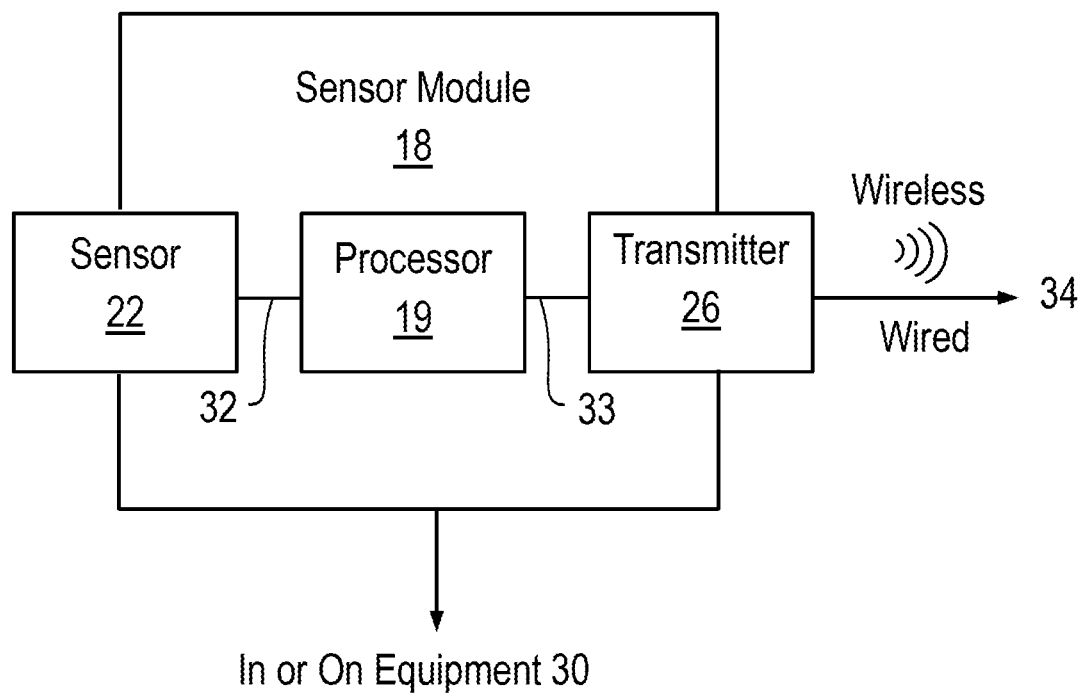
FIG. 28 is a block diagram of a sensor module, in accordance with a non-limiting embodiment.

With further reference to FIG. 28, in addition to including a sensor 22, a given sensor module 18 may also include a processing entity (e.g., a microprocessor 19) and a transmitter 26 (e.g., a wireless/radio transmitter). In some embodiments, the processing entity of the sensor module 18 is configured to receive readings of a physical parameter via the sensor 22 over time (this is referred to as "sensor-captured data", "raw sensor data" or sensor data 32), format the sensor data 32 into a digital signal 33 having a suitable transmission format, to which a time stamp may be added, and transform the digital signal 33 into a wireless signal 34 that is output over-the-air via the transmitter 26. The transmitter 26 may use one of any number of technologies to transmit the wireless signal 34, including but not limited to WiFi, Bluetooth, UWB, NFC and other radio frequency or free-space-optical technologies.

Figure 5:
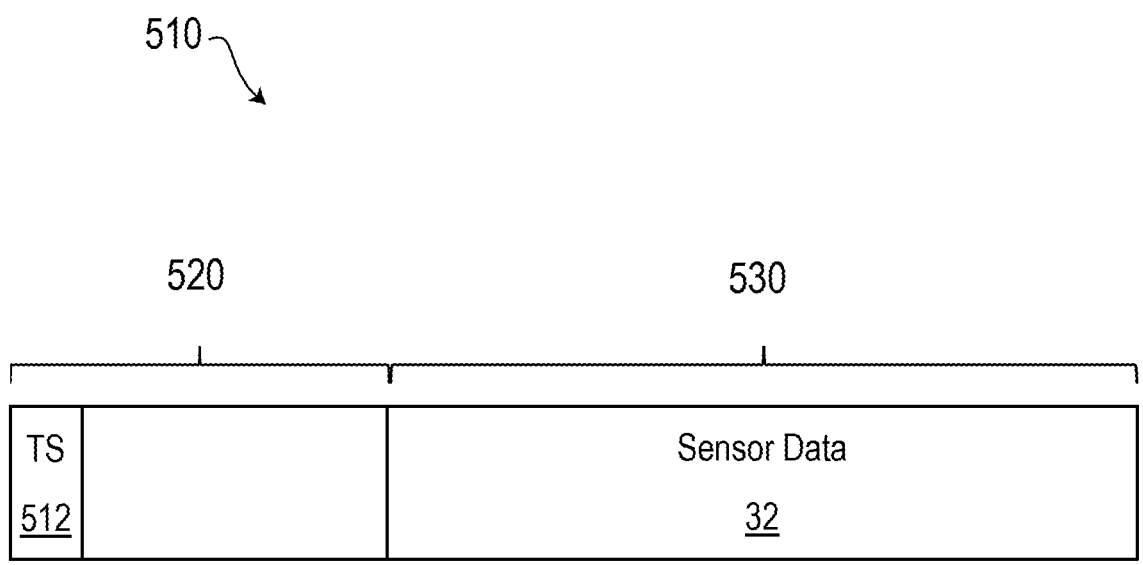
FIG. 5 shows a format of a packet that may carry sensor data.
Figure 6A:
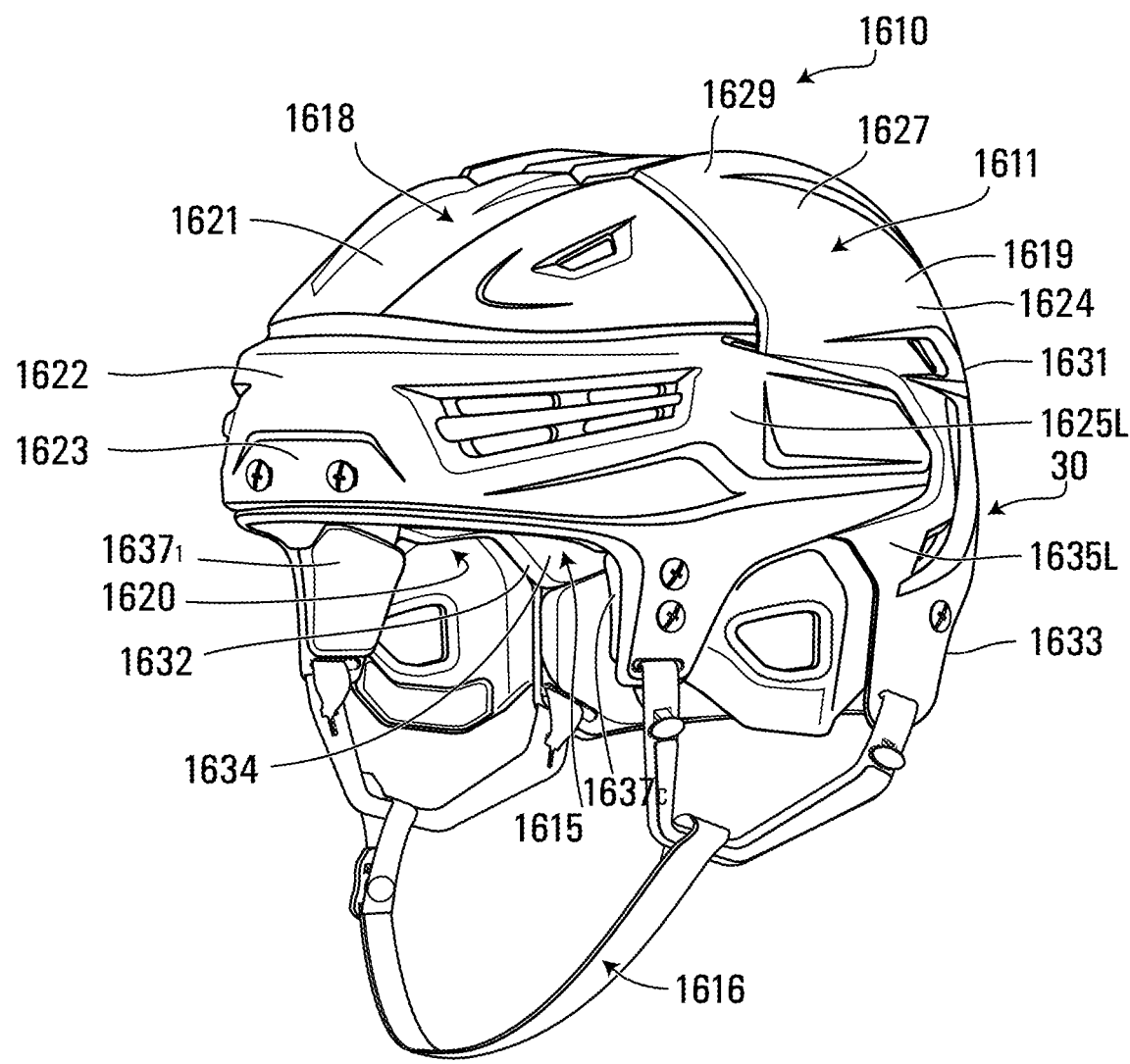
FIGS. 6A to 17B show various articles of sports equipment to which various embodiments of the present invention may be applied.
Figure 6B:
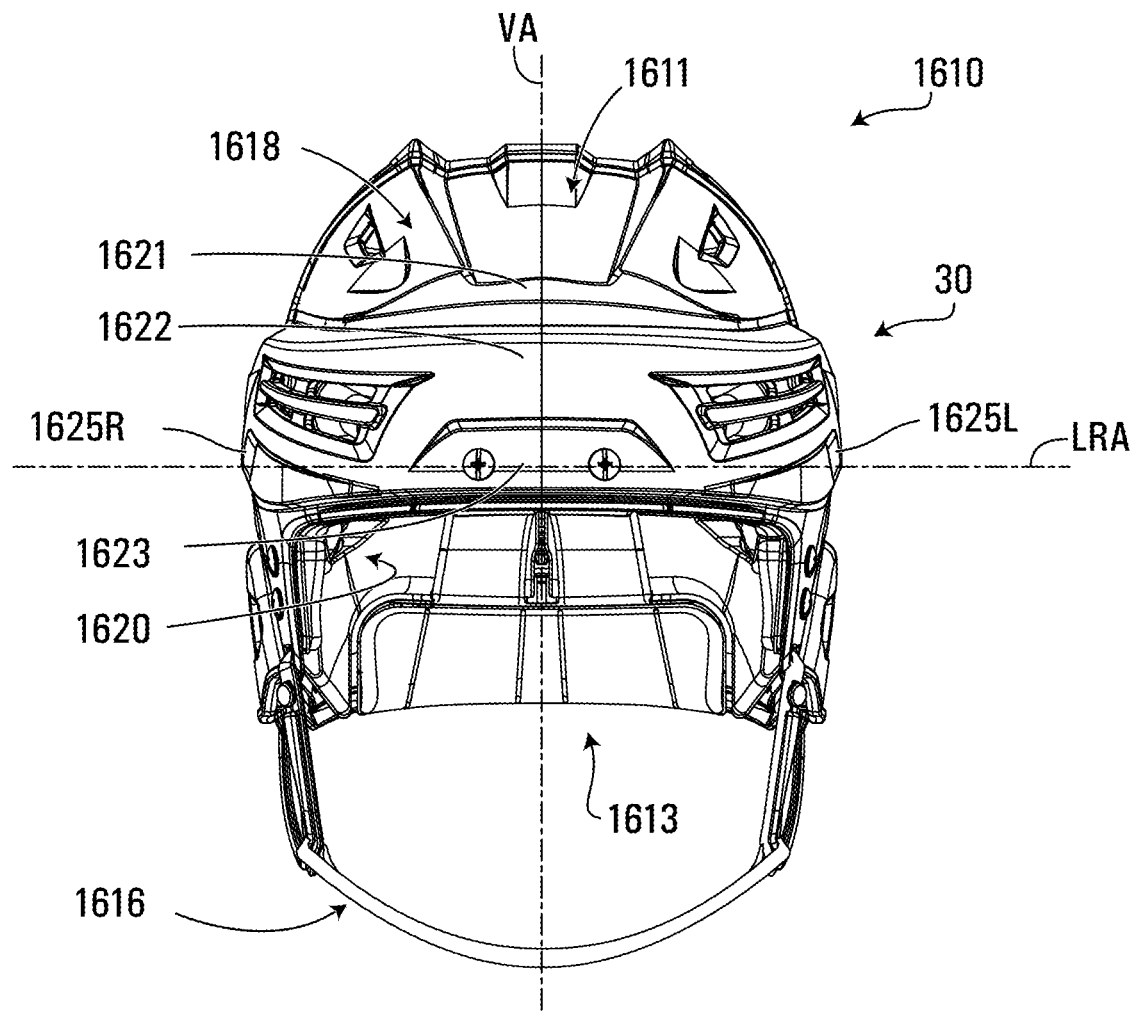
Figure 6C:
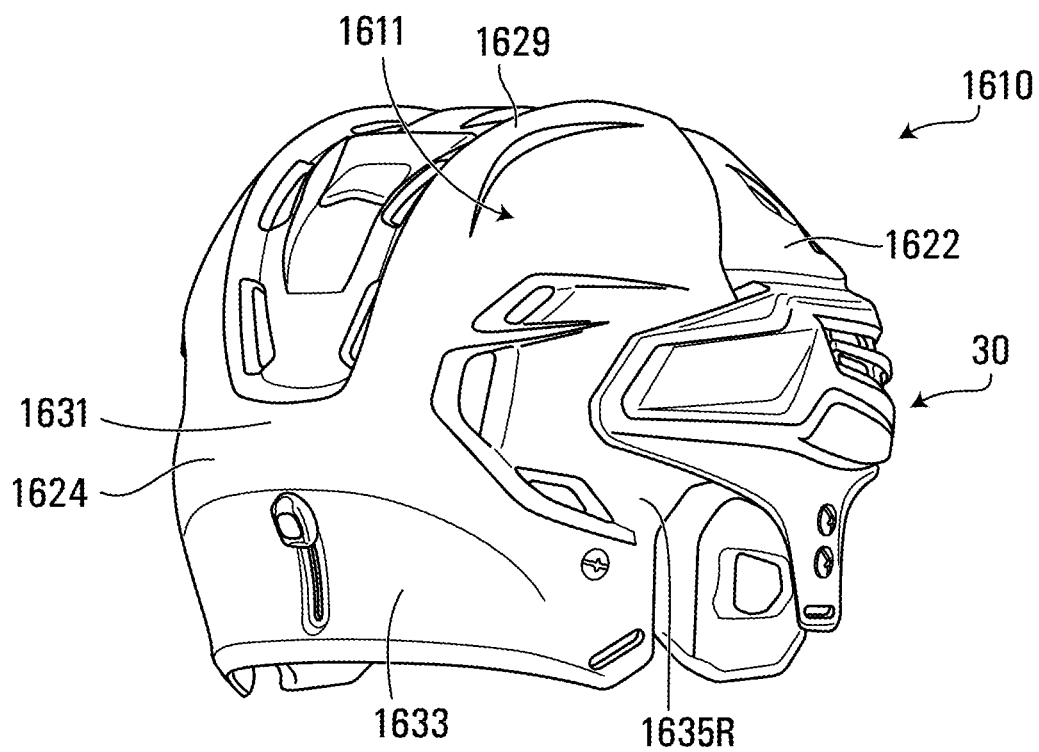
Figure 6D:
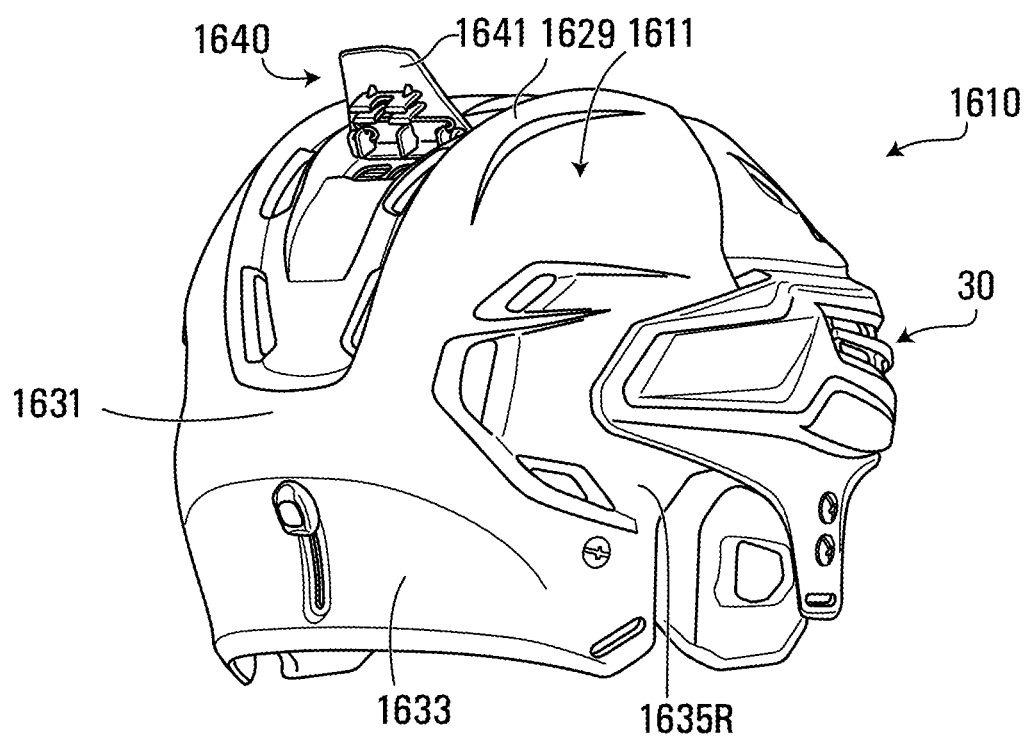
Figure 6E:
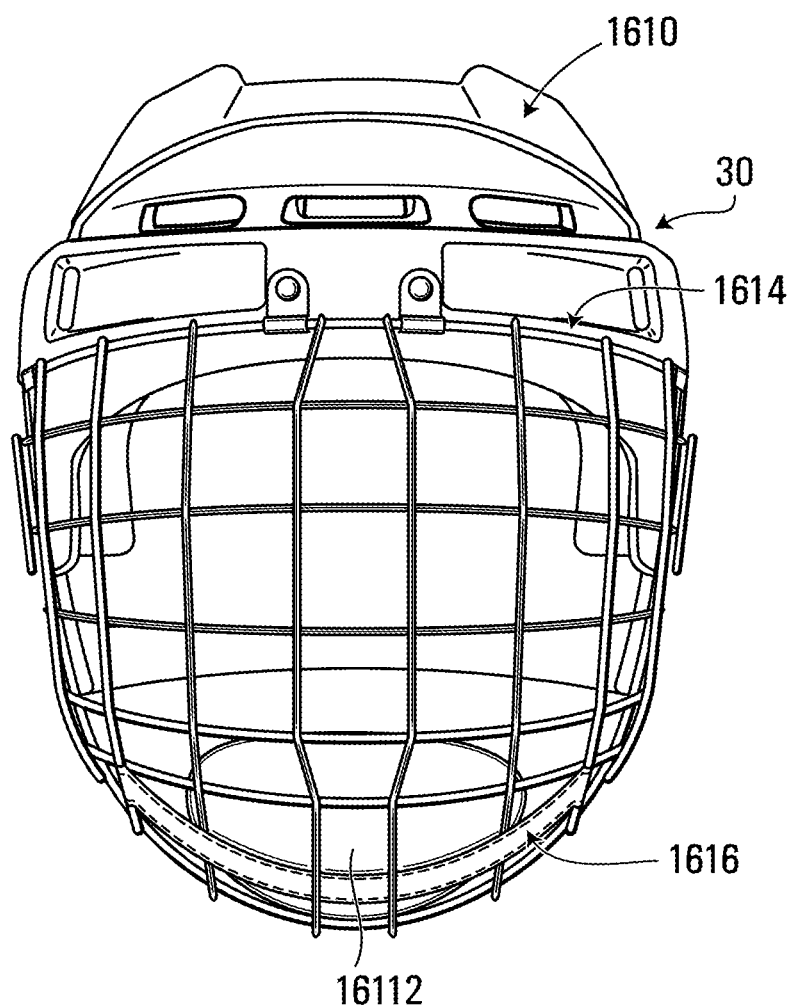
Figure 6F:
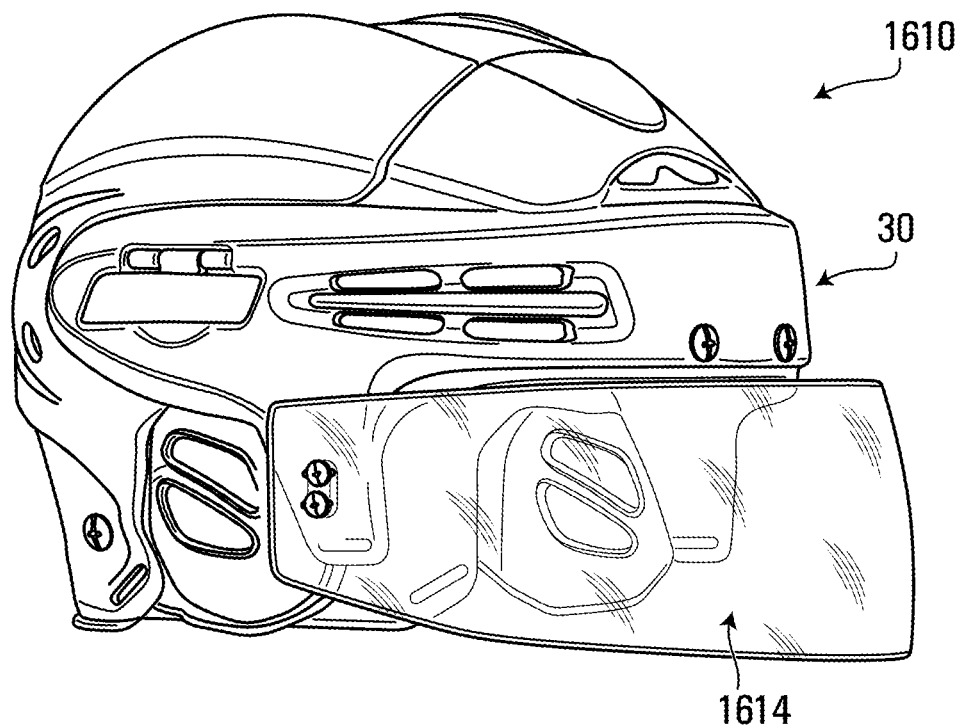
Figure 6G:
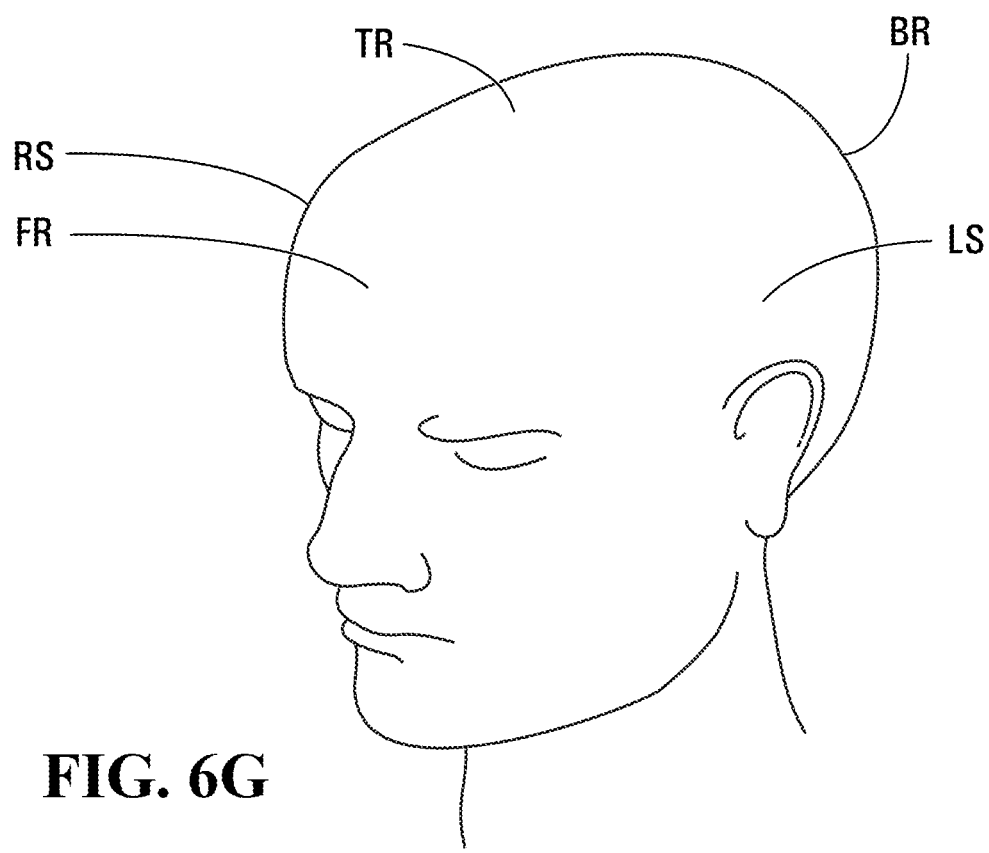
Figure 6H:
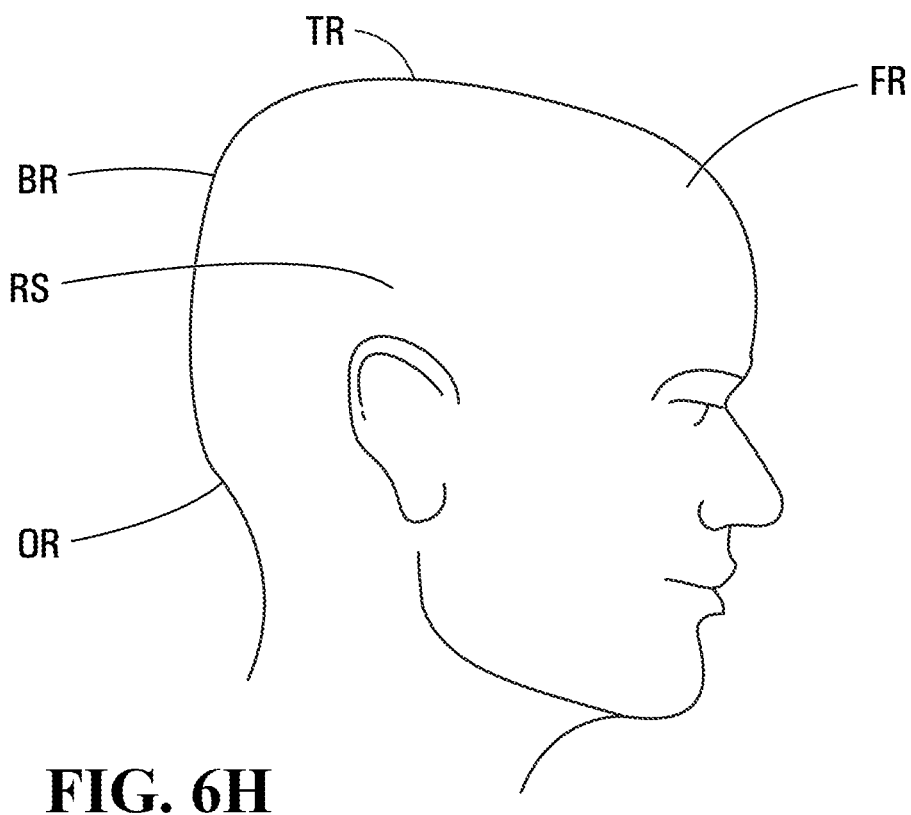
Figure 6I:
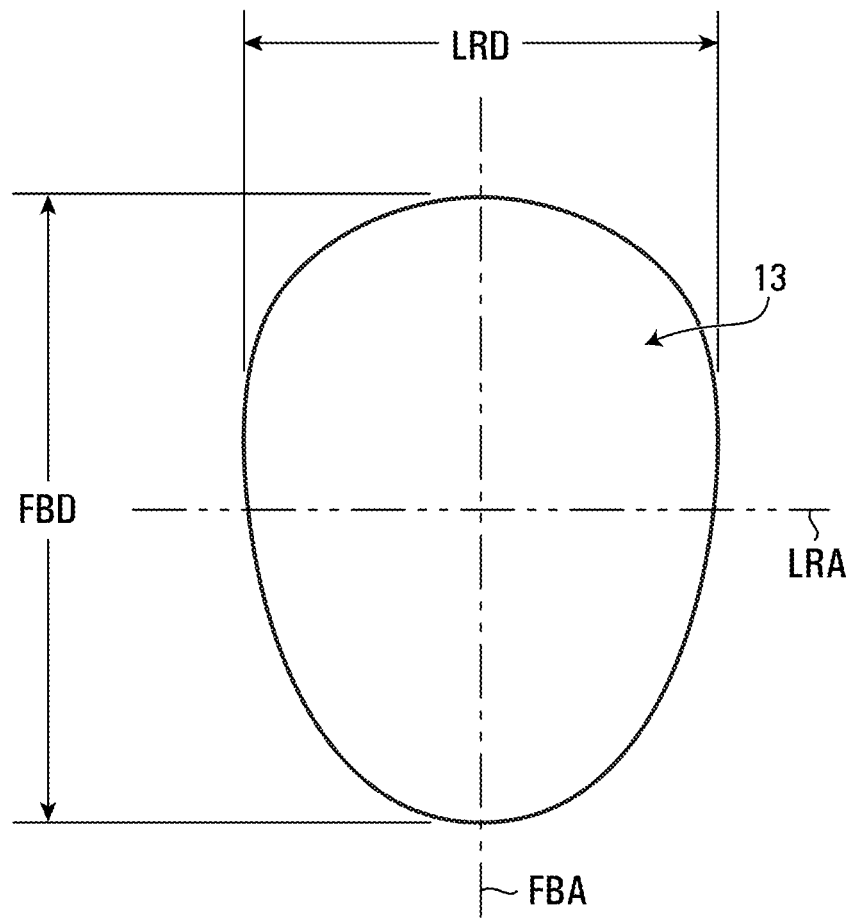

With reference to FIG. 5, the digital signal 33 that conveys the sensor data 32 may be in a suitable format such as a stream of packets 510 each with a header 520 and a payload 530. The header 510 may include a time stamp 512 (corresponding to, e.g., a time at which the sensor 22 issued the sensor data 32 or a time when the processor issues the digital signal containing the sensor data 32), as well as other information, which may include sensor type, equipment type, format of payload, payload length (or packet length), player ID and/or other information. For its part, the payload 520 includes the sensor data 32 in the format that may be specified in the header 510. Other configurations of the digital signal are possible. Packets such as the packet 510 may be issued at a frequency that is determined by the sensor 22, by the processing entity or set by an external user (including the player himself/herself).

In other embodiments, the processing entity of a given sensor module 18 is configured to receive the sensor data 32 from the sensor 22 and store it as a file in a memory (while the equipment 30 comprising the sensor 22 is still worn by the player $14_j$), for eventual transfer out of the memory during a subsequent operation offline.

Also provided in the environment 10 of FIG. 1 is a receiver system 40, which is compatible with the sensor modules 18. The receiver system 40 receives the wireless signals 34 transmitted by the various sensor modules 18 in/on the equipment 30 and extracts the sensor data 32 they contain so that such data can be processed by a computing device 42. In an embodiment, the receiver system 40 comprises one or more wireless receivers 44 that are compatible with the transmitters 26 of the sensor modules 18. In some cases, a single receiver 44 may be capable of handling wireless transmissions from multiple sensor modules 18 associated with different sensor types. In other cases, multiple receivers 44 may be provided, each such receiver 44 being dedicated to a particular sensor type and capable of handling wireless transmissions only from the sensor modules 18 associated with the particular sensor type. Still other configurations of the receiver system 40 are possible, including redundant receivers 44 distributed around the ice hockey rink and receiver systems 40 that allow offline transfers of files containing data (such as the raw sensor data 32) stored by the sensor modules 18.

Figure 18:
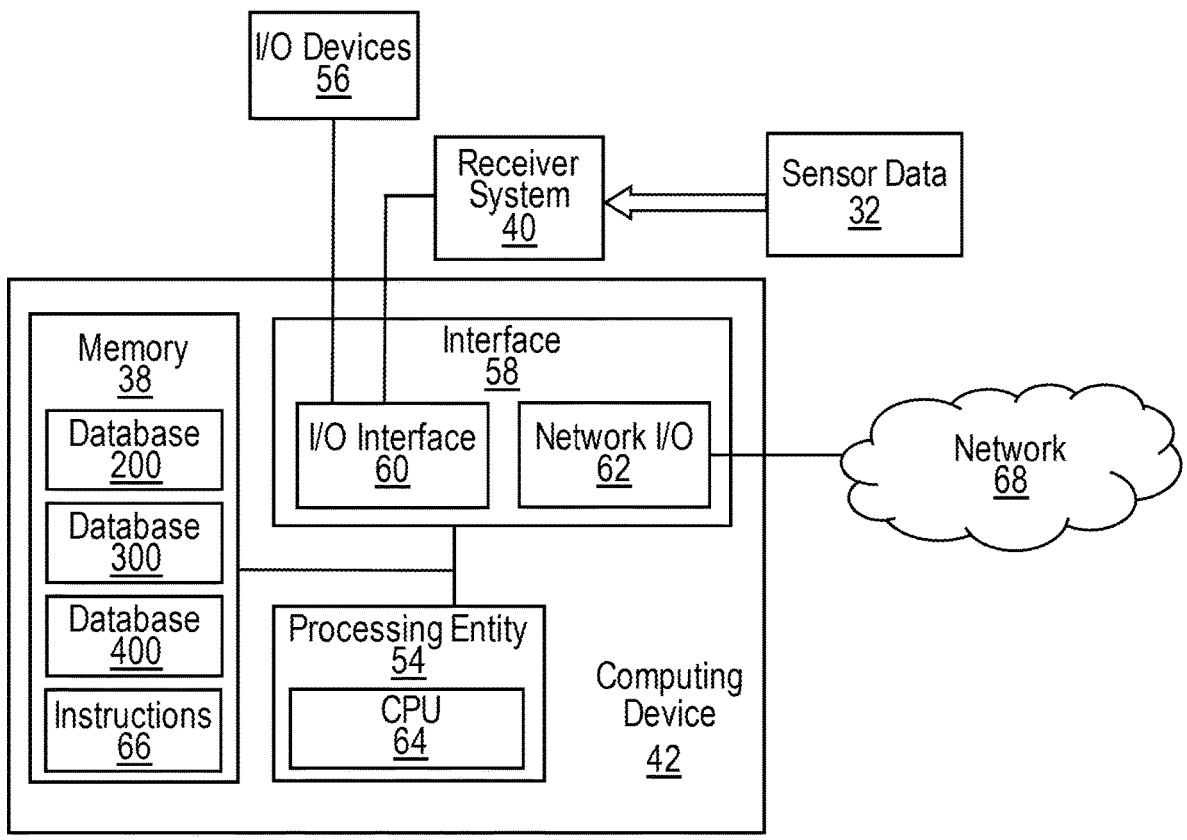
FIG. 18 is a block diagram of a computing device, in accordance with a non-limiting embodiment.

Also provided in the environment 10 of FIG. 1 is a computing device 42. The computing device 42 may be embodied as a laptop, desktop, smartphone or tablet. As shown in FIG. 18, the computing device 42 comprises a processing entity 54 (such as a microcontroller), a memory 38 and an interface 58. The interface 58 may have an input/output (I/O) interface portion 60 that connects to the receiver system 40, and is configured to receive the raw sensor data 32 from the receiver system 40, whether this be in real-time or offline. The I/O interface 60 may also connect to one or more input and/or output devices 56, such as a screen, keyboard or loudspeaker. In addition, the interface may have a network interface 62 portion that connects to a network 68, for example a public network such as the internet or a private intranet, for example. The processing entity 54 may comprise one or more CPUs 64. The memory 38 comprises, inter alia, computer-readable program code (instructions) 66 that is read and executed by the processing entity 54. In doing so, the processing entity 54 carries out a plurality of processes, some of which will be described herein below.

As such, use of the sensor modules 18 and the receiver system 40 allows the sensor data 32 to reach the computing device 42 where it can be stored in the memory 38 and processed in accordance with a variety of processes.

In another embodiment, the sensor modules 18 may be connected directly to the computing device 42 (e.g., by a wire, or by a contactless mechanism) to allow downloading of the sensor data 32, which had been stored on the sensor modules 18, into the memory 38 of the computing device 42.

In another embodiment, an intermediate transceiver may be located between the sensor modules 18 and the receiver system 40. For example, a smartphone worn by the player may receive signals from the sensor modules 18. These signals contain the sensor data 32 and may, but need not, be wirelessly transmitted by the sensor modules 18 for the intermediate device. The intermediate device then sends the collected sensor data to a server (e.g., a web server) reachable over the internet. This may be done over an existing cellular data connection that traverses the internet, whereby the computing device 42 may connect to the same web server over the internet in order to access the collected sensor data 32.

Figure 2:
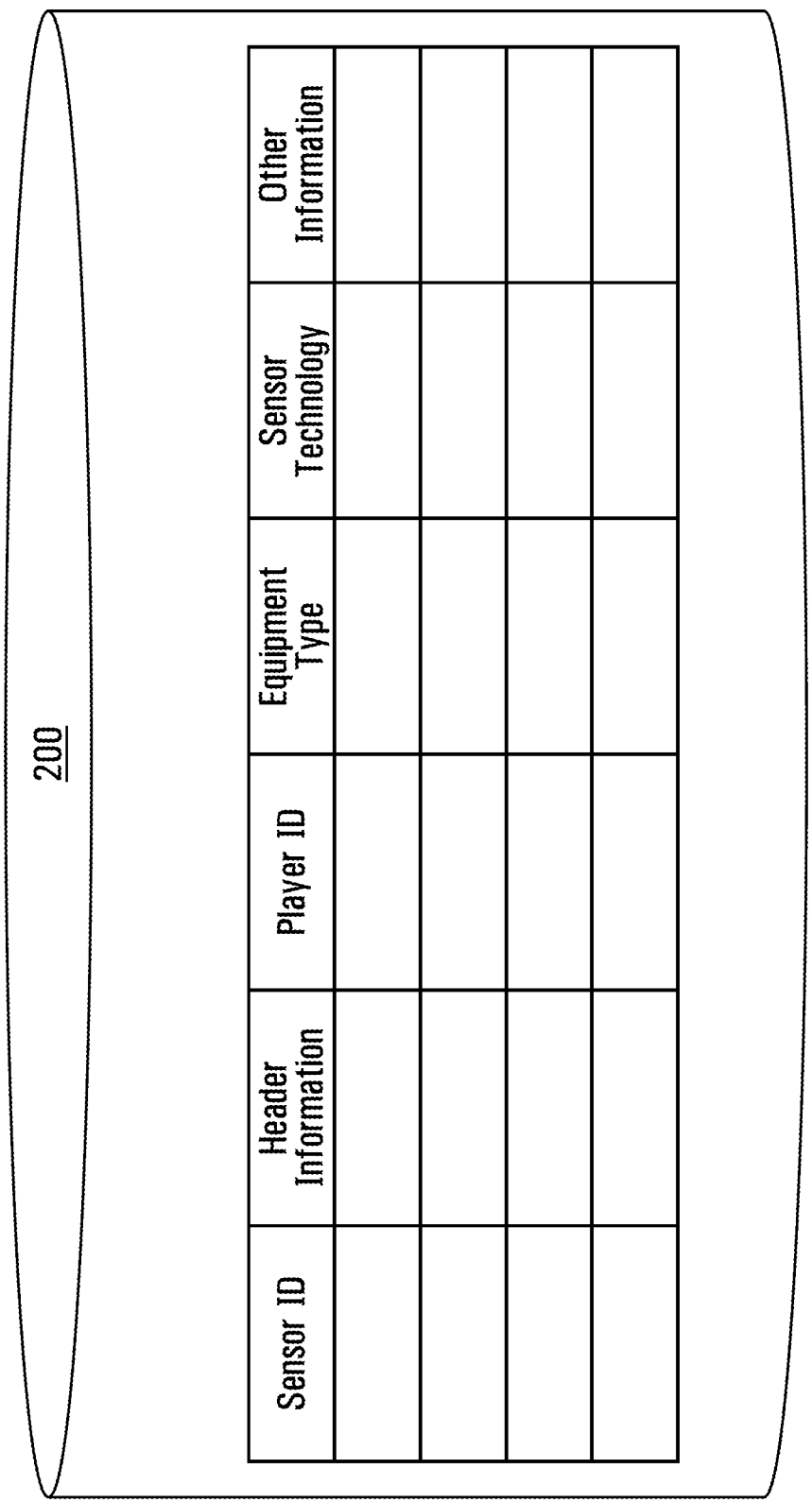
FIG. 2 illustrates a non-limiting example of a database storing sensor information.

A database 200 stores information regarding the various sensors 22 used in the environment 10 of FIG. 1. By way of non-limiting example, FIG. 2 shows this information in the form of a table (which may be stored in the memory 38 of the computing device 42). Of course, a table is merely used as a non-limiting example of how data may be stored in a non-transitory medium. The table includes a plurality of rows, one associated with each sensor 22. The table also includes a plurality of columns, each corresponding to a field for each row (and therefore each sensor 22). Examples of such fields may include:

ID: a unique identifier (ID) of the sensor.

Header information: data that is transmitted from the sensor module to enable a receiver to uniquely identify this sensor among other sensors. This could be a code associated with the sensor.

Player: a unique ID (e.g., name or team+number) of the player associated with that sensor. This association may exist be by virtue of the player wearing or using equipment associated with that sensor.

Equipment type: the type of equipment (such as skate, helmet, stick, etc.—see above for a more comprehensive list relevant to hockey), or apparel (jersey, socks, etc.), to which the sensor is attached or wherein the sensor is embedded.

Sensor technology: data that characterizes the type of sensor and, naturally, the type of data collected. Examples may include "IMU", "pressure sensor", "strain gauge", "body motion capture" and "heart rate".

Other information: data such as sensor make and model, serial number, battery expiry date, RF band, etc.

Figure 3:
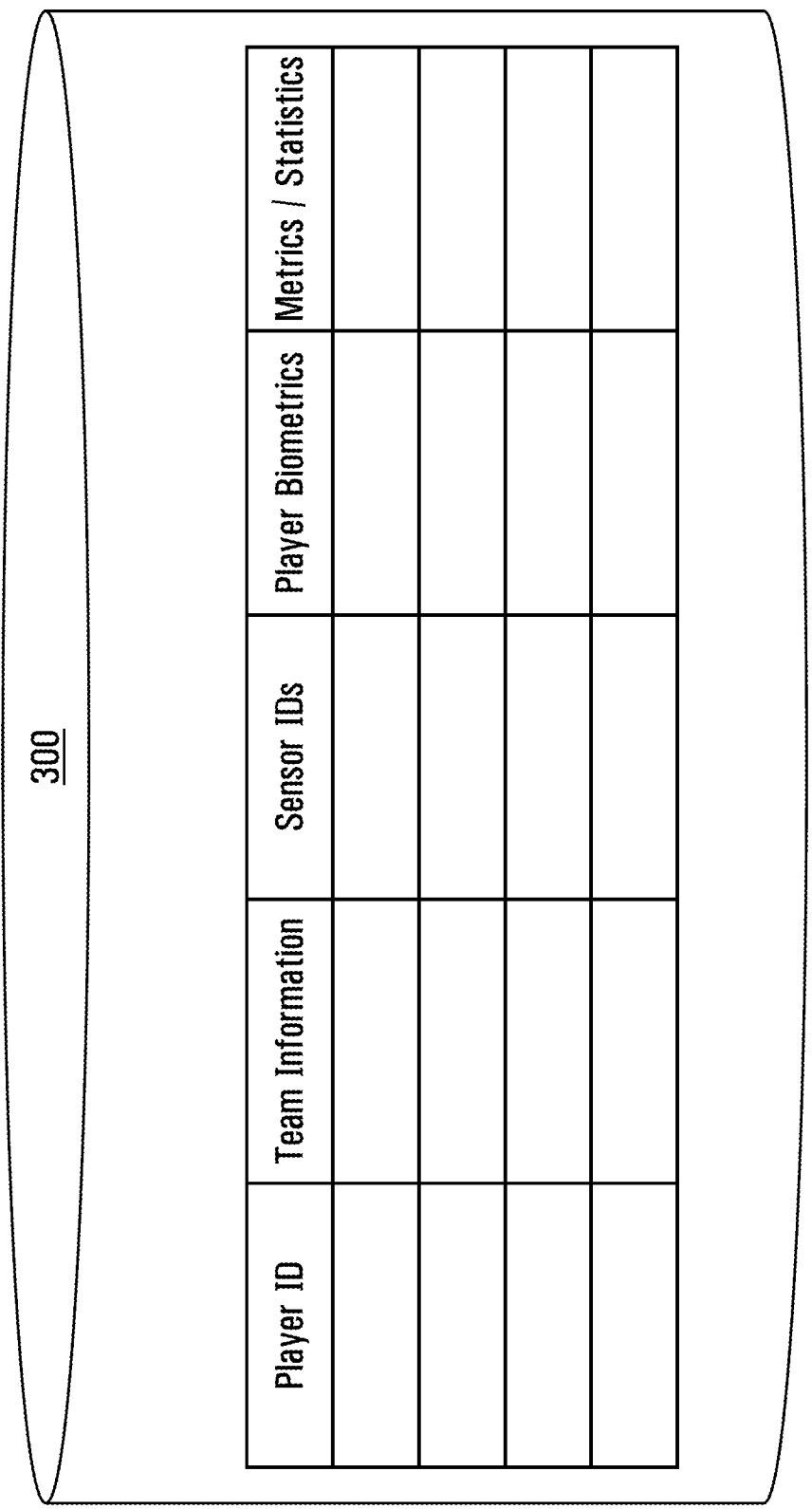
FIG. 3 illustrates a non-limiting example of a database storing player information.

An additional database 300 stores information regarding the players $14_1$-$14_P$. By way of non-limiting example, FIG. 3 shows this information in the form of a table (which may be stored in the memory 38 of the computing device 42). Of course, a table is merely used as a non-limiting example of how the data may be stored in a non-transitory medium. The table includes a plurality of rows, one associated with each player $14_i$. The table also includes a plurality of columns, each corresponding to a field for each row (and therefore each sensor 22). Examples of such fields may include:

ID: a unique identifier (e.g., name) of the player.

Team info: player's team and number.

Sensor(s): a unique ID of the sensor(s) associated with the player.

Player biometric information: height, weight, age, etc.

Metrics/Statistics: this information is described herein below

In some embodiments, a position determining system 72 can be provided so as to allow the approximate positions of the sensors 22 (and the individual players $14_i$ associated with those sensors 22) to be determined in 3D space. More specifically, there is a need for a system that allows the sensors 22 and individual players $14_i$ to be located in an indoor space. Several possibilities for gathering position data 90 are envisaged:

a) A non-camera-based wireless position determining system 74 connected to the I/O interface 60 of the computing device 42. Non-limiting examples include a fixed, calibrated system made up of an arrangement of high-speed indoor UWB receivers, and a portable calibration-less localization system made up of an arrangement of beacons installed at pre-determined locations.

In some embodiments of the non-camera-based position determining system 74, data from a physical sensor is wirelessly received at multiple receivers 44 and correlated/triangulated in order to determine the location of the physical sensor and therefore the associated article of equipment 30 (or player $14_i$). In such embodiments, the non-camera-based wireless position determining system 74 is embodied together with the receiver system 40 discussed above, as it is the sensor data 88 that is used to derive position data 90.

In other embodiments, one or more tags 76 (e.g., passive or active RFID tags) that are specifically configured for the non-camera-based wireless position determining system 74 may be provided. The tags 76 are applied to articles of equipment 30 and data 68 from a given tag 76 is wirelessly received at multiple receivers 44 and correlated/triangulated in order to determine the location of the given tag 76 and therefore the associated article of equipment 30 (or player $14_i$). In such embodiments, the non-camera-based wireless position determining system 74 is separate from the receiver system 40.

b) A camera-based position determining system 82, which can include one or more cameras 84 that acquire images of on-ice activity over time (i.e., "camera-captured data"). The camera system 82 may be connected to the I/O interface 60 of the computing device 42, allowing the computing device 42 to collect camera-captured data 78 in addition to raw sensor data 32. The camera-captured data 78 may be useful to generate position data 90 for locating the sensors 22 in space. Specifically, by knowing which sensors 22 are associated with which individual player $14_i$ of the plurality of players $14_1$-$14_P$ (e.g., from the databases 200 and 300), and by recognizing individual players $14_i$ (and tracking their locations) based on the camera-captured data 78 using image processing, it is possible to determine where individual sensors 22 are located in 3D space.

Once the sensors 22 and/or articles of equipment 30 are located in 3D space, using either position determining system 74, 82 (or a combination of both), metrics can be obtained that go beyond those that can be extracted from just the raw sensor data 32.

Figure 29A:
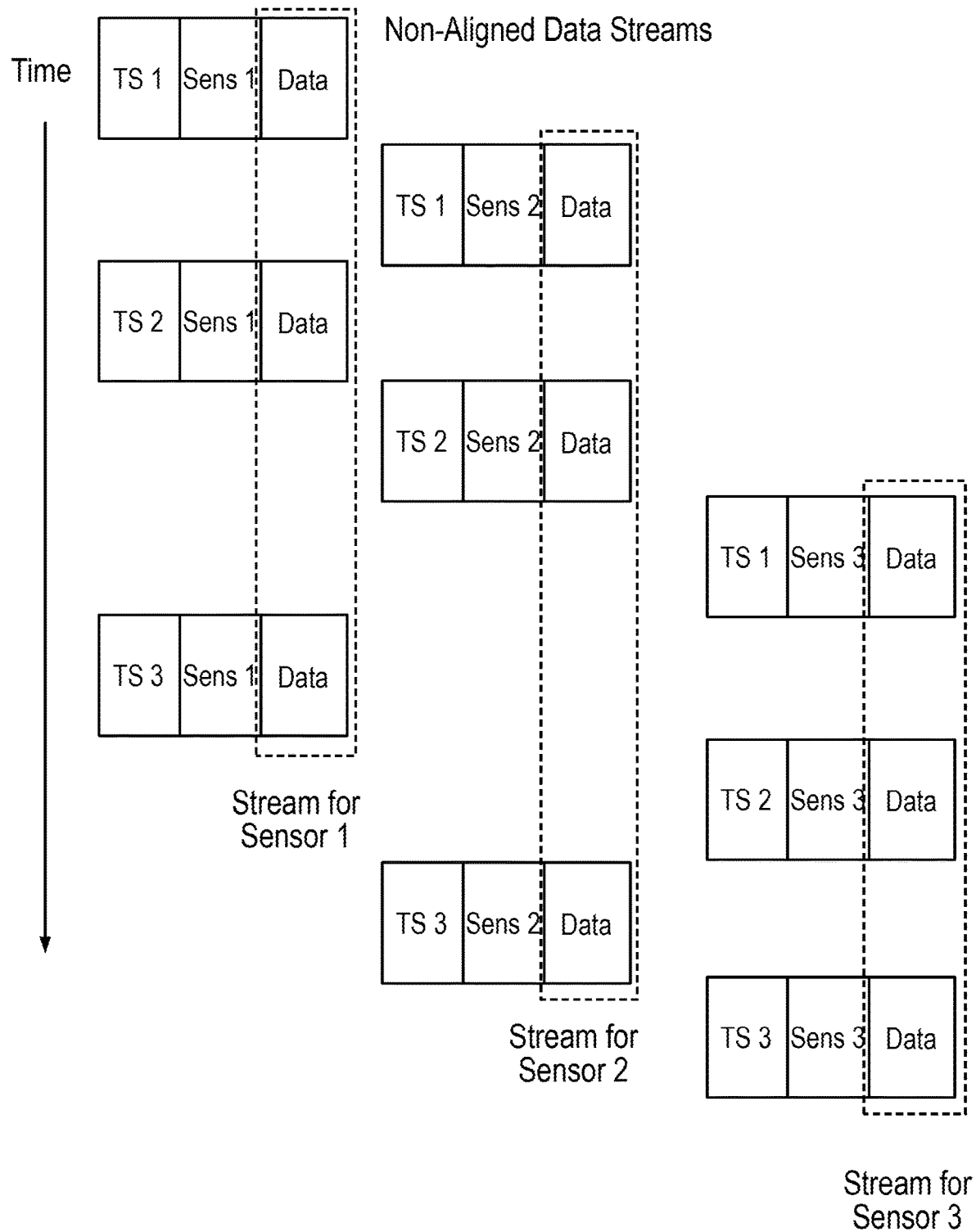
FIGS. 29A-29B are conceptual diagrams illustrating time-alignment of sensor data.
Figure 29B:
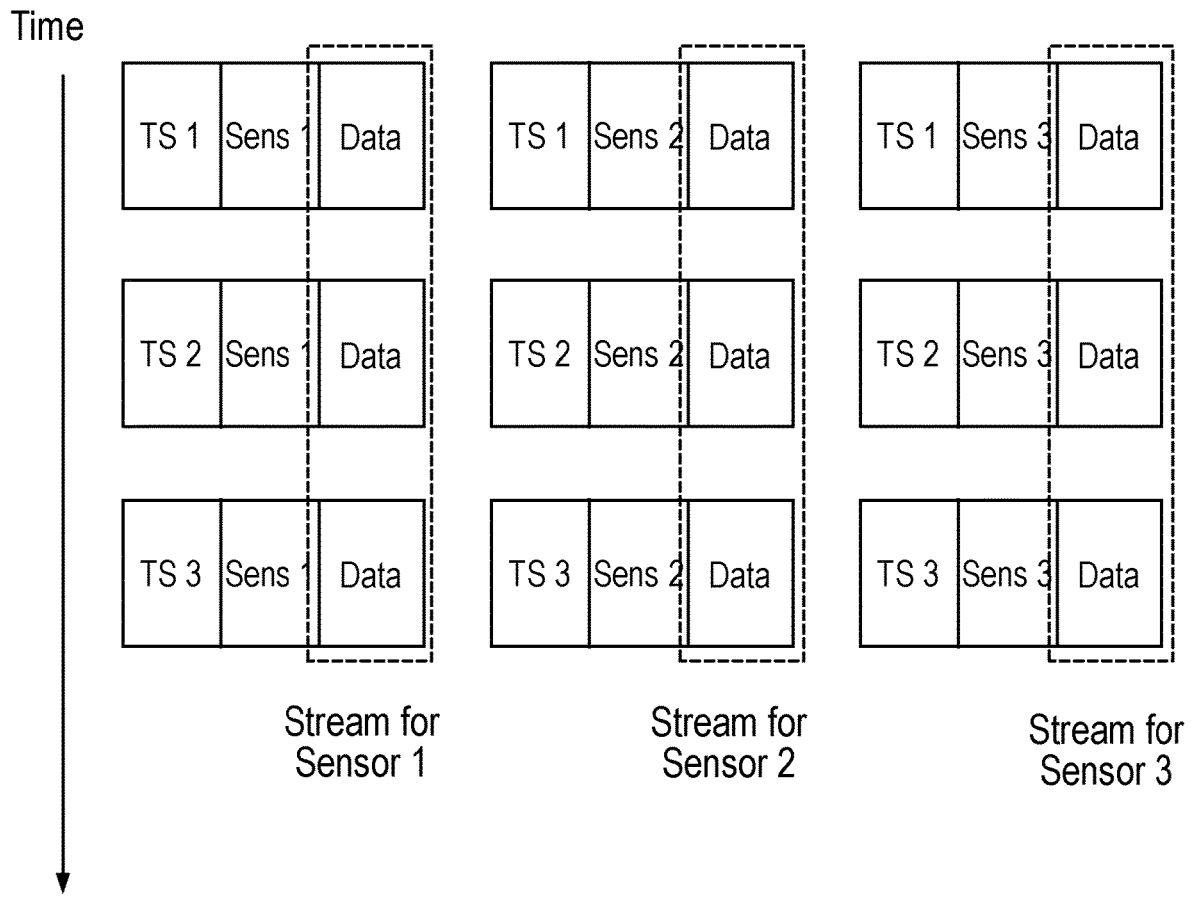

Turning now to the processes that can be carried out by the processing entity 54, these can include a synchronization process for synchronizing the received raw sensor data 32 with other raw sensor data 32 and with the position data 90. Synchronizing of this data is needed because of variable delay that can be introduced for numerous reasons. For example, the distance between a sensor 22 worn by a player $14_i$ and the receiver 44 will vary over time as the player $14_i$ travels on the ice. Also, different sensors 22 may take different amounts of time to process the readings that they make. Also, as transmission from the sensors 22 to the receiver 44 is wireless, the transmitted signals 34 may undergo a variable delay due to different CPU processing times as well as network latency variations. A result of the synchronization process may thus be an alignment in time of the various raw sensor data 32 and position data 90. In some embodiments, synchronization may be achieved by (i) determining the time stamps contained in the headers of the various packets conveyed by the various wireless signals received from the sensor modules 18; and (ii) associating grouping together those sensor signals having the same corresponding time stamp. This is illustrated in FIGS. 29A-29B, which illustrate streams of data for each sensor arriving in a staggered way (FIG. 29A) and which are time-aligned in FIG. 29B. It will be seen that the resulting sensor data can be grouped according to according to sensor, and can also be further grouped according to player. Position data may also be handled in the same way. The foregoing presupposes that a common reference time is used when generating or sending the sensor data 32 (and determining the position data 90), so that the alignment performed by the computing device accurately successfully groups together all readings associated with the same or similar time instant. The use of a common time reference for transmission could be managed by GPS or an offline time alignment mechanism.

Another process that could be carried out by the processing entity 54 may be a task identification process. To this end, the processing entity 54 may be configured to process the output of, say, a camera or an inertial movement unit (IMU) to recognize movement of the player or of the article of sports equipment 30 and to determine whether this movement matches sufficiently closely one of a plurality of predetermined movement patterns or tasks stored in the memory. This comparison can be done in various ways, including algorithmic processing, look-up tables, principal component analysis and using machine learning. In machine learning, a trained model uses parameters, which are internal configuration variables whose value can be estimated from the given data. Different parameters represent different tasks, depending on the classification. For example, the machine learning algorithm may be trained to distinguish between:

left turn vs. right turn
forward skating vs. backward skating
straight skating vs. turning
accelerating vs. decelerating
slap shot vs. wrist shot Also, the machine learning model may be trained to detect bench vs. ice time, or other conditions, including conditions that may arise in other sports, including turns, jumps and landings.

Another process that can be carried out by the processing entity 54 may include a metric extraction process for extracting metrics from the raw sensor data 32 and the position data 90. This is now described in further detail.

The raw sensor data 32 may essentially consist of signals 34 containing one or more streams of time-stamped data 114 representing the value of, or changes in, acceleration, pressure, direction, body movement, temperature, etc., as recorded, reported or measured by an individual sensor 22. Apart from being synchronized, this raw sensor data 32 needs to be intelligently processed together with the position data 90. Firstly, it is recognized that the raw sensor data 32 collected during a particular time window will be vastly different (in terms of both format and content) for different sensor types, even when collected from the same piece of equipment 30. For instance, a heart rate monitor does not produce the same results as an accelerometer. Also, the collected data 32 will be vastly different (in terms of at least content) as a result of the equipment 30 with which it is associated, even for the same type of sensor 22. For instance, acceleration data collected from a glove will be vastly different from acceleration data collected from a helmet, even during the same time window. Also, the collected data 32 will be vastly different (in terms of at least content) as a result of the task that would have been identified by the task identification process. For instance, if it is known that the player is executing a slap shot, or is skating backwards, this a priori information may lead to a more accurate outcome when processing the sensor data 32 and position data 90.

As such, knowing (e.g., from database 200) that each sensor 22 is of a particular type and is associated with a particular piece of equipment 30 and is associated with a certain task, a sensor data processing algorithm 950 that is equipment- and sensor-dependent can be applied to the raw sensor data 32 so as to extract certain metrics. Examples of metrics that can be extracted purely from raw sensor data 32 include:

acceleration/deceleration;
change of direction;
heart rate;
pressure;
strain/tension;
temperature;
etc.

Position data may 90 come in at least three forms: (i) inherent sensor data that is triangulated to generate inherent position data 90; (ii) specific signals from tags 76 of an independent non-camera-based position determining system 74; and (iii) camera-captured data 78 such as one or more streams of time-stamped image frames from respective viewpoints. The processing of position data 90 can allow the extraction of certain other metrics, examples of which include:

the positions of individual players relative to the ice surface and to one another;
the speed of individual players;
whether the player is shooting the puck;
whether a given player is on the ice or on the bench;
whether a goalie is standing or has dropped to the ground;
which player or team has possession of the puck;
etc.

Furthermore, in the case of images, and with the help of an image processing algorithm 980 applied to the camera-captured data 78, it may be possible to identify and track various parts of a human body, such as the limbs and head (for example, see U.S. PG Pub. 20190091541 to Schulte et al., hereby incorporated by reference herein). Also, the image processing algorithm 980 may also be configured to identify and track certain types of equipment 30 such as skates, helmets and sticks, as well as the number on the back of a jersey or on a piece of equipment 30. The image processing algorithm 980 may also be configured to identify and track the puck.

Hybrid Metrics

Given the uncontrolled progression of a hockey game, merely knowing that a sensor 22 produces a certain raw sensor data 32, or merely knowing the positions of individual players 14$_i$ or sensors 22, does not reveal useful information. This is because one has little contextual information about an event that may be manifesting itself in the raw sensor data 32 being collected. As such, it may be beneficial to combine or fuse the raw sensor data 32 from some sensors 22 with position data 90 associated those sensors 22 in order to produce new "hybrid" metrics that have been heretofore unavailable.

A hybrid metric indicative of an aspect of performance involving the article of sports equipment is generated based on the synchronized collection of data (sensor data and position data), which may be from multiple sources of player equipment, as opposed to a single catch-all sensor. By sourcing multiple sensors specific to various equipment types, errors are minimized and a best-fit approach is used to gain confidence in the metrics calculated.

In some embodiments, a hybrid metric may be referred to as a hybrid parameter, which is obtained by combining at least one first parameter (obtained from sensed data sensed by at least one sensor) and at least one second parameter (obtained from position data associated with the at least one sensor or the article of equipment) using a predetermined formula or using a classification system. By using parameters derived from different sources of data, at least one source conveying physical sensed data and at least one other source conveying position, the hybrid parameter reveals characteristics that are not obtainable from either the physical sensor data alone or the position data lone. Such characteristics may relate to efficiency, playing style and so on.

For example, measuring force in a skate is possible through an instrumented footbed, or strain gage. On the other hand, measuring velocity/speed may require is another reference system, such as the position determining system. For instance, even if each leg's stride rate is known (e.g., using an IMU integrated with the aforementioned force sensor), it may not be known how far the skate moves per stride (due to the glide phase), so a reliable velocity may not be available from the sensor data alone. On the other hand, a position determining system cannot measure force and therefore cannot measure instantaneous energy or exertion, which means that efficiency calculations require both sets of measurements (sensor data and position data).

Figure 19:
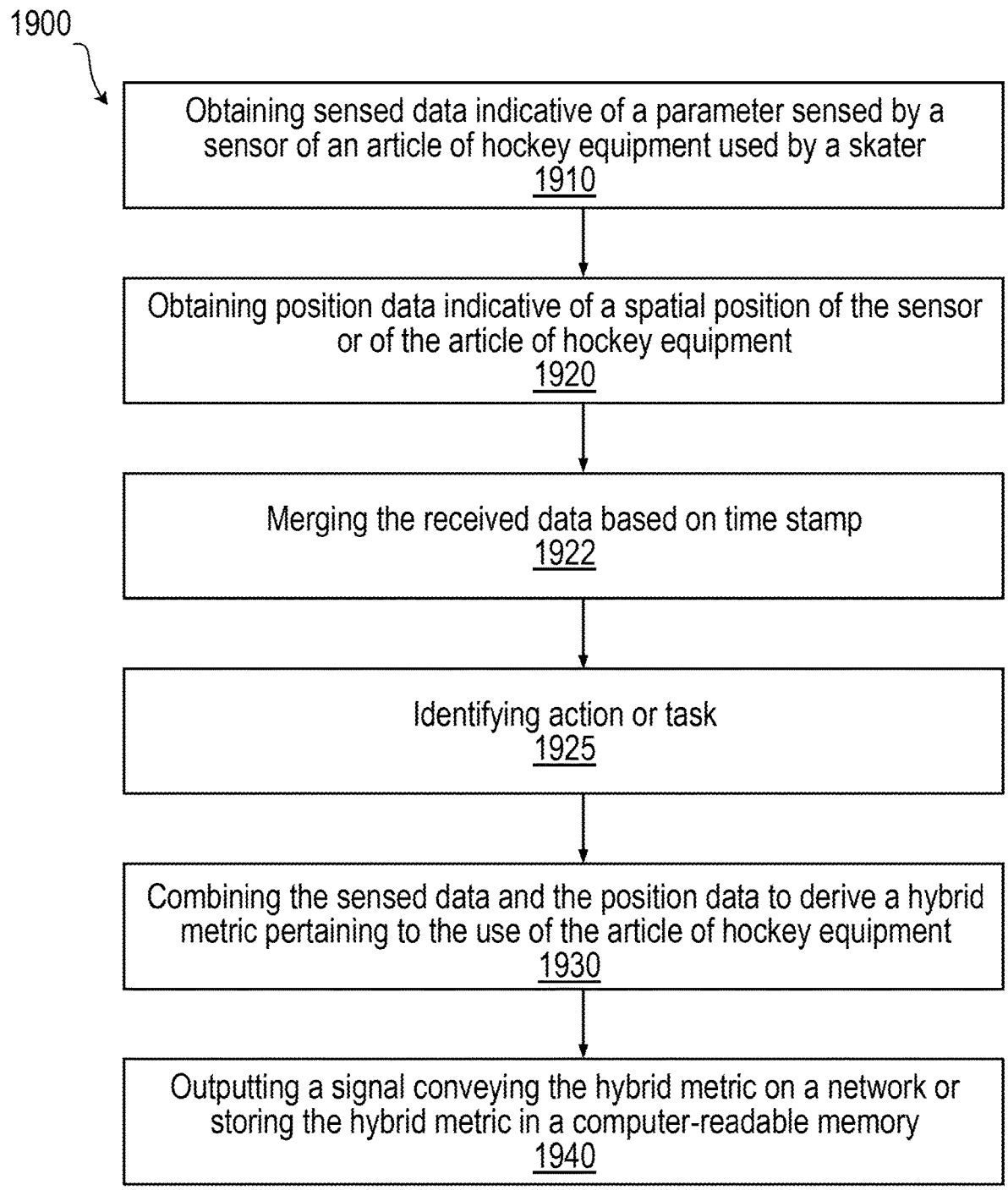
FIG. 19 is a flowchart illustrating steps of a method for producing hybrid metrics, in accordance with a non-limiting embodiment.

As such, the computing device 42 carries out a method 1900, which is now described with reference to the flowchart in FIG. 19. The method 1900 includes obtaining sensor data indicative of a parameter sensed by a sensor of an article of hockey equipment used by a skater (step 1910); obtaining position data indicative of a spatial position of the sensor or of the article of hockey equipment (step 1920); merging the received data based on time stamp (step 1922, which can implement the synchronization process previously described); combining the sensor data and the position data to derive a hybrid metric pertaining to the use of the article of hockey equipment (step 1930, which can implement the metric extraction process described herein above); and outputting a signal conveying the hybrid metric on a network or storing the hybrid metric in a computer-readable memory (step 1940). An additional step may be performed at step 1925, where an action or task is identified (either manually or based on a machine learning model—see the task identification process referred to herein above). Then, execution of step 1930, which involves the generation of a hybrid metric, depends on which action or task was identified at step 1925.

Figure 20:
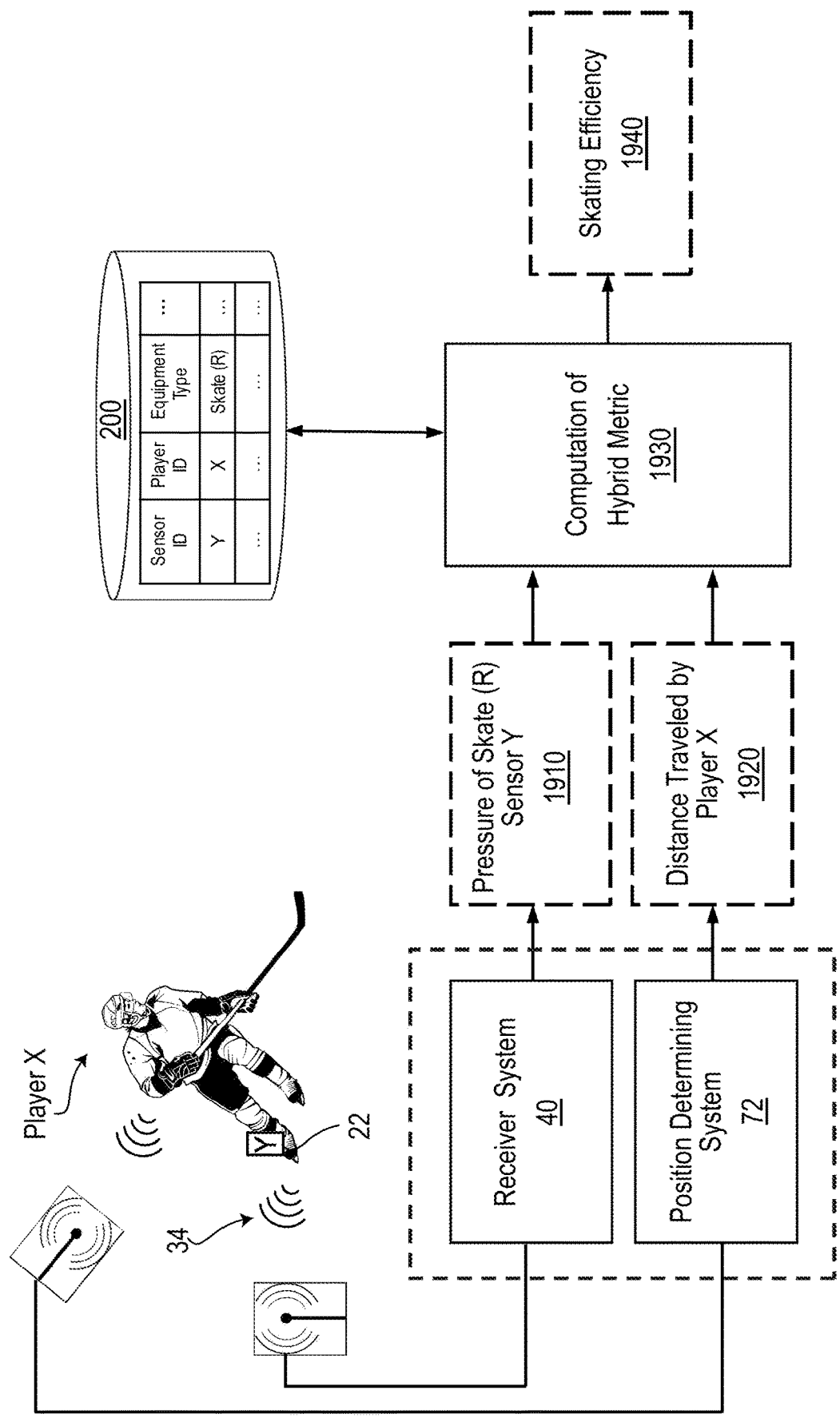
FIGS. 20 to 23 are block diagrams illustrating non-limiting examples of the computation of hybrid metrics.

For example, with reference to FIG. 20, assume that player X has a sensor Y on his right skate. This association between player X and sensor Y (and the right skate) may be stored in the database 200. Assume now that sensor Y is a pressure sensor configured to detect changes in applied pressure, so as to allow estimation of how much energy player X is putting into making strides (i.e., cycles of pushing down towards the ice and lifting off). Meanwhile, assume that player X and, in particular, his right skate can be identified and tracked by the position determining system 72. This implies that the physical trajectory of player X's right skate can also be tracked, including the total distance traveled by player X's right skate. Once this trajectory is synchronized with the raw sensor data 32 collected from the pressure sensor on player X's right skate, one can obtain a more complete picture of the relationship between the displacement of player X's right skate and the energy expended to travel that distance. This allows the computation of a "skating efficiency quotient", e.g., by dividing the distance traveled by a measure of the overall cumulation (e.g., an integral) of the sensed pressure over a given time period. This quotient can then be normalized by biometric data (such as the player's height and/or weight) provided in database 300. The skating efficiency quotient is an example of a hybrid metric that cannot be adequately computed based on raw sensor data 32 alone or based on position data 90 alone. An analogous skating efficiency quotient can be obtained from the data 32, 90 associated with player X's left skate, and an average of the two quotients can be taken to determine an average skating efficiency for player X. It is noted that the aforementioned measurements can be taken over a fixed or variable period of time, which may be pre-determined or specified prior to measurement.

Figure 21:
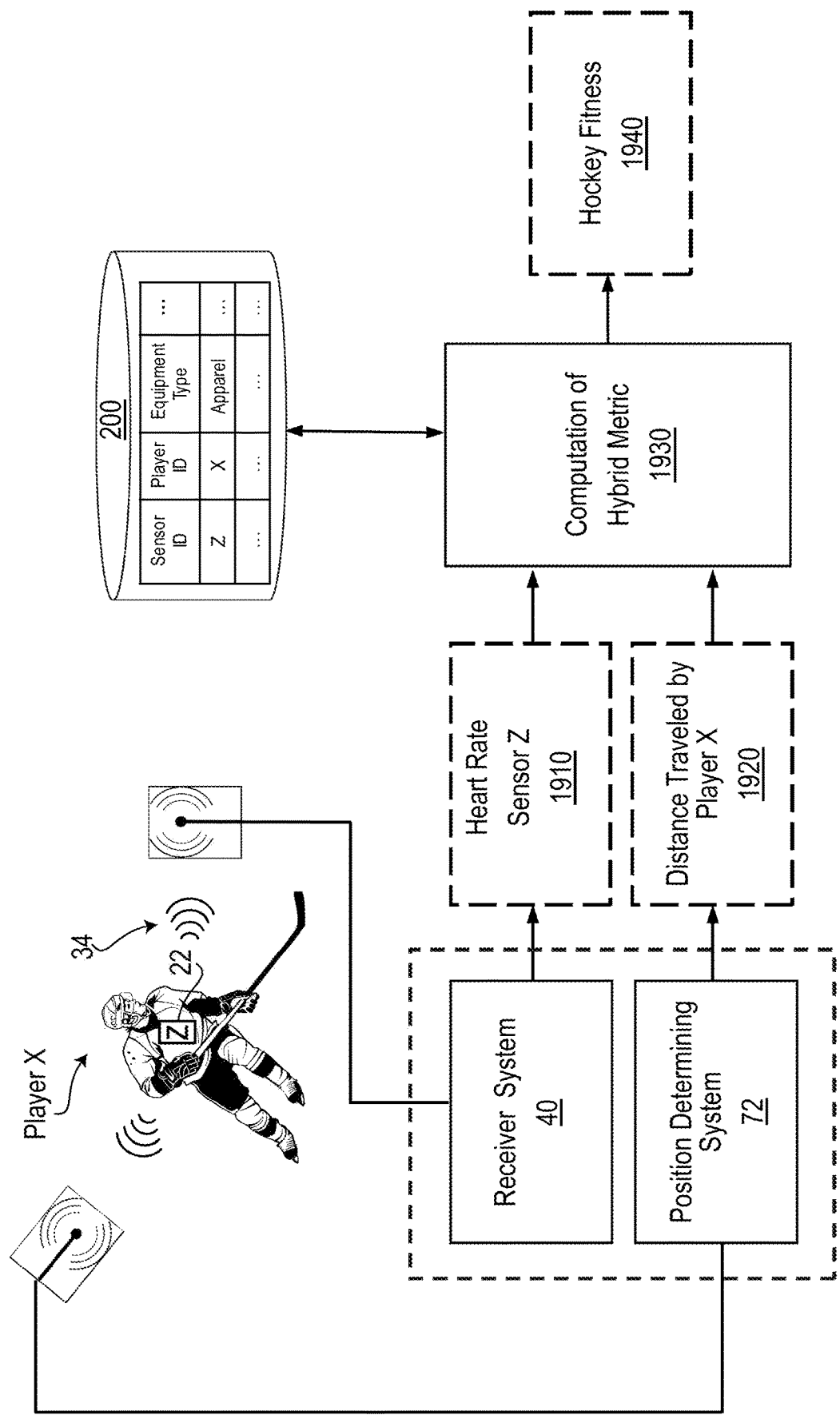

In another example, with reference to FIG. 21, assume that player X has sensor Z embedded in his apparel. This association between player X and sensor Z (and the apparel) may be stored in the database 200. Assume also that sensor Z is a heart rate monitor configured to measure player X's heart rate and that player X can be identified and tracked by the position determining system 72. Then, the physical trajectory of player X can also be tracked. Once this trajectory is synchronized with the data collected from player X's the heart rate monitor, one can obtain a more complete picture of the relationship between the displacement of player X and the evolution of player X's heart rate. This allows the computation of a "hockey fitness", e.g., as a function of heart rate and distance traveled over a given time period. The hockey fitness metric can then be normalized by biometric data (such as the player's height, age, weight, gender, etc.) provided in database 300. The hockey fitness metric is another example of a hybrid metric that cannot be adequately computed based on raw sensor data 32 alone or based on position data 90 alone. Further adjustments to the hockey fitness metric can be made on parameters such as when during the game the measurements where made (e.g., beginning or end), altitude of the rink above sea level, and other parameters.

Figure 22:
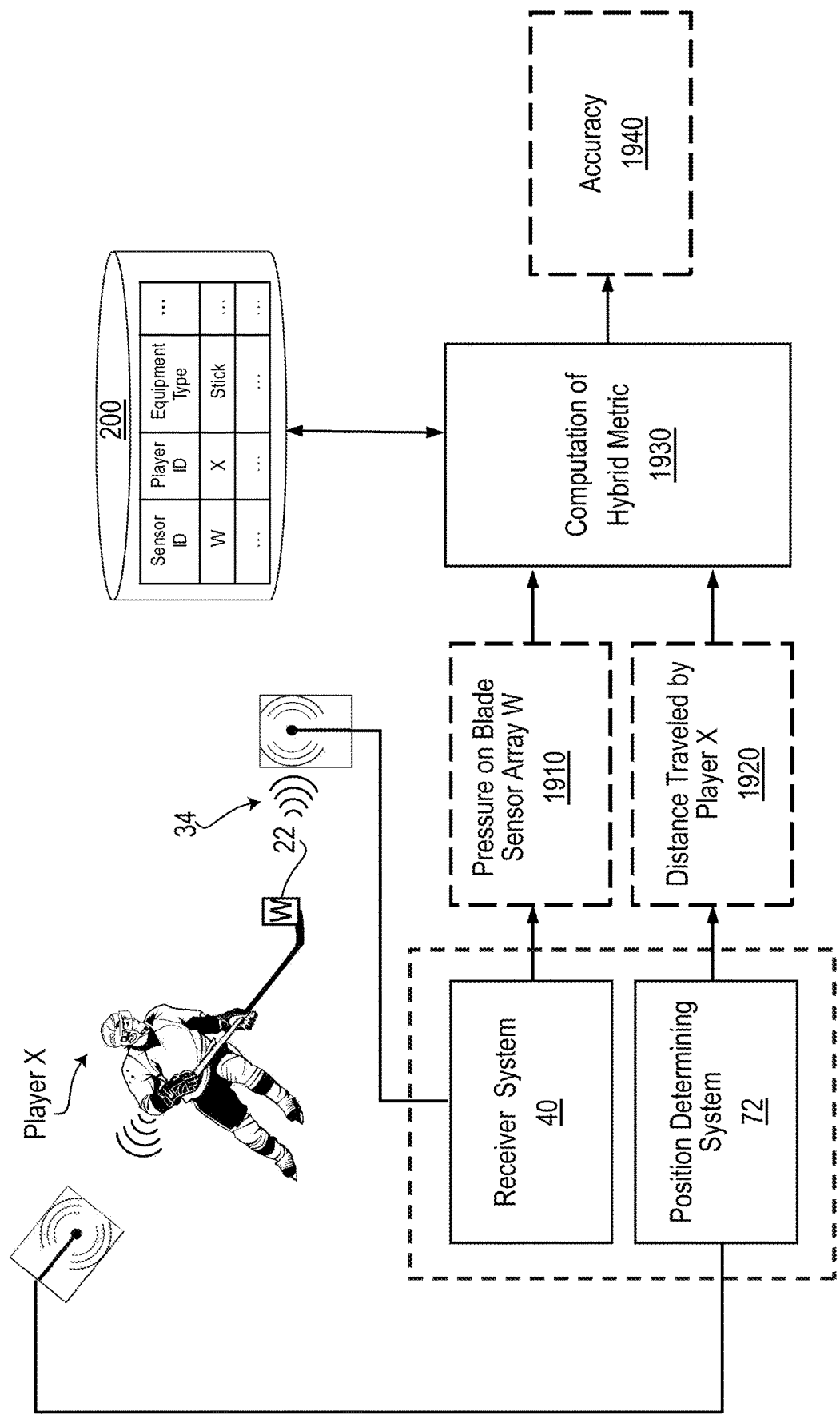

In another example, with reference to FIG. 22, assume that player X has a sensor array W embedded along the blade of his hockey stick. This association between player X and sensor array W (and the hockey stick) may be stored in the database 200. Assume now that sensor array W is a pressure sensor configured to detect which part of the blade of the hockey stick is in contact with puck. Meanwhile, assume that the puck can be identified and its trajectory tracked by the position determining system 72. The position determining system 72 can also detect whether the puck is traveling towards the goal or wide of the goal, i.e., whether a shot on net has been released. This can be determined based on a comparison with a known position of the goal. Once the trajectory of the puck is synchronized with the data collected from the sensor array W on player X's stick, one can obtain a more complete picture of where the puck was on the stick when the shot was released, and whether the shot was on net. This "accuracy" metric that relates shot accuracy to where the puck was when the shot was released is an example of a hybrid metric that cannot be adequately computed based on raw sensor data 32 alone or position data 90 alone. In particular, if the position determining system 72 is non-camera-based, the position data 90 may only indicate the position of the sensor 22 on the stick but may not indicate what part of the stick made contact with the puck. On the other hand, if the position determining system 72 is camera-based, the resulting images may not reveal what precise part of the blade was in contact with the puck (due to obfuscation by skates or the stick or the player). And only using the sensor array W, one has no clue as to whether the shot was on the net or wide. As such, the sensor array W and the position determining system 72 provide complementary information to enable a more reliable and useful computation of the aforementioned "accuracy" hybrid metric.

In yet another example, a hybrid metric relates to a player's skating caliber. This could involve processing the position data 90 in order to obtain the distance traveled by the player $14_i$, combined with metrics extracted from raw sensor data 32 (such as the number of strides it takes to cover that distance, change in acceleration and direction indicative of the player's ability to quickly change directions, etc.), and thresholding the output to provide the player's skating caliber, i.e., whether the player is a low-, medium- or high-caliber skater.

The aforementioned algorithms for processing raw sensor data 32 and position data 90 may implement feature recognition techniques to identify specific movements, events, etc. that can then be 'trained' to come to the appropriate conclusions/feedback to the player $14_i$. For example, the computing entity may be configured to process the output of the position determining system 72 to recognize movement of the player $14_i$ or of the article of sports equipment 30 of the player $14_i$, and to determine whether this movement matches sufficiently closely one of a plurality of predetermined movement patterns stored in the memory 38. This comparison can be done in various ways, including algorithmic processing, look-up tables, principal component analysis and using machine learning. In machine learning, a trained model uses parameters, which are internal configuration variables whose value can be estimated from the given data. Different parameters represent different movement patterns, depending on the classification. For example, the machine learning algorithm may be trained to distinguish between:

left turn vs. right turn
forward skating vs. backward skating
straight skating vs. turning
accelerating vs. decelerating
slap shot vs. wrist shot Also, the machine learning model may be trained to detect an approaching puck, and impact of a puck or other projectile, or other conditions, including conditions that may arise in other sports, including turns, jumps and landings.

Moreover, it should be appreciated that although the above hybrid metrics used for measuring athletic performance are derived from the raw sensor data 32 originating from one sensor 22 in combination with intelligent processing of the position data 90, it is possible and in fact likely that improved hybrid metrics will be derived from the raw sensor data 32 originating from multiple sensors 22 in combination with intelligent processing of the position data 90.

Also, in some embodiments, there will arise a situation where the sensor data is transmitted during a time period that spans a glide phase during which the position of the sensor changes without a change in the sensor data collected by the sensor. In this case, a camera may be configured to capture images of the article of sports equipment during the glide phase, and the computing device may be configured to receive the images of the article of sports equipment, synchronize the images with the sensor data, detect positional information about the player or the sensor (based on the images), and combine the positional information with the sensor data to derive information, such as a hybrid metric, specific to the glide phase.

The following shows non-limiting examples of new/hybrid metrics that can be computed based on processing of raw sensor data 32 of one or more types of sensors 22 on some types of equipment 30 (third column), combined with the intelligence gained from the position data 90 (fourth column):

Stick Metrics

| Hybrid Metric | Description | On-Body/Gear Sensor Contribution | Positioning System Contribution |
|---|---|---|---|
| Shooting Efficiency | Combine data about how the player loads the stick to the resultant shot characteristics to determine how efficient they are as a shooter (energy in -vs- energy out). | Determine stick loading and manipulation properties from: IMU, Strain Gage and/or Pressure Sensor | Determine shot speed and/or release velocity from position data |
| Shooting Accuracy | Combine data about how the player loads and manipulates the stick to the resultant shot characteristics to determine properties that lead to shooting accuracy. | Determine stick loading and manipulation properties from: IMU, Strain Gage and/or Pressure Sensor to | Determine shot speed, release velocity and/or trajectory from position data |
| Shooting Style | Combine data about how the player loads and manipulates the stick with their tendencies -vs- a population of players so their most common tendencies can be classified. (i.e. quick releases from high slot, slap shots from the point, one timers from the wing). | Determine stick loading and manipulation properties from: IMU, Strain Gage and/or Pressure Sensor to | Determine shot speed, release velocity, trajectory and/or location on ice from position data |

Figure 30:
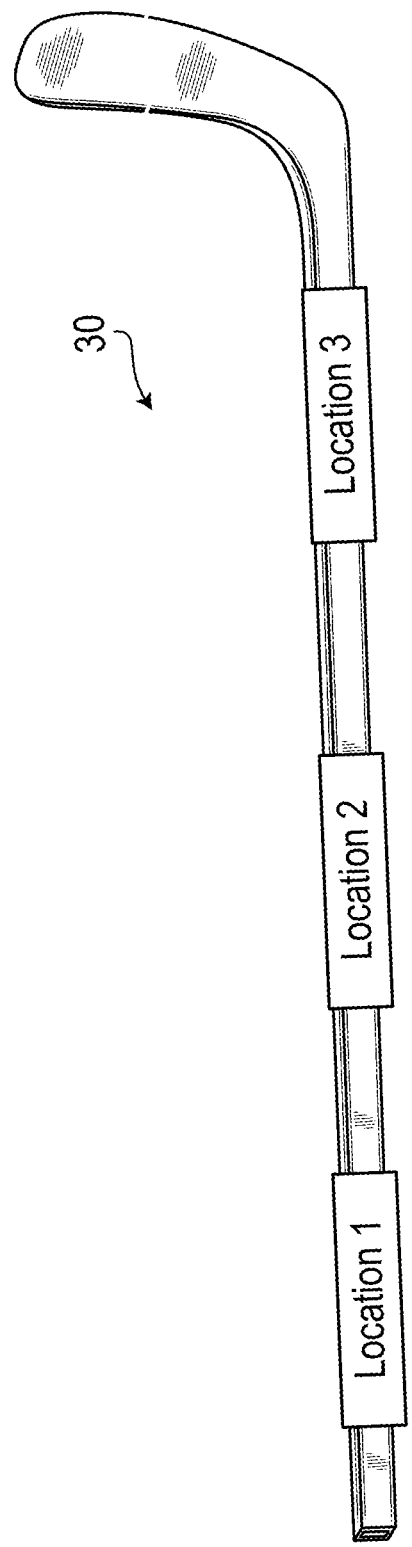
FIG. 30 shows various possible positions of a strain gage on a hockey stick.

The generation of the SHOOTING EFFICIENCY metric is now described in further detail by way of example:

Strain gages mounted along the length of a hockey stick dynamically measure the forces applied to the stick and determine the resulting output characteristics. See, for example, possible positions in FIG. 30; strain gages may be located at more, fewer or different positions in other embodiments.

These strain gages are calibrated to the mechanical properties of the stick (e.g., stiffness, kickpoint) to correlate to a force measurement such that the measured strain can detail the applied force on the stick at differing locations. This can be done through Hooke's law and the modulus of elasticity (E)=Stress/Strain. As stress is equal to force divided by cross sectional area, the mechanical and geometric properties of the stick can be used to create specific modulus and area values that allow the force to be calculated from the strain measurement.

This range of input characteristics can then be correlated with the output characteristics (shot speed and/or release velocity) to classify the shooting efficiency of the player.

Puck tracking (e.g., via video or UWB tracking methods) provide the shot speed and/or release velocity measures.

As such, position data is combined with sensor data to produce a hybrid metric of shot efficiency that is not derivable from collected sensor data alone or from position data alone. The input forces used to calculate this hybrid metric could be a sum (e.g., a weighted sum) of input forces from all locations on the stick or they could be the input forces from individual locations based on the stick type. More specifically, the shot efficiency may be classified as follows:

High efficiency→low input force, fast shot velocity, release velocity.

Average efficiency→average input force, average shot velocity, release velocity.

Low efficiency→high input force, slow shot velocity, release velocity.

There may be a greater or smaller number of efficiency levels in other embodiments. The aforementioned three efficiency levels can be separated in a multivariate space using machine learning, or based on a distance metric, for example. For instance, baseline values for the input force, shot velocity and/or release velocity could be used as "average" values, "high" values and "low" values. Thereafter the difference between measured values (for an actual shot) and the baseline values for each level could be determined and the level (low, average or high) producing the smallest distance could be the output efficiency for the actual shot.

Pressure sensors mounted under the hand locations of the player could also produce similar input force measurements (Pressure=Force/Area).

IMUs mounted at the hand locations could also be used to generate input measurements based on acceleration loading profiles (peak acceleration, rate of acceleration, length of time acceleration applied).

The generation of the SHOOTING ACCURACY metric is now described in further detail by way of example:

Data about how the player loads and manipulates the stick can be gathered in a variety of ways. Strain gages mounted along the length of a hockey stick dynamically measure the forces applied to the stick and determine the resulting output characteristics. See, for example, possible positions in FIG. 30; strain gages may be located at more, fewer or different positions in other embodiments.

The strain gages are calibrated to the mechanical properties of the stick (stiffness, kickpoint) to correlate to a force measurement such that the measured strain can detail the applied force on the stick at differing locations. For example, this can be done through Hooke's law and the modulus of elasticity (E)=Stress/Strain. As stress=force/cross sectional area, the mechanical and geometric properties of the stick can be used to create specific modulus and area values that allow the force to be calculated from the strain measurement.

This range of input characteristics can then be correlated with the output characteristics (shot speed and/or release velocity and/or puck trajectory) to classify the shooting efficiency of the player.

Puck tracking (e.g., via video or UWB tracking methods) provide the shot speed and/or release velocity and/or puck trajectory measures.

As such, position data is combined with sensor data to produce a hybrid metric of shot accuracy that is not derivable from collected sensor data alone or from position data alone. The input forces used to calculate this hybrid metric could be a sum (e.g., a weighted sum) of input forces from all locations on the stick or they could be the input forces from individual locations based on the stick type. More specifically, the shot efficiency may be classified as follows:

High accuracy→highly repeatable loading characteristics, highly repeatable shot speed, release velocity, puck trajectory.

Average accuracy→some repeatable loading characteristics, some repeatable shot speed, release velocity, puck trajectory.

Low accuracy→lack of repeatable loading characteristics, lack of repeatable shot speed, release velocity, puck trajectory.

There may be a greater or smaller number of accuracy levels in other embodiments. The aforementioned three accuracy levels can be separated in a multivariate space using machine learning, or based on a distance metric, for example. For instance, baseline values for the level of repeatable loading characteristics, level of repeatable shot speed/velocity and/or release velocity and/or puck trajectory could be used as "average" values, "high" values and "low" values. Thereafter the difference between measured values (for an actual series of shots with a particular stick and for a particular player) and the baseline values for each accuracy level could be determined and the accuracy level (low, average or high) producing the smallest distance could be the output shooting accuracy for the actual series of shots for the particular stick and player.

Pressure sensors mounted under the hand locations of the player could also produce similar input force measurements (Pressure=Force/Area).

IMUs mounted at the hand locations could also be used to generate input measurements based on movement patterns of the stick prior to shot release. These movement patterns could include acceleration in certain directions relative to the stick positioning in the hand along with time based measures of force application.

The generation of the SHOOTING STYLE metric is now described in further detail by way of example:

Data about how the player loads and manipulates the stick can be gathered in a variety of ways. Strain gages mounted along the length of a hockey stick dynamically measure the forces applied to the stick and determine the resulting output characteristics. See, for example, possible positions in FIG. 30; strain gages may be located at more, fewer or different positions in other embodiments.

The strain gages are calibrated to the mechanical properties of the stick (stiffness, kickpoint) to correlate to a force measurement such that the measured strain can detail the applied force on the stick at differing locations. For example, this can be done through Hooke's law and the modulus of elasticity (E)=Stress/Strain. As stress=force/cross sectional area, the mechanical and geometric properties of the stick can be used to create specific modulus and area values that allow the force to be calculated from the strain measurement.

This range of input characteristics can then be correlated with the output characteristics (shot speed, release velocity) to classify the shooting style of the player. The input forces used to calculate this measure could be done as a sum of all locations on the stick or as individual locations based on the stick type.

Load release (puck is loaded near back foot and released before front foot)→a higher input force higher up the stick and longer loading time is used to generate a higher shot speed and release velocity.

Drag release (puck starts away from body and is dragged towards front foot for release)→an angled input force applied in the middle of the stick is used to generate a higher shot speed and release velocity.

Push release (puck is loaded in front of the player's body)→a lower input force anywhere on the stick is used to generate a higher shot speed and release velocity.

As such, the system combines sensor data (from which is computed the input force, the position/distribution of the input force along the shaft of the stick and/or the puck loading time) with position data (from which is computed the shot speed and/or release velocity) in order to generate a hybrid metric of shooting style, which is not computable from the collected sensor data alone or from the position data alone.

There may be a greater or smaller number of shooting styles in other embodiments. The aforementioned three shooting styles levels can be separated in a multivariate space using machine learning, or based on a distance metric, for example.

Pressure sensors mounted under the hand locations of the player could also produce similar input force measurements (Pressure=Force/Area).

IMUs mounted at the hand locations could also be used to generate input measurements based on acceleration loading profiles (peak acceleration, rate of acceleration, length of time acceleration applied). The output of the IMUs could also be used to detect movement patterns such as acceleration in certain directions relative to the stick positioning in the hand along with time-based measures of force application.

Skating Metrics

| Hybrid Metric | Description | On-Body/Gear Sensor Contribution | Positioning System Contribution |
|---|---|---|---|
| Power Generation | Combine data about how the player generates movement on the ice to their measured skating outputs to determine their power generation capabilities. | IMU, Strain Gage and/or Pressure Sensor | Determine player acceleration and/or speed from position data |
| Skating Efficiency | Combine data about how the player generates movement on the ice to their measured skating outputs to determine how efficient they are (energy in -vs-energy out). | IMU, Strain Gage, Pressure Sensor and/or Heart Rate | Player acceleration, speed and/or distance from position data |
| Skating Technique | Combine data on how a player generates movement on the ice with their tendencies -vs- a population of players so their most common tendencies can be classified (short quick strides with strong ability to change direction, power skater with good straight line speed, good backwards skater). | IMU, Strain Gage and/or Pressure Sensor | Player acceleration, speed, change of direction and/or distance from position data |

The generation of the POWER GENERATION metric is now described in further detail by way of example:

Data about how powerful the skater is at an instant of time is collected through use of multiple sensing technologies including pressure sensors, strain gages and IMUs.

Skate power generation is determined by rate at which the player does work.

Power (Watts)=Work (J)/time (s)=$F*d*\cos(\Theta)/t(s)=F*V*\cos(\Theta)$, where $\Theta$ is the direction of the force vector relative to the direction of travel.

The applied force (F) is assumed to be encompassed by the interaction of the blade with the ice. As such, the force can be determined through an instrumented footbed in each skate insole, or through use of calibrated strain gages mounted in the skate holders. In the latter case, the force could be determined based on relative strain of the supporting materials (nylon, or carbon fiber)

Position is recorded through an external reference system based on optical or UWB tracking of the player, and velocity is calculated from position data using V=d/t, for a particular unit of time, which can be several milliseconds up to several seconds, for example.

Orientation of the skate blade relative to the ice and direction of travel can be determined using the IMUs.

Merging measured data from different data sources (force, based on sensor data and velocity, based on position data) into a hybrid metric provides an approximation of skating power (work per unit time).

The generation of the SKATING EFFICIENCY metric is now described in further detail by way of example:

Hockey is a dynamic, high intensity sport often with short bouts of high intensity action. As such, efficiency, as measured in the traditional fashion (steady state cyclical motion) may not translate well to a better player. As such, a more faithful measure of skating efficiency is related to the input forces of the player based on meaningful outcome goals in ice hockey. Minimization of normalized net force (% Body Weight) or physiological factor (VO2 or Heart rate) for a hockey-specific outcome (e.g. end-to-end skate, hockey productivity) would result in higher skating efficiency.

A simplified metric of skating efficiency could be based on total impulse as measured by integration of net force (pressure sensors in skate footbed, or strain gage on the skate) normalized by player weight and divided by the distance travelled during the session.

To prevent efficiency rewards for low activity levels, weightings would be introduced based on hockey player "productivity", which could be defined by the number of interactions with other players (defending player, passing puck, covering zone) and the puck (pass, shot, deflection) within a time period. These interactions can be measured in part based on position data collected by the position determining system which tracks the positions of various players as well as possibly the puck.

As such, the skating efficiency may be classified into, say, two categories, high efficiency and low efficiency, where:

High Efficiency Skater: High hockey productivity, low total impulse, high distance Low Efficiency Skater: Low hockey productivity, high total impulse, low distance Of course, since the space covered by the three aforementioned parameters is three-dimensional, any suitable technique can be used to divide this space into two portions that allow straightforward discrimination between the two levels, including distance metrics, possibly modulated by previously measured baseline values for each parameter.

A greater number of efficiency categories can be devised.

The generation of the SKATING TECHNIQUE metric is now described in further detail by way of example:

Skating technique is determined first by classifying the actions of an instrumented player into defined hockey specific characteristics (cross overs, tight turns, direction changes, stride rate, top speed).

Machine Learning algorithms based on sensor data (IMUs, pressure sensors, position data) can be employed to classify the players recorded sessions into frequency of each defined characteristic.

The player's skating technique can be determined through characterization of their recorded sessions over a selected period of time (game, season) into a distribution of these core characteristics.

The distribution of these characteristics are then compared to the characteristics associated with a database of players who are pre-defined as having a specific skating technique (power forward, dynamic forward, agile defenceman, aggressive defenceman) by expert observers (coaches, trainers). This would be done offline, and stored in a database. In other words, knowing that the skater has position W (forward, defence) and that there are X number of skating techniques (e.g., power vs. dynamic for forward, agile vs. aggressive for defenseman) and Y characteristics to measure (e.g., (cross overs, tight turns, direction changes, stride rate, top speed), and knowing that forwards/defensemen Zi have been found as having a skating technique Xi, how are the Y characteristics distributed for the various known forwards/defensemen Z, so that when a new player (either a forward or a defenseman, the one who uses the system presented herein) is measured for Y characteristics, the new skater can be classified more as having a skating technique Xj than a skating technique Xk. This generates a set of confidence measures for each skating technique, for a given new/candidate player.

Based on highest confidence measures, the player will be assigned a skating technique classification associated with their dataset.

Goalie Metrics

| Hybrid Metric | Description | On-Body/Gear Sensor Contribution | Positioning System Contribution |
|---|---|---|---|
| Positioning style | Combine data on how a goalie generates movement on the ice with their position on ice relative to attacking player positions to classify their playing style (aggressive, out of the crease; moves early/moves late; stay at home within the crease). | IMU, Strain Gage and/or Pressure Sensor | Determine goalie's and player's positions on ice from position data |

-continued

| Hybrid Metric | Description | On-Body/Gear Sensor Contribution | Positioning System Contribution |
|---|---|---|---|
| Movement Efficiency | Combine data on how a goalie generates movement on the ice with their measured movement outputs to determine how efficient they are in aligning themselves to the correct position. | IMU, Strain Gage and/or Pressure Sensor | Determine goalie's position on ice and/or change of direction from position data |

The generation of the POSITIONING STYLE metric is now described in further detail by way of example:
  The positioning style hybrid metric (or parameter) may be determined first by classifying the actions of an instrumented goalie into defined hockey specific characteristics (time down, time up, square up, butterfly save, recovery, position in crease).
  Machine Learning algorithms based on sensor data (IMUs, pressure sensors, position data) may be employed to classify the goalie's recorded sessions into frequency of each characteristic defined above, e.g., how often does the goalie portray the aforementioned characteristics or behaviors. This can then be collected over multiple recorded sessions over a selected period of time (game, season) into a distribution of these core characteristics. This can result in a histogram distribution or percentage distribution (if the characteristics are mutually exclusive), for example.
  The distribution of these characteristics are then compared to the characteristics associated with a database of goalies who are pre-defined as having a specific style of play (aggressive, moves early, moves late, stay at home) by expert observers (coaches, trainers). This would be done offline, and stored in a database. In other words, knowing that there are X number of styles and Y characteristics to measure, and knowing that goalies $Z_i$ have a style of play $X_i$, how are the Y characteristics distributed for the various goalies Z, so that when a new goalie (the one who uses the system presented herein) is measured for Y characteristics, the new goalie can be classified more as having a style $X_j$ than a style $X_k$. This generates a set of confidence measures for each style, for a given new/candidate goalie.
  Based on highest confidence measures, the goalie will be assigned a positioning style classification associated with their dataset.

The generation of the MOVEMENT EFFICIENCY metric is now described in further detail by way of example:
  Goalie movement efficiency is related to the input forces of the goalie based on meaningful outcome goals in ice hockey. Minimization of normalized net force (% Body Weight) or physiological factors (VO2/Heart rate) for a hockey specific outcome (Defensive actions, Save percentage) would result in higher goalie movement efficiency.
  Total impulse (F*t) as measured by integration of net force (pressure sensors in skate footbed, or strain gage on the skate) normalized by player weight and divided by distance and time actively spent positioning against the opposing team.
  Goalie motions, detected by AI classifiers (See the POSITIONING STYLE metric above) may be used to calculate an activity score based on total actions performed for a defined time period (one game, complete season, etc.).
  Thereafter, movement efficiency may be classified as "high" or "low", with the following general characteristics:
    High movement efficiency Goalie: Low total impulse, high activity score, lower average heartrate
    Low movement efficiency Goalie: High total impulse, low activity score, higher average heartrate
  Of course, since the space covered by the three aforementioned parameters is three-dimensional, any suitable technique can be used to divide this space into two portions that allow straightforward discrimination between the two levels, including distance metrics, possibly modulated by previously measured baseline values for each parameter.
  A greater number of movement efficiency categories can be devised.

Hockey Metrics

| Hybrid Metric | Description | On-Body/Gear Sensor Contribution | Sensor Positioning System Contribution |
|---|---|---|---|
| Hockey Fitness | Combine data on how hard a player is working (heart rate) with their observed output on the ice to determine their fitness ratio (effort in -vs- observed effort). | Heart Rate | Determine player distance, speed, change of direction, acceleration and/or bursts based on position data |

Generation of the HOCKEY FITNESS hybrid metric is now described in further detail by way of example:
  Hockey fitness can be determined by relating how hard a player is working (measured by or inferred from the heart rate data) and comparing it to observed measures of their work rate, such as player distance, speed, change of direction. This data could be collected over, e.g., a single shift and could be tracked at the shift level as well as average over a period and/or game.
  Heart rate data collected could produce metrics that include:
    an average over a shift (a shift can be determined based on (i) an IMU measuring acceleration player movement or lack thereof and/or (ii) by the position determining system)
    a measure of Heart Rate Variability
    a measure of VO2 max (maximal oxygen uptake, the measurement of the maximum amount of oxygen a person can utilize during intense exercise)

a heart rate recovery score (based on the return of a heart rate to a lower level (e.g., below a predetermined threshold or a threshold customized for that player or a dynamic threshold based on ongoing activity)), a calculation of time spent in each of several "heart rate intensity zones" (calculated based on a percentage of maximum heart rate).

Observed player work rate can be calculated from the positioning system data and include:

player distance and speed change of direction, short accelerations.

The relationship between these observed and calculated metrics from the systems can then be compared to thresholds along multiple variables, or classified in a variety of ways (including based on supervised or unsupervised machine learning) to provide the player insight into their hockey fitness.

For example, the derived hockey fitness metric may fall into three buckets or zones, separated by thresholds:

High fitness→quick heart rate recovery, high VO2 max, lower average HR combined with high speed, longer distance traveled, large number of acceleration bursts, changes in direction, hits.

Average fitness→average heart rate recovery, average VO2 max, median average HR combined with average speed, average distance traveled, average number of acceleration bursts, changes in direction, hits.

Low fitness→limited heart rate recovery, low VO2 max, higher average HR combined with slower speed, less distance traveled, small number of acceleration bursts, changes in direction, hits.

In addition, these levels could differ based on the player's age (which could be an input from the player or from a database based on detected player information such as jersey number) and skill level (which could be an input from the player or that is measured based on observed data, such as accuracy) to provide more relevant insight—vs—a similar population of players.

In addition, if an IMU is also being worn by the player, measures of physical contact (hits) could also be incorporated into the assessment. A larger number of hits would signify a greater level of work rate.

As such, in a non-limiting example, based on a sensor data such as heart rate data, the player's level of physical exertion can be computed (i.e., how hard the player is working). Also, a level of work rate can be computed based on changes in the position data, including not only absolute distance traveled, but also changes in direction and acceleration, i.e., position and derivative position information. In a simple non-limiting expression, a hybrid metric that combines these two inputs (by computing a mathematical relation between the two) produces a measure of hockey fitness, and this measure of hockey fitness can be classified according to the activity of the player (e.g., during a shift, during practice, player age, player gender, time of day).

Of course, any data required for computation may be stored in a database in the memory. This could include data monitored from the sensor data and/or position data and associated with each player, including acceleration bursts, number of hits, distance traveled, heart rate, and any other metric, parameter, or derived element of information mentioned herein above In some embodiments, the terms "quick, high, lower, longer, large, limited, small, slower, and the like" refer to relative quantities compared to other quantities in the data set. In other embodiments, they may represent absolute thresholds in comparison to threshold amounts that are stored in the memory of the computing device or in a database accessible to the computing device. A person of ordinary skill in the art will appreciate that the actual values or thresholds are not material to the computation of these metrics, but rather can be obtained through routine calibration operations, or are inherently computed by a machine learning system in the course of a training phase.

The above are only examples of hybrid metrics and still others can be devised.

Commercial Applications of Hybrid Metrics

The hybrid metrics extracted and computed in the above described ways may be useful in a variety of scenarios. They may be stored in memory 38 and/or encoded into signals that are released onto a data network 68 and used for other purposes. The hybrid metrics may also be presented on a display, which may be part of the computing device 42, or may be implemented separately from the computing device 42. For example, the hybrid metrics may be sent over the data network 68 to a device associated with the player, or to a server that hosts an account for the player, so that the player can access the hybrid metric in real time, or at a later time. Accordingly, another example of a process that can be carried out by the processing entity 54 includes an output process 110 for displaying, outputting, storing, formatting or otherwise processing the extracted hybrid metrics.

Several other examples of using the hybrid metrics are now described.

a. Equipment recommendation

Figure 23:
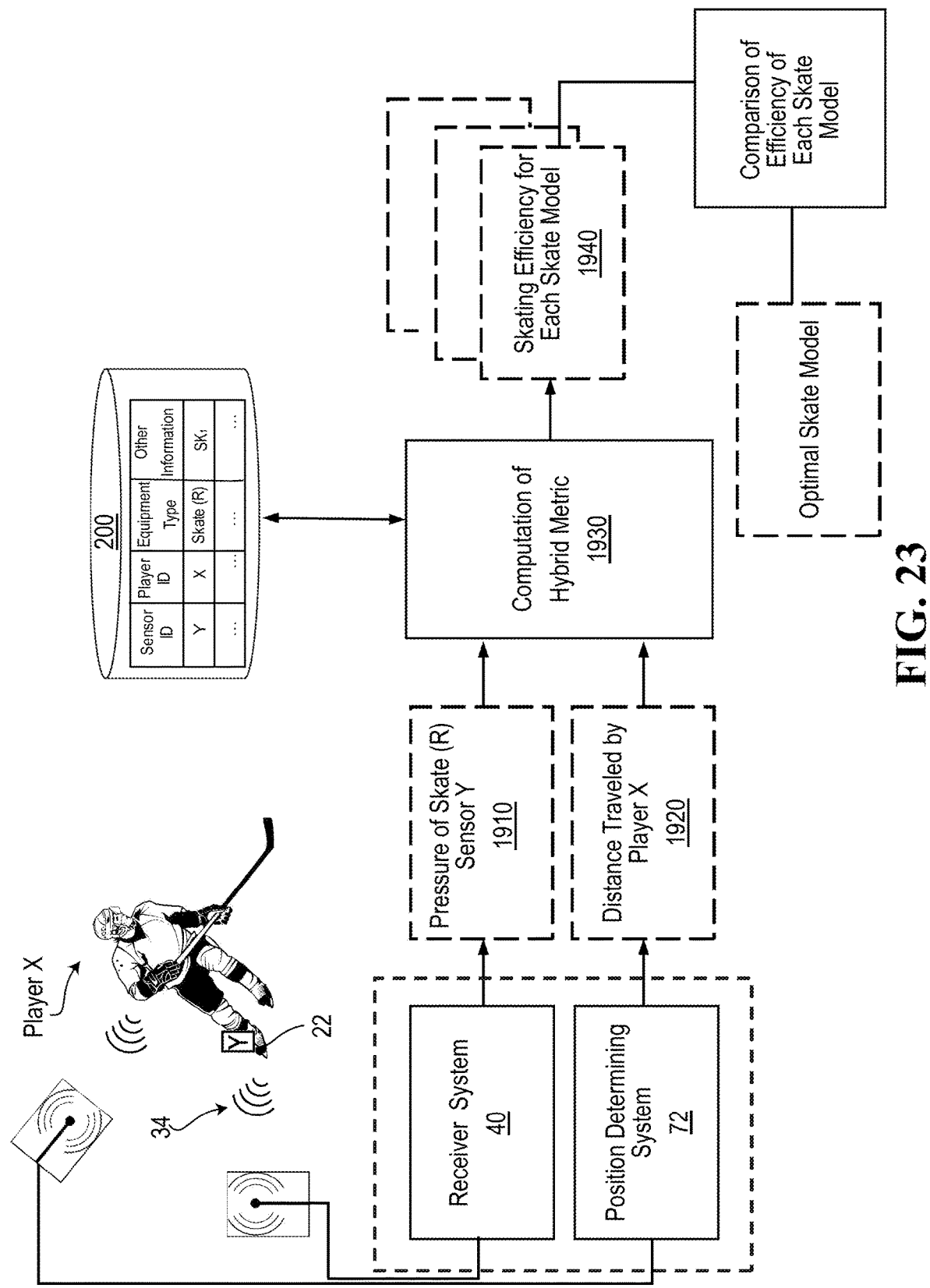

For example, with reference to FIG. 23, the same player can be asked to don multiple different models of skates $SK_1$-$SK_m$ over the course of several games or periods, and a hybrid metric (such as skating efficiency) for a particular skate model $SK_i$ can be determined for each skate model $SK_i$ and stored in the memory 38 of the computing device 42 in association with the particular skate model $SK_i$. As such, the skate model $SK_i$ becomes a variable in the computation of the skating efficiency metric. As part of the output process 110, a comparison is then carried out for the various skate models $SK_1$-$SK_m$, so as to select the skate model $SK_i$ providing the highest skating efficiency (hereinafter the "optimal skate model"). An indication of an optimal skate model $SK_i$ may be conveyed visually on the screen of the computing device 42 or it may be sent by the computing device 42 over the internet to a user account or address associated with the player $14_i$. Alternatively or in addition, the skating efficiency associated with a particular skate model $SK_i$ can be provided as feedback to the manufacturer of the skate, and the manufacturer can make tweaks to the skate design, and compare the skating efficiency of the new design.

In other cases analogous to the above example pertaining to skate models, certain metrics (such as shot accuracy) could be used to assess which stick is most suitable for the player $14_i$ during either game action or during a training scenario.

b. Feedback and comparison

Figure 24:
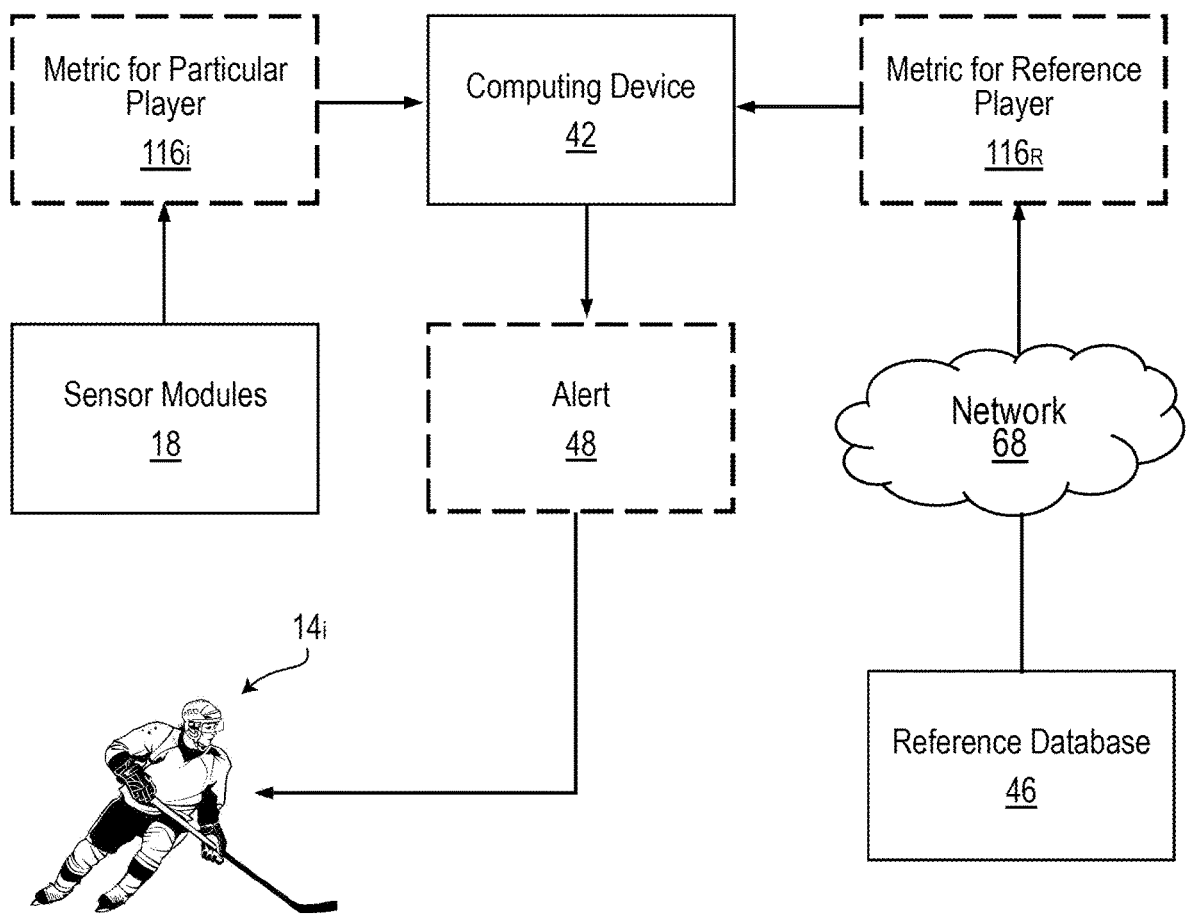
FIG. 24 is a block diagram conceptually illustrating a feedback provided to a player, in accordance with a non-limiting embodiment.

In still other instantiations of the output process 110, metrics could provide feedback on the evolution of the player's fitness, technique, etc. throughout the course of a season, noting and indicating areas where improvements have been made or are needed, when compared to metrics from teammates, peers or professional players. To this end, and with reference to FIG. 24, the computing device 42 may store a given metric $116_i$ in association with a particular player $14_i$. The computing device 42 may also store a corresponding metric $116_R$ associated with a reference player. For example, the particular player $14_i$ may provide an indication of a reference player (such as a pro) against whom the particular player $14_i$ wishes to measure himself. The metric $116_R$ associated with the pro may be obtained from a reference database 46 over a data network 68 (e.g., the internet). The computing device 42 may then carry out a comparison process that compares the particular player's metrics $116_i$ against the reference player's metrics $116_R$. At this point, if the computing device 42 determines that two metrics $116_i$, $116_R$ being compared are closer to each other than a first threshold or further from one another than a second threshold, the computing device 42 may signal this occurrence to the particular player $14_i$ in the form of an alert 48 (e.g. an audible alert, email or other form of message). The first and second thresholds may be adjustable by the particular player $14_i$. In some cases, a single threshold may be used and in other cases, more than two thresholds are used. In some cases, multiple metrics may be compared between the particular player $14_i$ and the reference player, and a distance between respective pairs of metrics may be calculated and integrated into an overall distance between the particular player $14_i$ and the reference player and displayed and/or stored in memory 38 and/or embedded in a signal communicated over the internet.

c. Segmentation

Those skilled in the art can also appreciate that another instantiation of the output process 110 may be the computation of segmented metrics 120. Specifically, the position data 90 may can provide context for segmenting the raw sensor data 32. This leads to the computation of context-dependent metrics 122 that could be useful as feedback for improving individual or team performance.

For example, consider an algorithm that processes the raw sensor data 32 and the position data 90 to determine which of the plurality of players $14_1$-$14_P$ has the puck at any given time. It may thus be of interest to segment the raw sensor data 32 regarding various players' heart rates, so as to determine, for each given player, what is that player's heart rate when he had possession of the puck (and when he did not). This information may be stored in a central database for the player $14_i$ or for a team. Other factors may be stored in association with the segmented information, such as time of day, day of week, age, etc.

In another example, consider an algorithm that processes the raw sensor data 32 and the position data 90 to determine which of the plurality of players $14_1$-$14_P$ are playing offense and which of the plurality of players $14_1$-$14_P$ are playing defense. It may thus be of interest to segment the raw sensor data 32 regarding various players' power generation (collected from, e.g., pressure sensors, as described earlier), so as to determine, for each given player $14_i$, what is that player's power generation when he was playing offense versus when he was playing defense. This information may be stored in a central database for the player or for a team.

Segmentation can be performed in an almost limitless fashion, based on sport-specific variables such as the player's stance, whether the player $14_i$ is skating forwards or backwards, whether the player is on the ice or on the bench, whether the player has possession of the puck, etc. Other variables may segment the data at the team level, such as whether a team is short-handed or on the power play, which team or player has possession of the puck, etc. Still other variables are independent of the sport, such as day of the week, age, gender, etc.

All segmented data 124 may be fed to the player as a stream, such as a daily or weekly update in the form of a text message or email message.

d. Ice time monitoring

Another instantiation of the output process 110 comprises determining ice time of individual players $14_i$ (from, e.g., the shift length metric) and sending an alert to parents when the ice time for their child reaches or falls below a certain level/percentage/average. The shift length metric for a particular player $14_i$ may be a metric calculated from multiple sensors with or without any position data 90. For example, by taking into consideration (i) whether the skate is moving and (ii) whether the heart rate is indicative of not being at rest. If both conditions are met, a conclusion is reached that the player is on a shift.

e. Centralized platform

Another instantiation of the output process 110 comprises providing a centralized platform for storing the hybrid metrics associated with the player $14_i$, and with various other players $14_1$-$14_P$. This information can be uploaded to the centralized platform from the computing device 42 (which could be the player's smartphone) and may be shared with other players $14_1$-$14_P$ according to parameters/rules set by the player. Other elements of the centralized platform may include each player's past hockey experiences and statistics, links to videos and testimonials. The app provides an ability to upload collected metrics and statistics automatically as they are generated.

Optical Markers

In the context of a camera-based position determining system 82, in order to facilitate the successful extraction of position data 90 of players $14_1$-$14_P$ and their equipment 30, especially from low-quality video feeds, optical markers 126 may be placed on the players' equipment 30 that is externally visible. Optical markers 126 may be passive or active. A non-limiting example of a passive optical marker is a material that is colored or reflective in nature. A non-limiting example of an active optical marker is a battery-powered LED.

Figure 25:
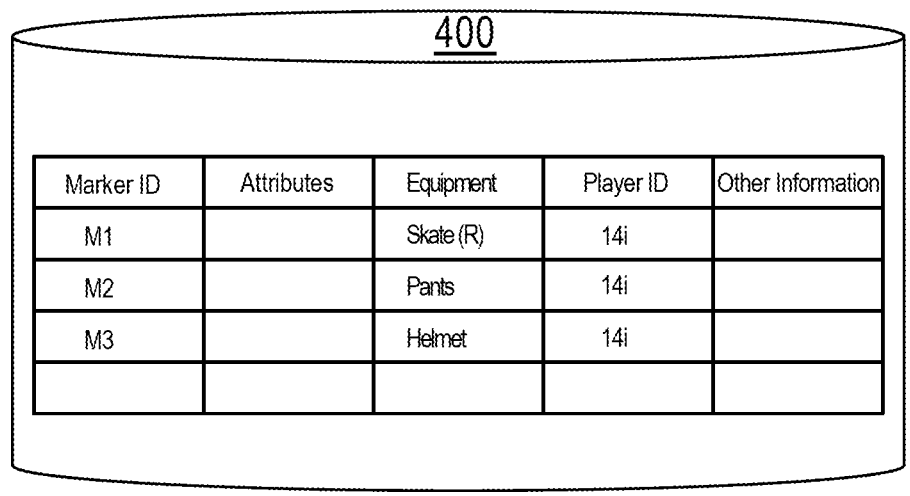
FIG. 25 shows a non-limiting example of markers placed on sports equipment and a corresponding database storing marker information.
Figure 25:
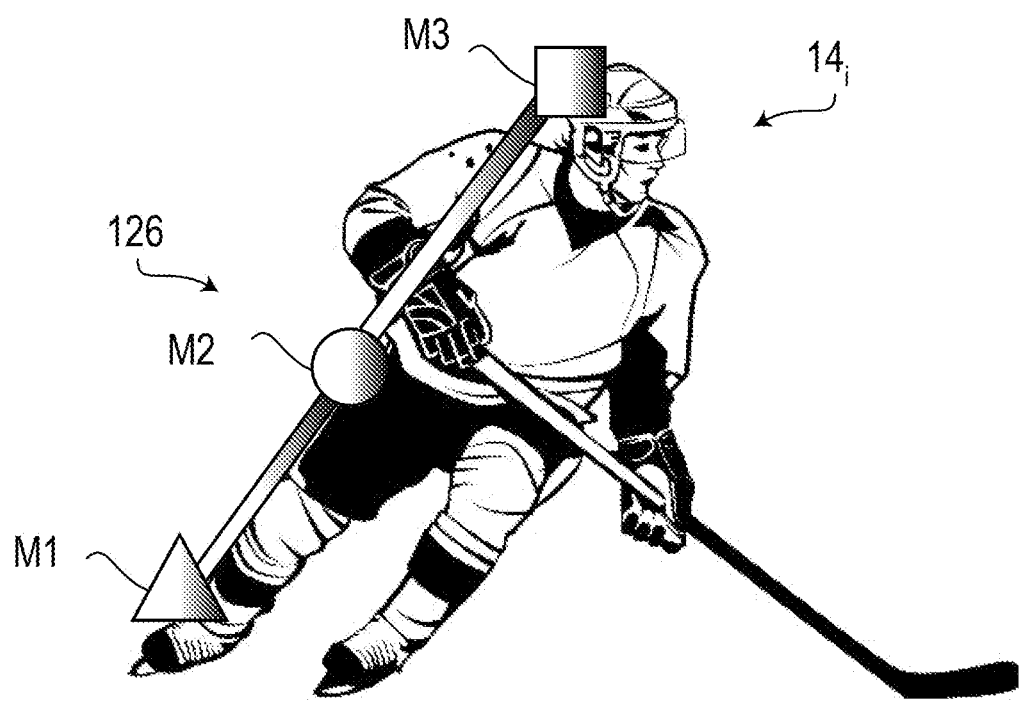

In accordance with an embodiment, and with reference to FIG. 25, the markers 126 are strategically positioned on the equipment/apparel 30 (e.g., jersey, shorts, helmet, stick, skate, goalie pad and glove). Moreover, markers 126 of different types, sizes, shapes, colors, etc. may be used for different equipment/apparel types. For example, a band of material of a first color may be placed around the cuff of a player's glove, and a pattern of material of a second color may be placed on one or more areas of the player's helmet. The markers 126 can include reflective or high-contrast dots in strategic/predetermined locations on the equipment.

Figure 4:
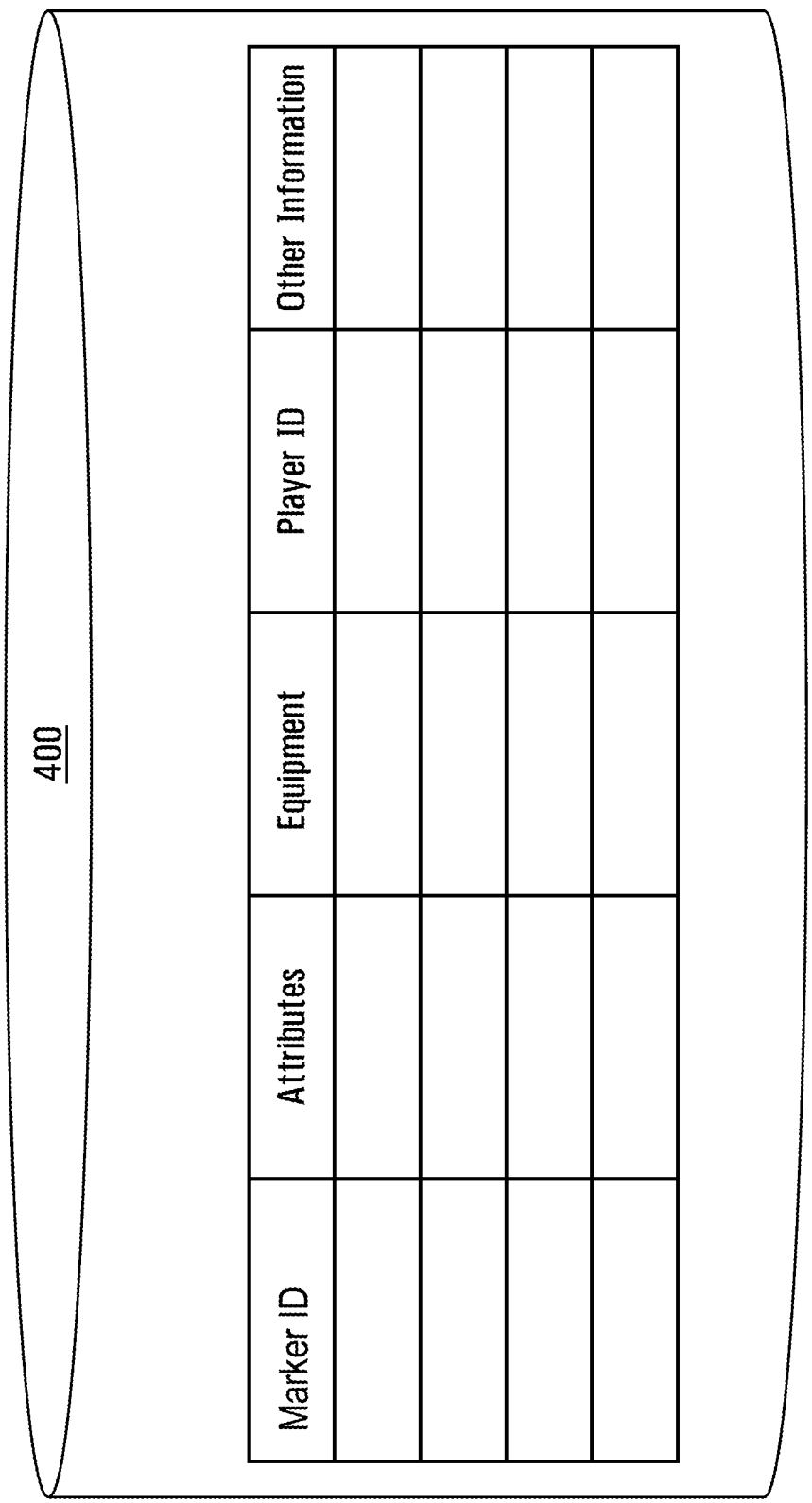
FIG. 4 illustrates a non-limiting example of a database storing marker information.

The respective colors, patterns and configurations of the markers 126, together with the equipment 30 on which they are placed, are known a priori and may be stored in a marker database. By way of non-limiting example, FIG. 4 shows the contexts of the marker database 400 in the form of a table stored in a non-transitory medium. Of course, a table is merely used as an example. The table includes a plurality of rows, one associated with each marker. The table also includes a plurality of columns, each corresponding to a field for each row. Examples of such fields may include the following, with the understanding that some fields (such as "Player" may initially be empty):

ID: a unique identifier (ID) of the marker.

Attributes: characteristics of the marker such as color, pattern, size, configuration, etc.

Equipment: the type of equipment or apparel on which the marker has been placed (e.g., jersey, shorts, helmet, stick, skate, goalie pad, glove).

Player: a unique ID (e.g., name or team+number) of the player who wears or uses the equipment containing the marker.

Other information, such as marker type (active vs. passive).

The use of optical markers 126 may facilitate the accuracy with which context can be extracted from camera-captured data 78, and then this context is used to improve accuracy some of the hybrid metrics referred to above.

For example, consider the case (e.g., in FIG. 25) where there is a first marker M1 on a player's skate, a second marker M2 on the player's pants and a third marker M3 on the player's helmet. Assume now that it is known a priori the type of equipment associated with each optical marker 126, and that it is known a priori that all three markers are associated with the same player $14_i$. Then, consider that one wishes to know the "skating direction" of the player $14_i$, i.e., whether the player $14_i$ is skating forward or backward, or is not skating at all. This contextual information may then be combined with raw sensor data 32 to make the "skating efficiency" more meaningful, as different ranges of values may be expected depending on the skating direction. The skating direction may be obtained from the relative position of the markers, without the expense of advanced video processing to recognize body parts or fast moving limbs. Specifically, the angle M1-M2-M3 can be determined as a value, and a discrimination function applied to select into which of three ranges (forward skating vs backwards skating vs not skating) the value falls. The ranges for the three possibilities could be pre-determined based on known data about the head-waist-foot angle for hockey skating, or through machine learning. This is made possible because of the prior knowledge of which piece of equipment 30 is associated with which marker 126. In other words, the ability to recognize not only a marker 126, but to pinpoint a type of equipment 30 based on a unique marker configuration, can be useful in numerous situations.

Another example where an optical marker 126 may be useful is to allow faster and/or more accurate creation of a 3D model from 2D images obtained from different video feeds taken at different angles yet containing the same optical marker 126.

Those skilled in the art will appreciate that in some cases, equipment 3—may be provided with both a sensor module 18 and a passive or active optical marker 126.

The use of optical markers 126 to assist in determining parameters (such as the "skating direction" above) based on camera-captured data 78 may be particularly advantageous in the case of amateur/home video, as shot by cameras on mobile phones used at recreational or college hockey games. This is because the quality of the video feeds produced by such devices may be low, due to the limitations of the camera (e.g., low frame rate, small aperture), the venue (e.g., low lighting) and the videographer (e.g., jitter, distance to subject, rapid panning).

Portable Localization System

Figure 26:
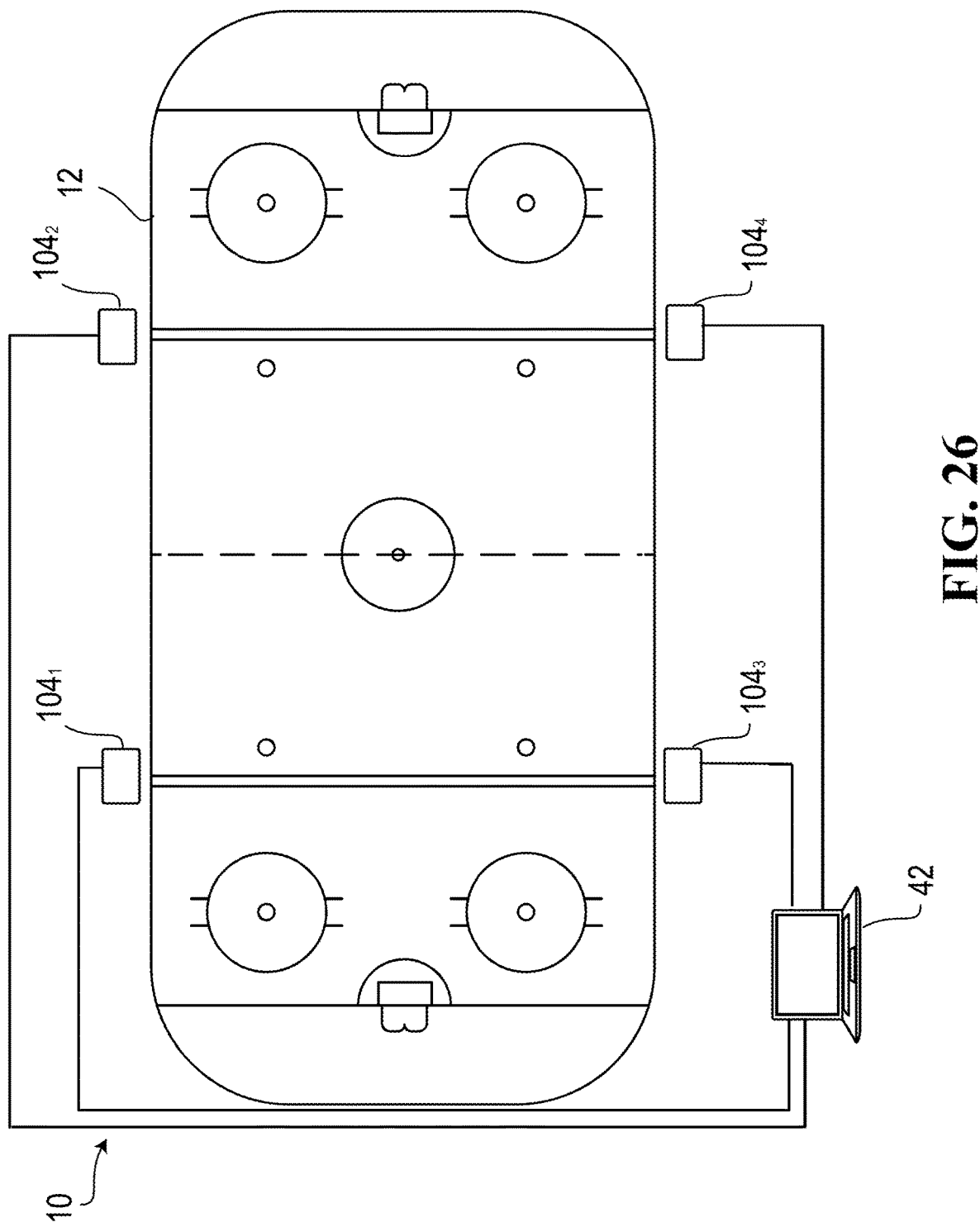
FIG. 26 shows a configuration of a calibration-less localization system, in accordance with a non-limiting embodiment.

With reference to FIG. 26, the following describes a portable, calibration-less localization system, in accordance with a non-limiting embodiment. In an example, a plurality of beacons $104_1$-$104_B$ may be provided. The beacons $104_1$-$104_B$ communicate with the computing device 42, which runs a position determining program or application 106 specific to the beacons $104_1$-$104_B$.

In one embodiment, the beacons $104_1$-$104_B$ are compatible with the sensor modules 18 and can receive the transmissions from the sensor modules 18; in fact, the beacons $104_1$-$104_B$ may implement the functionality of the receiver system 40. In another embodiment, the beacons $104_1$-$104_B$ are configured to receive transmissions from specific tags 76 or emitters worn by players $14_1$-$14_P$ or attached to articles of equipment 30 associated with players $14_1$-$14_P$.

The beacons $104_1$-$104_B$ are designed to be installed at specific points of the ice hockey surface 12 based on standardized playing surface markers (e.g., lines such as blue line, center line, goal line, or face-off circles). There are two standard sizes for hockey rinks: one used primarily in North America, also known as NHL size, the other used in Europe and international competitions, also known as IIHF or Olympic size. The length and width of the rink, as well as the relative distances between the various lines and the relative positions of the face-off circles, are standardized for each of the two types of rinks.

In accordance with an embodiment, a kit 36 may be provided which includes a set of beacons $104_1$-$104_E$ together with instructions for placing those beacons $104_1$-$104_B$ at specific pre-determined points of the ice hockey rink. For example, four beacons (for example, $104_1$, $104_2$, $104_3$ and $104_4$) may be provided, each to be placed on the boards in alignment with one of the extremities of one of the blue lines. In other kits 36, six or eight beacons may be provided, in alignment with other pre-determined points of the ice hockey rink (e.g., icing line, etc.).

The manner in which the beacons $104_1$-$104_B$ are placed may be by way of attachment to the boards by suction cups or hanging in a saddle that is placed over the top rail of the boards. A certain height distance from the ice may be—pre-specified (e.g., 3 feet). Other configurations are of course possible.

With reference to the flowchart in FIG. 27, once the beacons $104_1$-$104_B$ are placed, and the position determining program 106 is run on the computing device 42, the program 106 may be configured to prompt a user for an ice surface size (block 2710), which may be selected from several options, including one or more of NHL, IIHL, other or custom, for example. Based on the selection, the dimensions of the ice surface 12 will be known. In addition, at block 2720 the user may be prompted to confirm the placement of the beacons (e.g., "Please confirm all 4 beacons placed at blue line at the appropriate height"). In a variant, there is no prompting of the user at block 2710 and/or block 2720, but instead an assumption is made that the user has complied with the installation instructions. In still other variants, there may be a choice of beacon configurations, namely 4 or 6 beacons, at which pre-determined positions to set them etc.

Furthermore, once the program 106 obtains the known positions of the beacons relative to the ice surface 12 of known dimensions, the position determining program processes the received signals and determines the positions of the players or articles of equipment containing the tags and/or sensors (step 2730). The computing device 42 adjusts the measurements it receives from the beacons (e.g., transmissions received from the tags and/or sensors) based on the pre-determined positions of the ice hockey surface 12 of known dimensions being occupied by the beacons. This allows relatively accurate position determination to take place without the need for a calibration step or other calibration actions by the user, other than simply selecting the type of ice surface 12 (or not, in the case the program defaults to the correct default ice surface 12).

Of course, a similar concept may be applied to other sporting events having regulation-size surfaces, such as football, tennis, etc., which allows the transportation of portable beacons without the need for calibration, as long as they are positioned at certain positions associated with pre-determined markers known to be associated with the playing surface.

Various examples of articles of sports equipment will be described below. These articles of sports equipment may be equipped with or include one or more sensors, tags, microprocessors and/or wireless transmitters (beacons) to aid in tracking of the sensor data and the position data. The sensors, tags, microprocessors and/or wireless transmitters may be affixed onto the equipment in various ways, such as by gluing or by placement int a specially designed pod or pocket. The articles of sports equipment may also include optical markers to support visual tracking.

Helmets

In yet another specific non-limiting example of implementation, the article of sports equipment is a helmet, e.g., a hockey helmet. FIGS. 6A to 7B show embodiments of helmets to which specific non-limiting examples of implementation may be applied.

FIGS. 6A to 6H show embodiments of a helmet 1610 for protecting a user's head. In this embodiment, the helmet 1610 is an athletic helmet for protecting the head of the user who is engaging in a sport or other athletic activity against impacts. More particularly, in this embodiment, the helmet 1610 is a hockey helmet for protecting the head of the user, who is a hockey player, against impacts (e.g., from a puck or ball, a hockey stick, a board, ice or another playing surface, etc., with another player, etc.).

The helmet 1610 comprises an outer shell 1611 and a liner 1615 to protect the player's head. In this example, the helmet 1610 also comprises a chinstrap 1616 for securing the helmet 1610 to the player's head. The helmet 1610 may also comprise a faceguard 1614 to protect at least part of the player's face (e.g., a grid (sometimes referred to as a "cage") and a chin cup 16112 or a visor (sometimes referred to as a "shield")).

The helmet 1610 defines a cavity 1613 for receiving the player's head. In response to an impact, the helmet 1610 absorbs energy from the impact to protect the player's head. The helmet 1610 protects various regions of the player's head. The player's head comprises a front region FR, a top region TR, left and right side regions LS, RS, a back region BR, and an occipital region OR. The front region FR includes a forehead and a front top part of the player's head and generally corresponds to a frontal bone region of the player's head. The left and right side regions LS, RS are approximately located above the player's ears. The back region BR is opposite the front region FR and includes a rear upper part of the player's head. The occipital region OR substantially corresponds to a region around and under the head's occipital protuberance.

The helmet 1610 comprises an external surface 1618 and an internal surface 1620 that contacts the player's head when the helmet 1610 is worn. The helmet 1610 has a front-back axis FBA, a left-right axis LRA, and a vertical axis VA which are respectively generally parallel to a dorsoventral axis, a dextrosinistral axis, and a cephalocaudal axis of the player when the helmet 1610 is worn and which respectively define a front-back direction, a lateral direction, and a vertical direction of the helmet 1610. Since they are generally oriented longitudinally and transversally of the helmet 1610, the front-back axis FBA and the left-right axis LRA can also be referred to as a longitudinal axis and a transversal axis, respectively, while the front-back direction and the lateral direction can also be referred to a longitudinal direction and a transversal direction, respectfully.

The outer shell 1611 provides strength and rigidity to the helmet 1610. To that end, the outer shell 1611 typically comprises a rigid material 1627. For example, in various embodiments, the rigid material 27 of the outer shell 1611 may be a thermoplastic material such as polyethylene (PE), polyamide (nylon), or polycarbonate, a thermosetting resin, or any other suitable material. The outer shell 1611 includes an inner surface 1617 facing the inner liner 1615 and an outer surface 1619 opposite the inner surface 1617. The outer surface 1619 of the outer shell 1611 constitutes at least part of the external surface 1618 of the helmet 1610.

In this embodiment, the outer shell 1611 comprises shell members 1622, 1624 that are connected to one another. In this example, the shell member 1622 comprises a top portion 1621 for facing at least part of the top region TR of the player's head, a front portion 1623 for facing at least part of the front region FR of the player's head, and left and right lateral side portions 1625L, 1625R extending rearwardly from the front portion 1623 for facing at least part of the left and right side regions LS, RS of the player's head, respectively. The shell member 1624 comprises a top portion 1629 for facing at least part of the top region TR of the player's head, a back portion 1631 for facing at least part of the back region BR of the player's head, an occipital portion 1633 for facing at least part of the occipital region OR of the player's head, and left and right lateral side portions 1635L, 1635R extending forwardly from the back portion 1631 for facing at least part of the left and right side regions LS, RS of the player's head, respectively.

In this embodiment, the helmet 1610 is adjustable to adjust how it fits on the player's head. To that end, the helmet 1610 comprises an adjustment mechanism 1640 for adjusting a fit of the helmet 1610 on the player's head. The adjustment mechanism 1640 may allow the fit of the helmet 1610 to be adjusted by adjusting one or more internal dimensions of the cavity 1613 of the helmet 1610, such as a front-back internal dimension FBD of the cavity 1613 in the front-back direction of the helmet 1610 and/or a left-right internal dimension LRD of the cavity 1613 in the left-right direction of the helmet 1610.

More particularly, in this embodiment, the adjustment mechanism 1640 is configured such that the outer shell 1611 and the inner liner 1615 are adjustable to adjust the fit of the helmet 1610 on the player's head. To that end, in this embodiment, the shell members 1622, 1624 are movable relative to one another to adjust the fit of the helmet 1610 on the player's head. In this example, relative movement of the shell members 1622, 1624 for adjustment purposes is in the front-back direction of the helmet 1610 such that the front-back internal dimension FBD of the cavity 1613 of the helmet 1610 is adjusted. The shell member 1624 may be movable relative to the shell member 1622 from a first position, which corresponds to a minimum size of the helmet 1610, to a second position, which corresponds to an intermediate size of the helmet 1610, and to a third position, which corresponds to a maximum size of the helmet 1610.

In this example of implementation, the adjustment mechanism 1640 comprises an actuator 1641 that can be moved (in this case pivoted) by the player between a locked position, in which the actuator 1641 engages a locking part 1645 of the shell member 1622 and thereby locks the shell members 1622, 1624 relative to one another, and a release position, in which the actuator 1641 is disengaged from the locking part 1645 of the shell member 1622 and thereby permits the shell members 1622, 1624 to move relative to one another so as to adjust the size of the helmet 1610. The adjustment mechanism 1640 may be implemented in any other suitably way in other embodiments.

The liner 1615 is disposed between the outer shell 1611 and the player's head to absorb impact energy when the helmet 1610 is impacted. More particularly, the liner 1615 comprises an outer surface 1638 facing towards the outer shell 1611 and an inner surface 34 facing towards the player's head. For example, in some embodiments, the inner liner 1615 may comprise a shock-absorbing material. For instance, in some cases, the shock-absorbing material may include a polymeric foam (e.g., expanded polypropylene (EPP) foam, expanded polyethylene (EPE) foam, expanded polymeric microspheres (e.g., Expancel™ microspheres commercialized by Akzo Nobel), or any other suitable polymeric foam material). Any other material with suitable impact energy absorption may be used in other embodiments. Additionally or alternatively, in some embodiments, the inner liner 1615 may comprise an array of shock absorbers that are configured to deform when the helmet 1610 is impacted. For instance, in some cases, the array of shock absorbers may include an array of compressible cells that can compress when the helmet 1610 is impacted. Examples of this are described in U.S. Pat. No. 7,677,538 and U.S. Patent Application Publication 2010/0258988, which are incorporated by reference herein.

The liner 1615 may be connected to the outer shell 1611 in any suitable way. For example, in some embodiments, the inner liner 1615 may be fastened to the outer shell 1611 by one or more fasteners such as mechanical fasteners (e.g., tacks, staples, rivets, screws, stitches, etc.), an adhesive, or any other suitable fastener.

In this embodiment, the liner 1615 comprises a plurality of pads $1636_1$-$1636_4$, $1637_1$-$1637_C$ disposed between the outer shell 1611 and the player's head when the helmet 1610 is worn. In this example, respective ones of the pads $1636_1$-$1636_4$, $1637_1$-$1637_C$ are movable relative to one another and with the shell members 1622, 1624 to allow adjustment of the fit of the helmet 1610 using the adjustment mechanism 1640.

In this example, the pads $1636_1$-$1636_4$ are responsible for absorbing at least a bulk of the impact energy transmitted to the inner liner 1615 when the helmet 1610 is impacted and can therefore be referred to as "absorption" pads. In this embodiment, the pad $1636_1$ is for facing at least part of the front region FR and left side region LS of the player's head, the pad $1636_2$ is for facing at least part of the front region FR and right side region RS of the player's head, the pad $1636_3$ is for facing at least part of the back region BR and left side region LS of the player's head, the pad $1636_4$ is for facing at least part of the back region BR and right side region RS of the player's head. Another pad is for facing at least part of the top region TR and back region BR of the player's head. The shell member 1622 overlays the pads $1636_1$, $1636_2$ while the shell member 1624 overlays the pads $1636_3$, $1636_4$.

In this embodiment, the pads $1637_1$-$1637_C$ are responsible to provide comfort to the player's head and can therefore be referred to as "comfort" pads. The comfort pads $1637_1$-$1637_C$ may comprise any suitable soft material providing comfort to the player. For example, in some embodiments, the comfort pads $1637_1$-$1637_C$ may comprise polymeric foam such as polyvinyl chloride (PVC) foam, polyurethane foam (e.g., PORON XRD™ foam commercialized by Rogers Corporation), vinyl nitrile foam or any other suitable polymeric foam material. In some embodiments, given ones of the comfort pads $1637_1$-$1637_C$ may be secured (e.g., adhered, fastened, etc.) to respective ones of the absorption pads $1636_1$-$1636_4$. In other embodiments, given ones of the comfort pads $1637_1$-$1637_C$ may be mounted such that they are movable relative to the absorption pads $1636_1$-$1636_4$. For example, in some embodiments, one or more of the comfort pads $1637_1$-$1637_C$ may be part of a floating liner as described in U.S. Patent Application Publication 2013/0025032, which, for instance, may be implemented as the SUSPEND-TECH™ liner member found in the BAUER™ RE-AKT™ and RE-AKT 100™ helmets made available by Bauer Hockey, Inc. The comfort pads $1637_1$-$1637_C$ may assist in absorption of energy from impacts, in particular, low-energy impacts.

Although in embodiments considered above the article that is a helmet is a hockey player, in other embodiments, the article may be any other helmet usable by a player playing another type of contact sport (e.g., a "full-contact" sport) in which there are significant impact forces on the player due to player-to-player and/or player-to-object contact or any other type of sports, including athletic activities other than contact sports.

For example, in other embodiments, the article may be a hockey goalkeeper helmet.

Figure 7A:
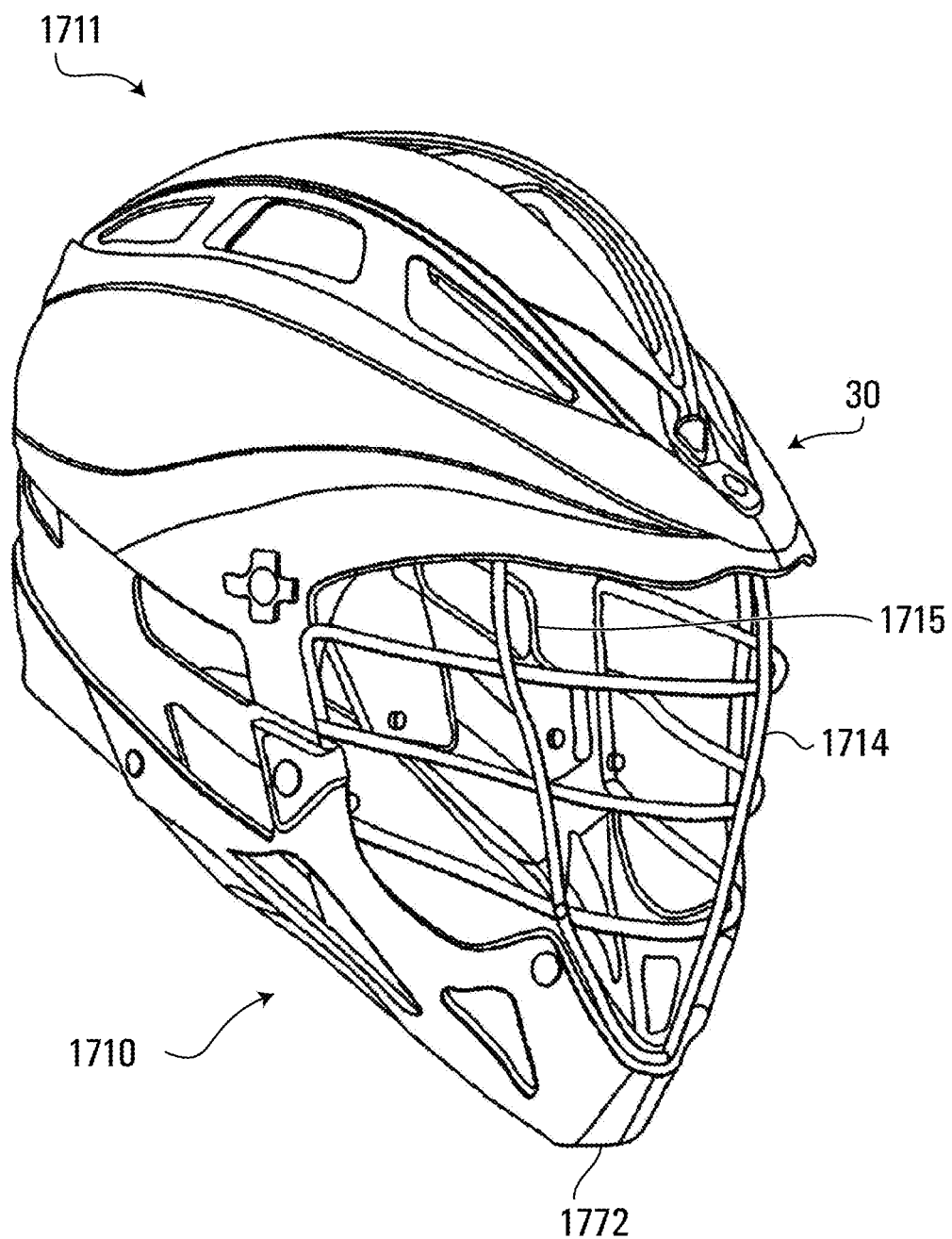
Figure 7B:
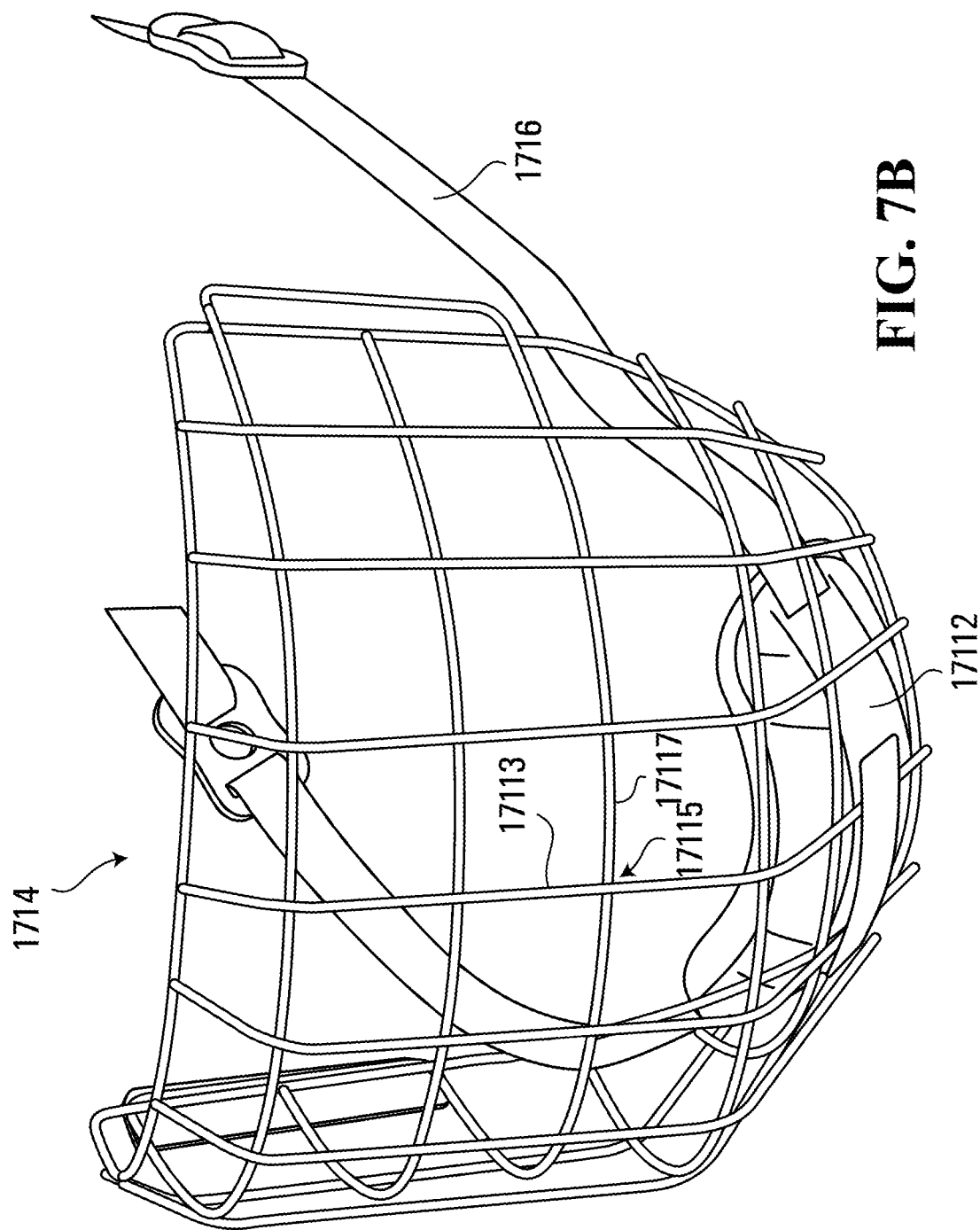

As another example, as shown in FIGS. 7A and 7B, in other embodiments, the article may be a lacrosse helmet 1710. The lacrosse helmet 1710 comprises a chin piece 1772 extending from the left lateral side portion 1725L to the right lateral side portion 1725R of the helmet 1710 and configured to extend in front of a chin area of the user. The lacrosse helmet also comprises the faceguard 1714 which is connected to the shell 1711 and the chin piece 1772.

In other embodiments, the article may be a baseball/softball helmet or any other type of helmet.

Protective

Figure 8:
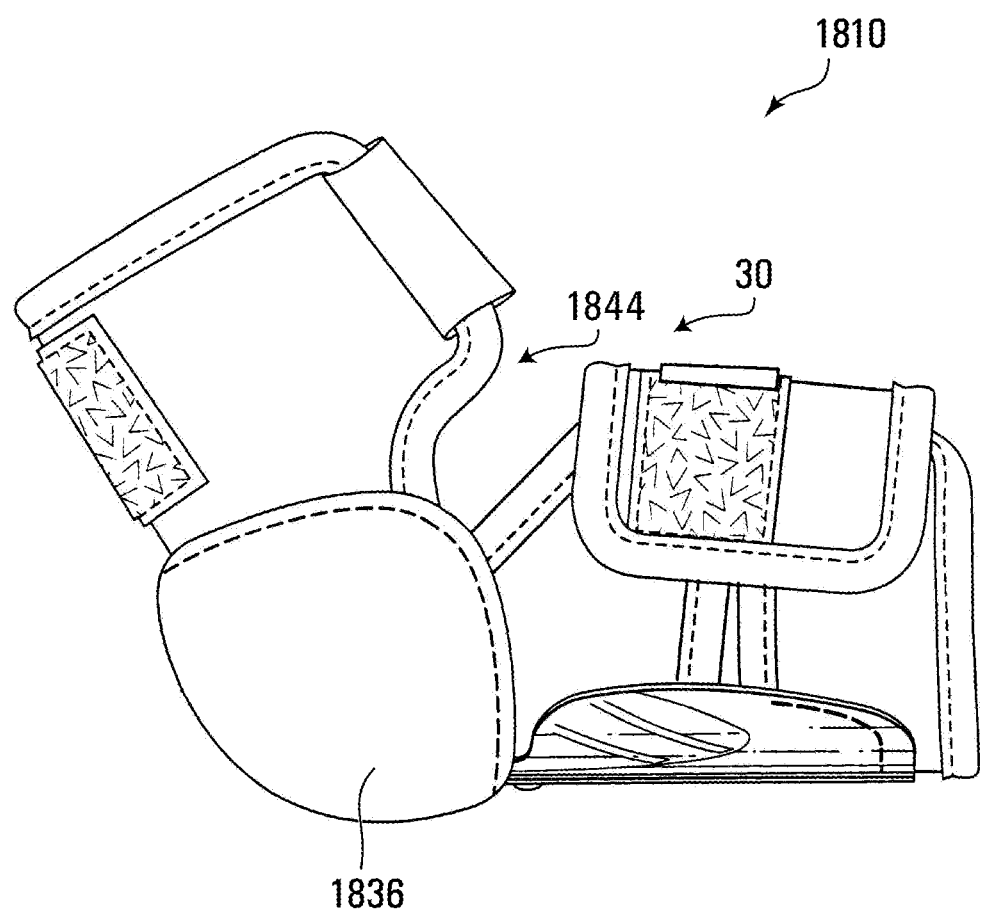
Figure 9:
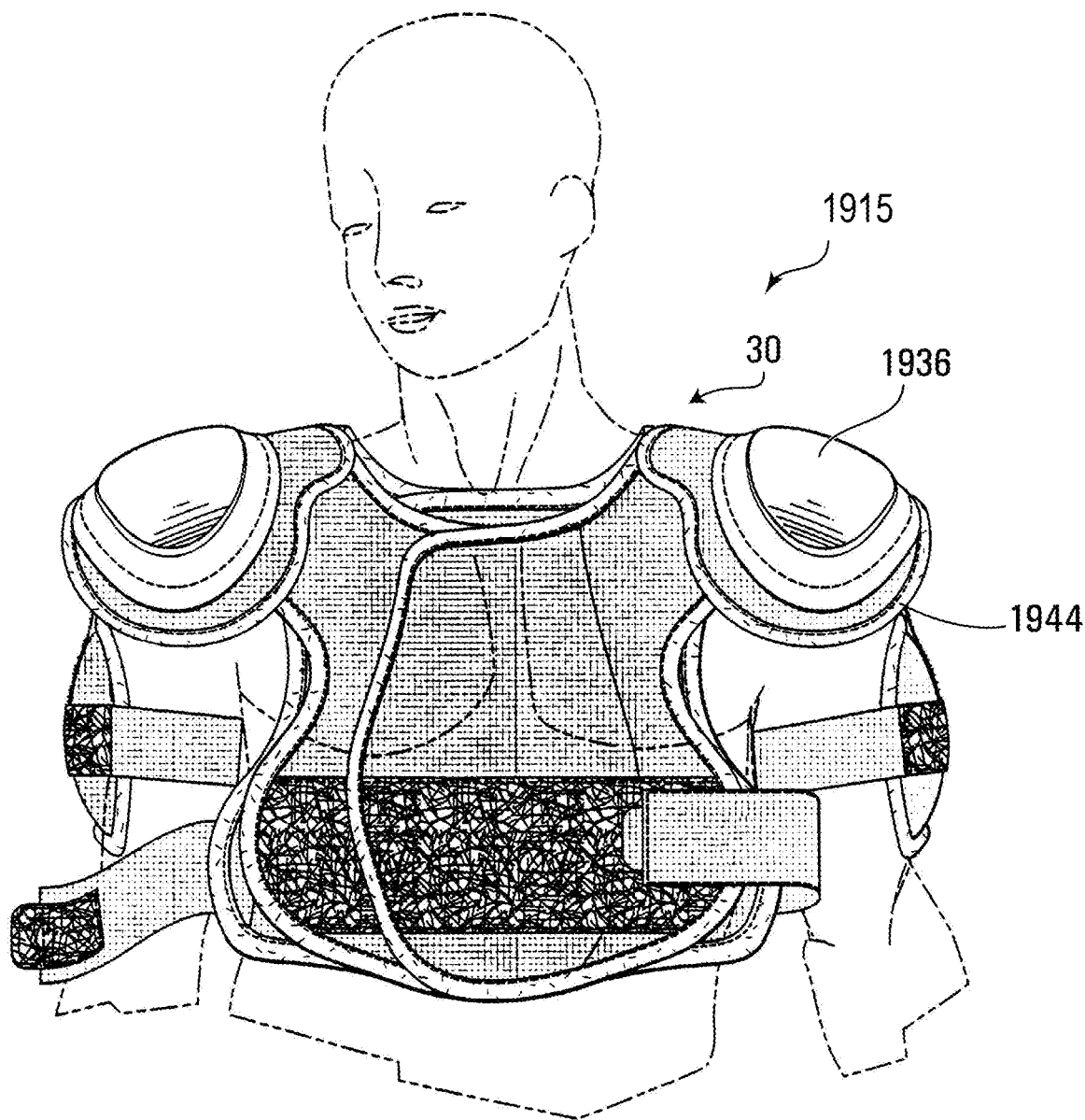
Figure 10:
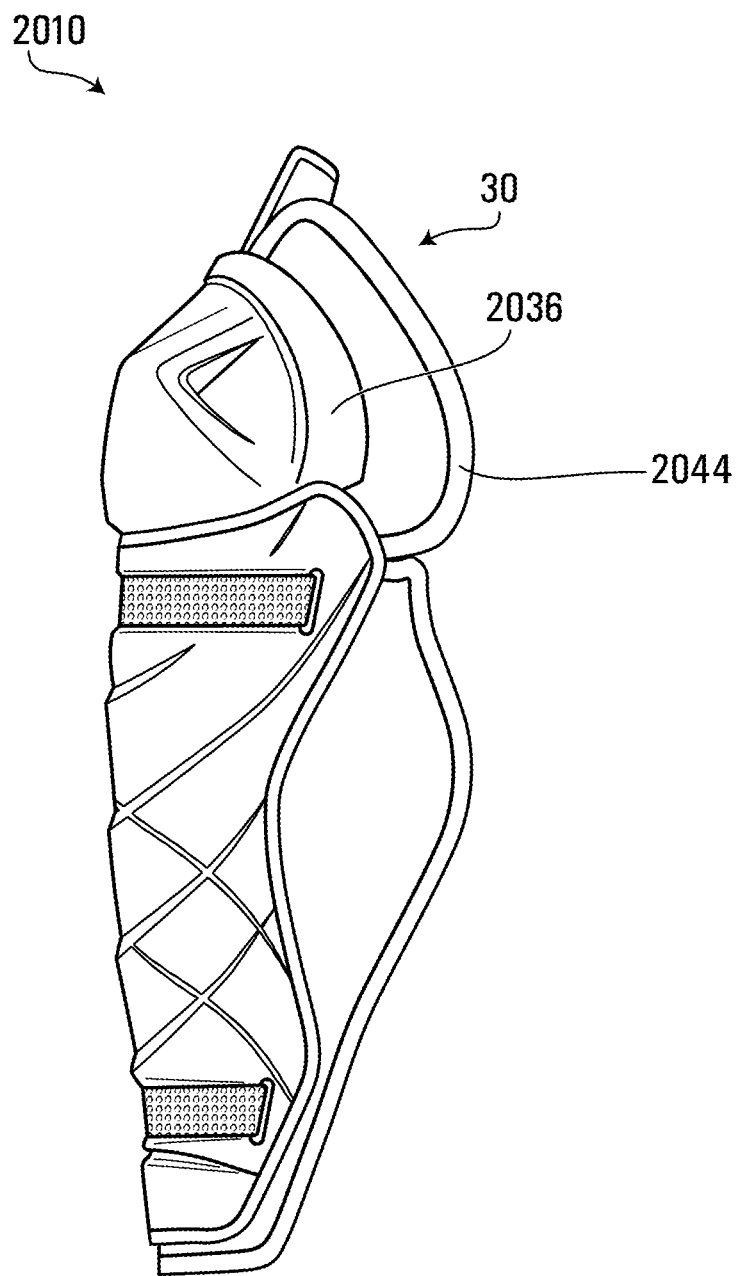
Figure 11:
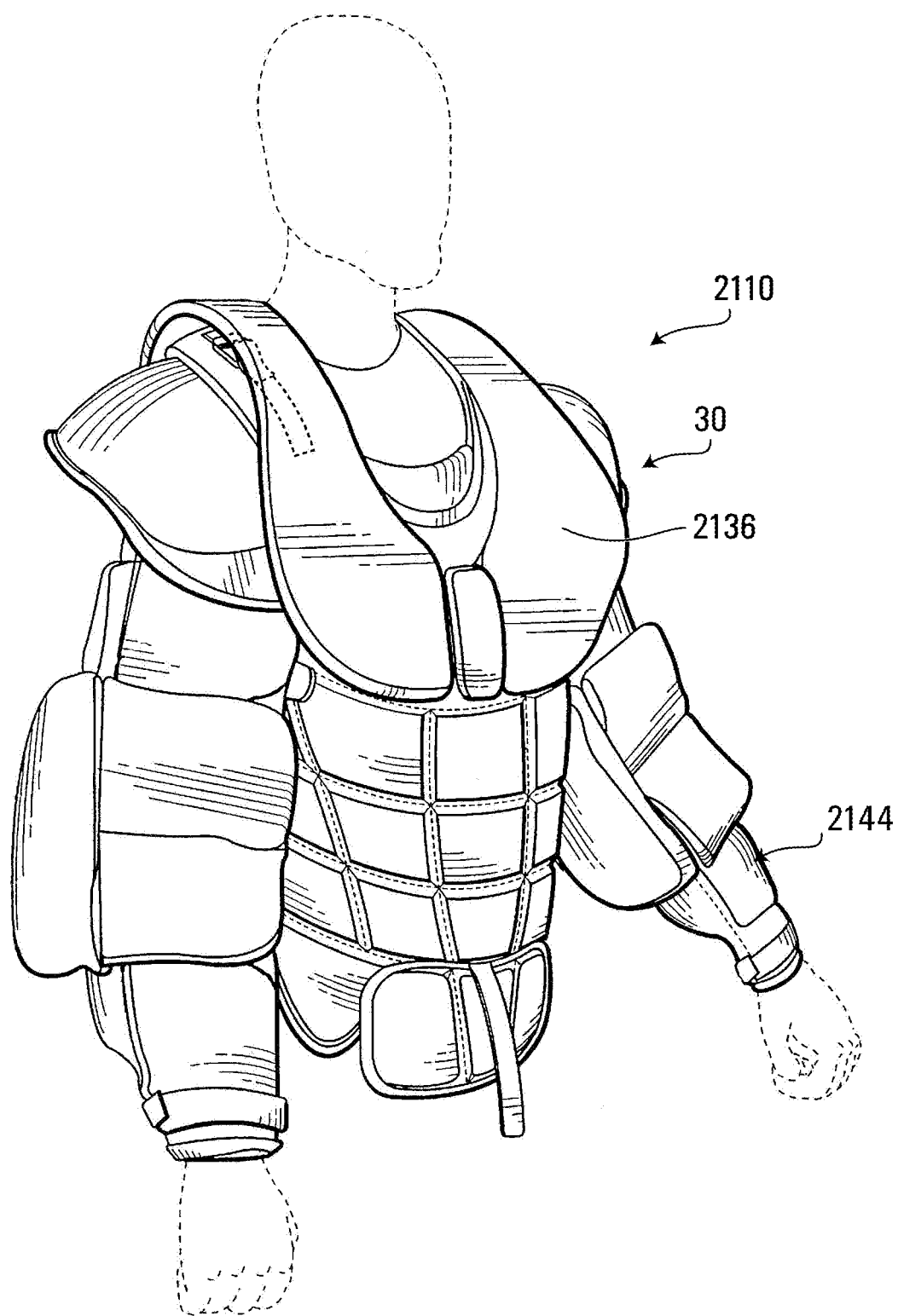
Figure 12:
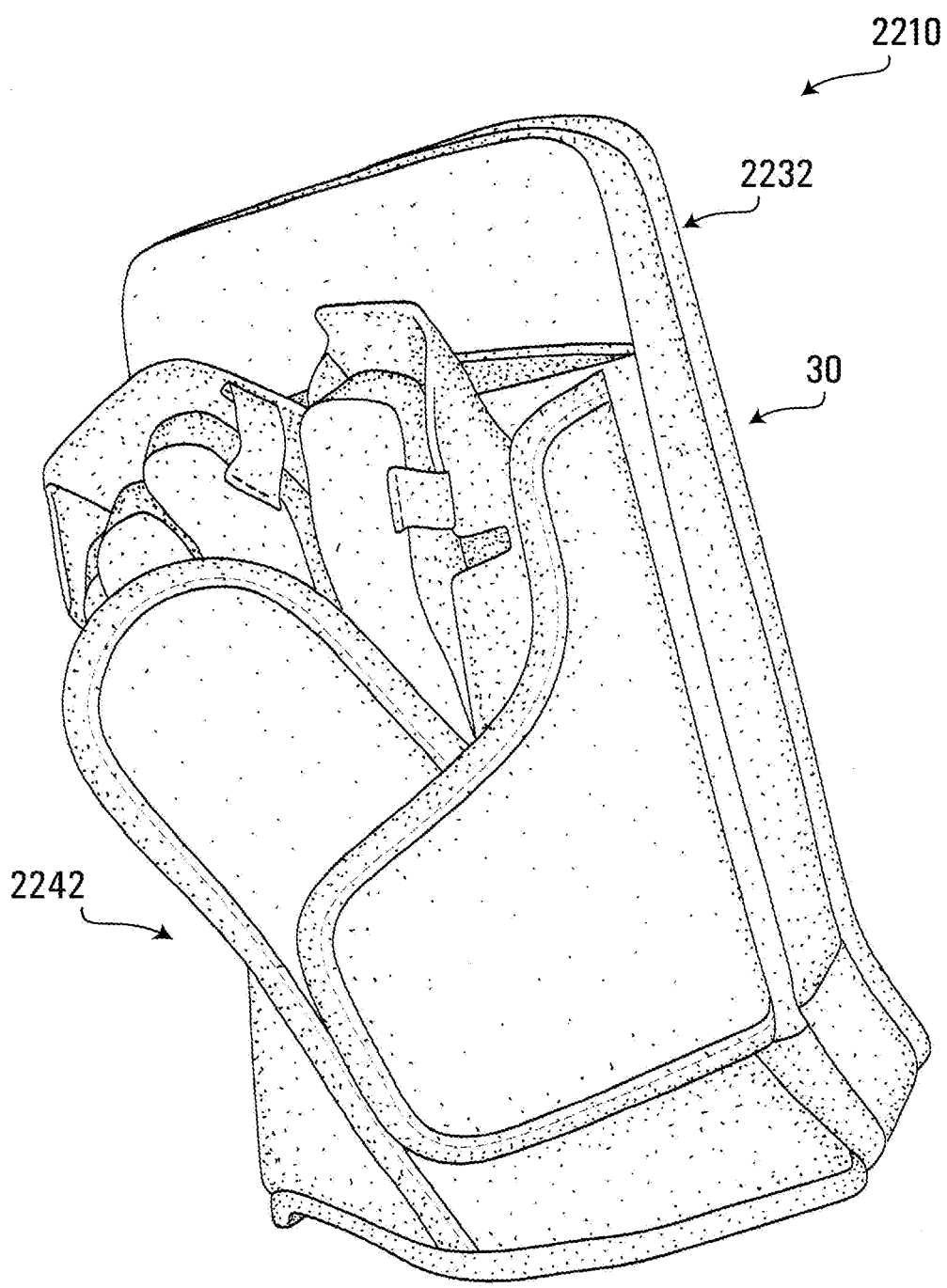
Figure 13A:
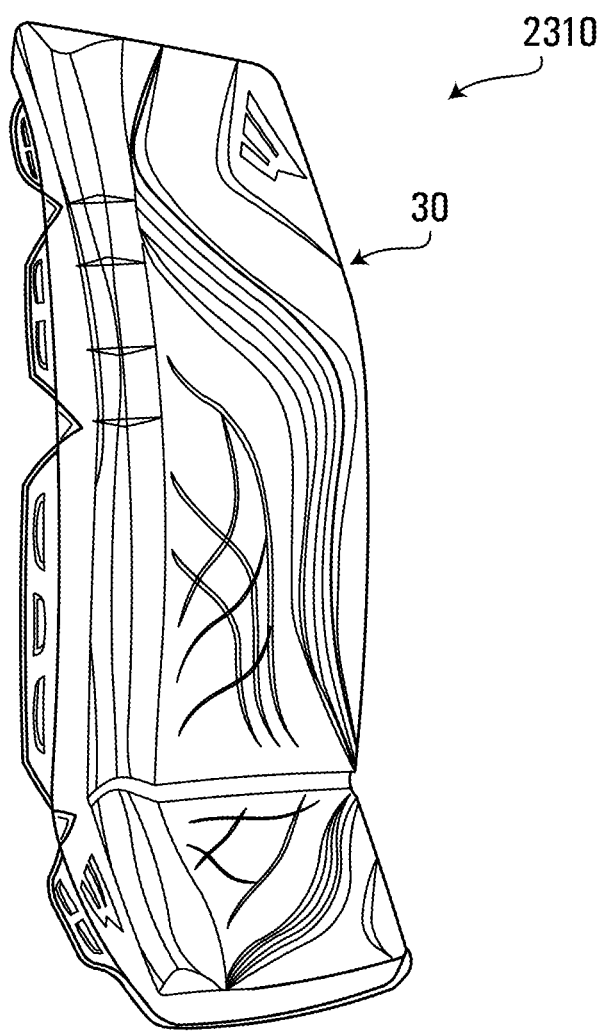
Figure 13B:
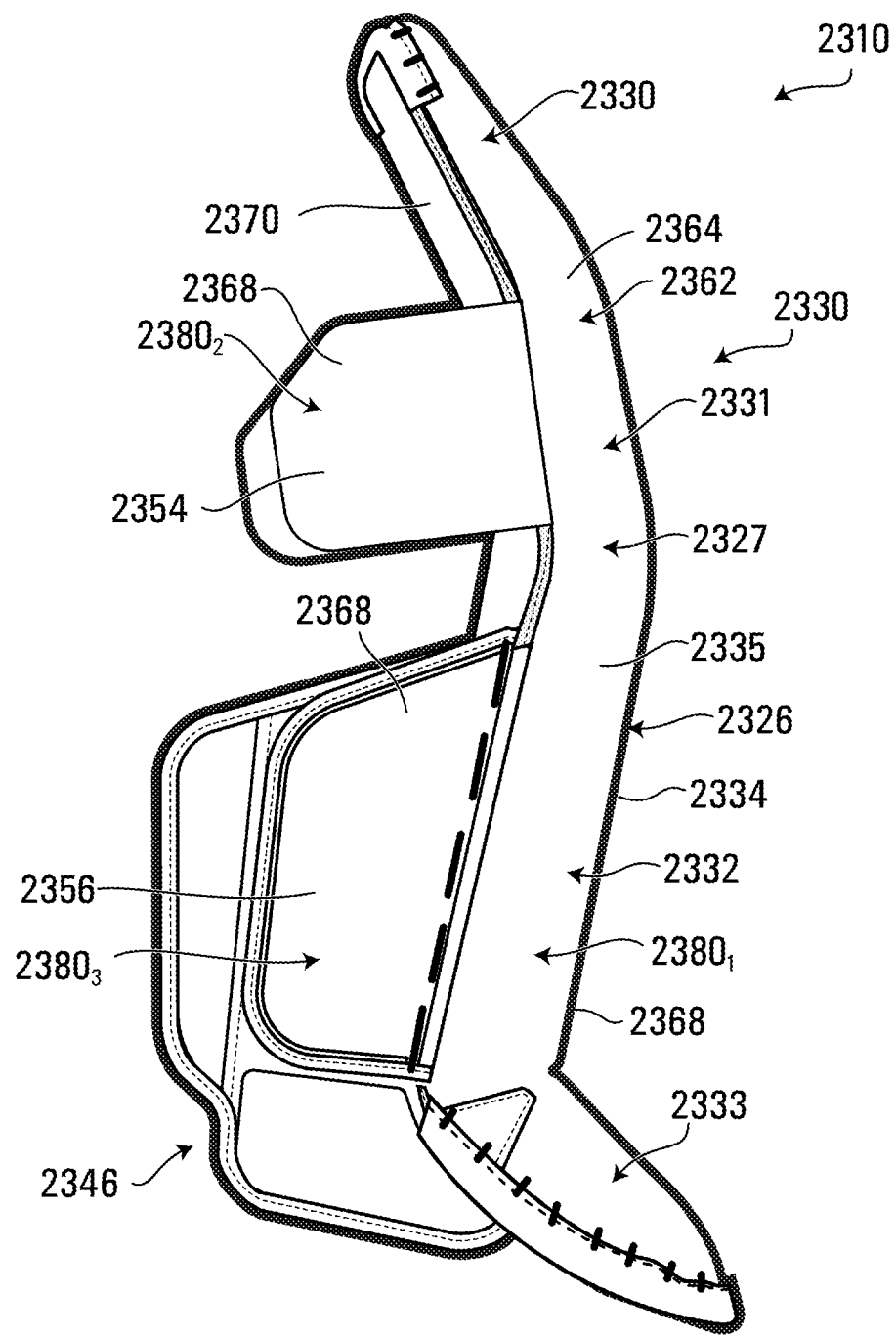
Figure 13C:
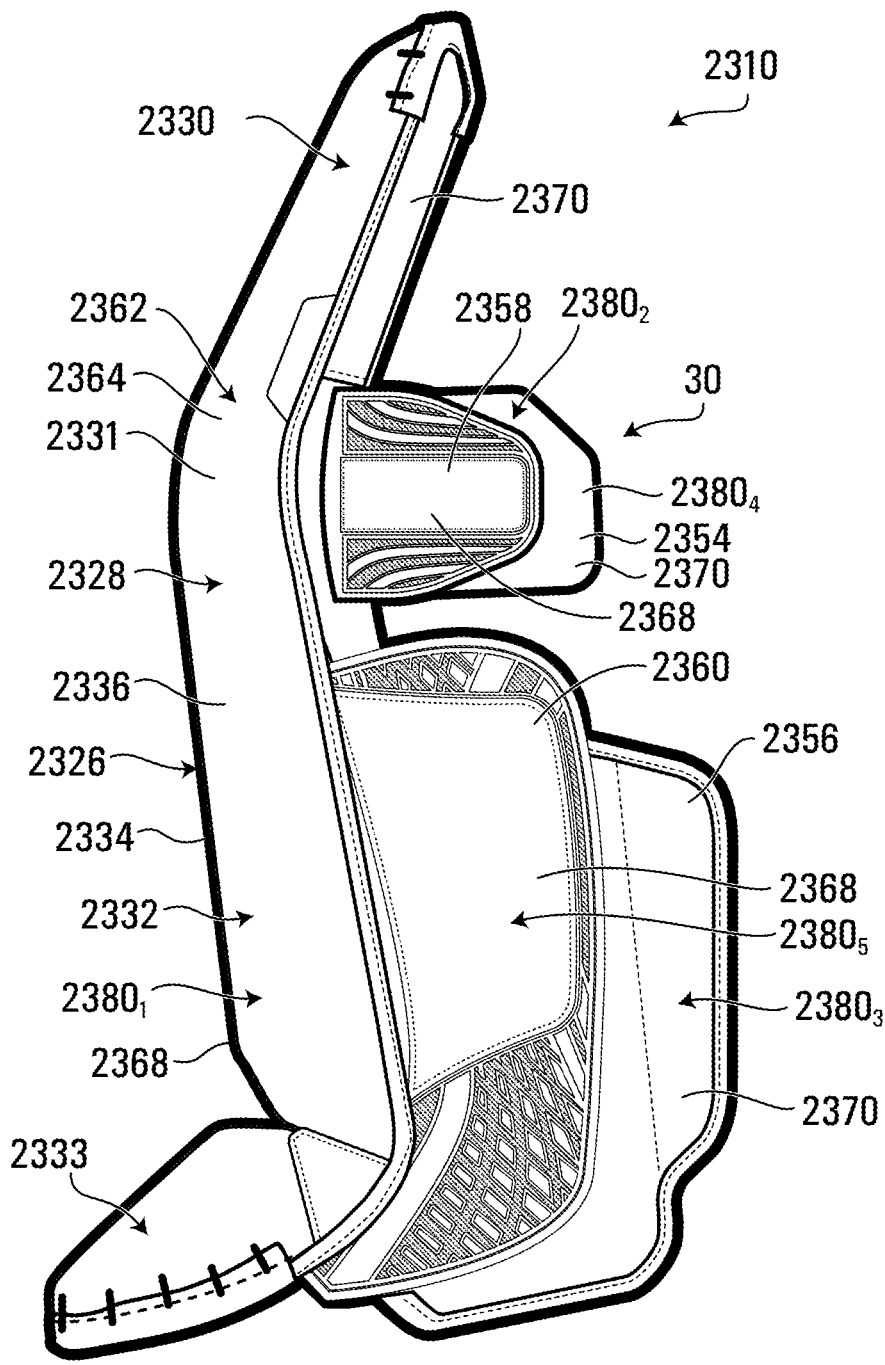
Figure 13D:
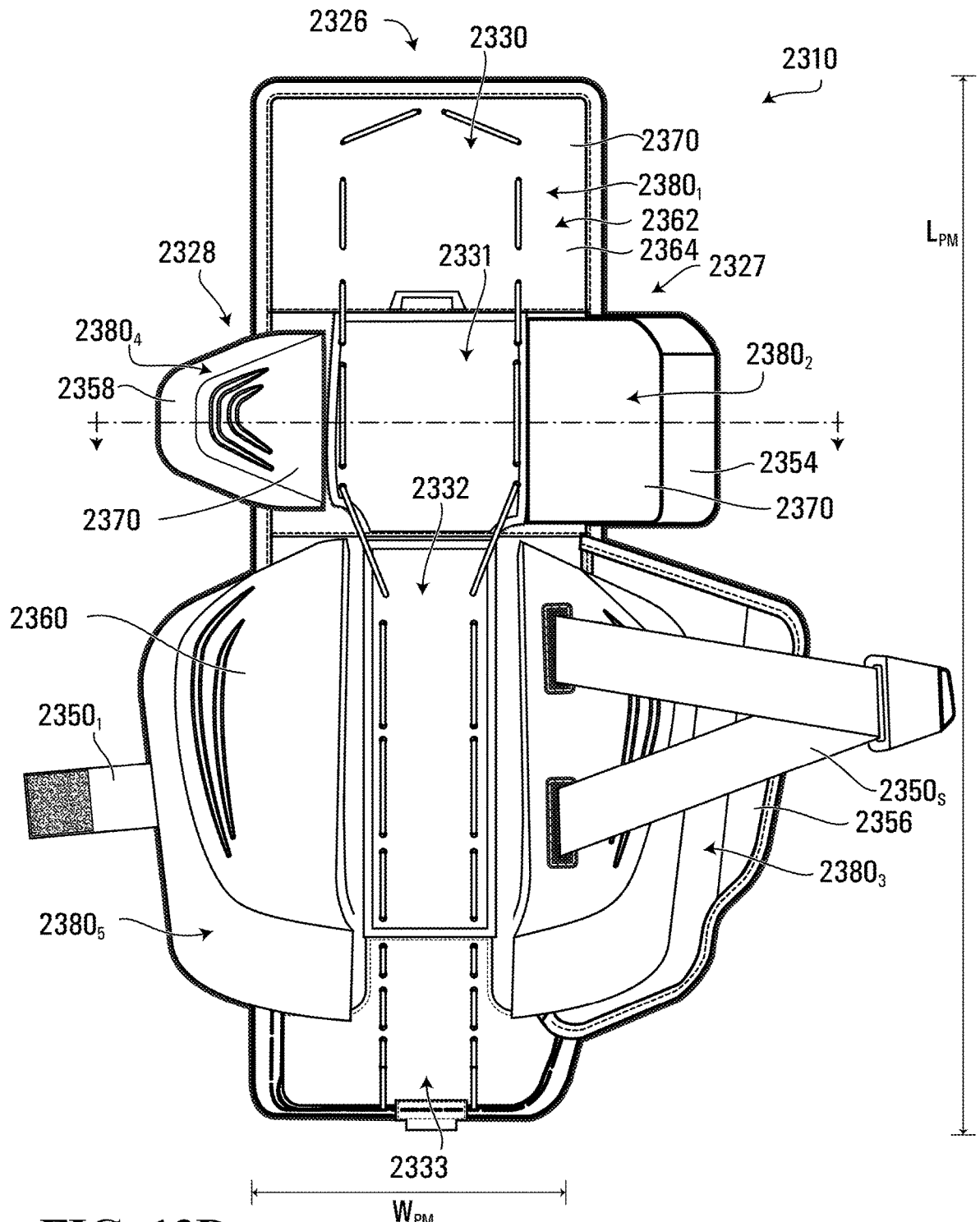
Figure 13E:
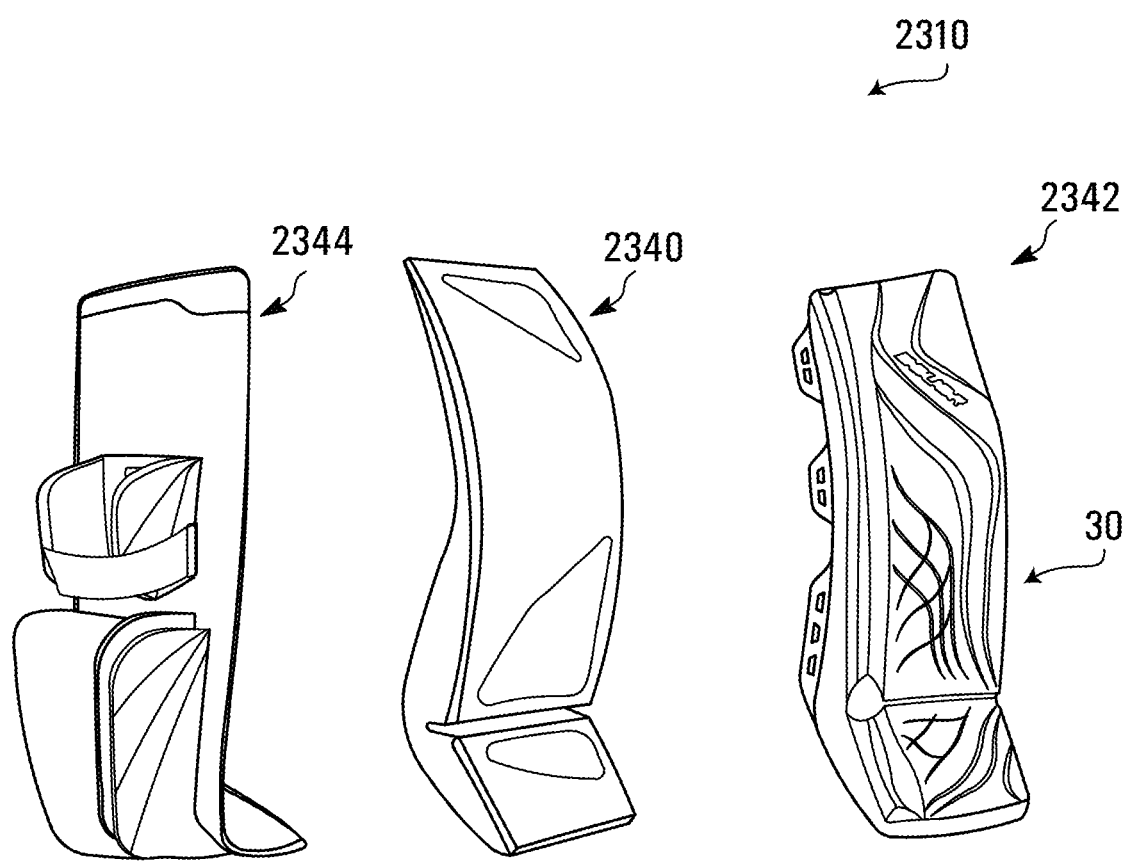

In yet another specific non-limiting example of implementation, the article of sports equipment is an article of protective athletic gear. FIG. 8 shows an embodiment of an elbow pad to which specific non-limiting examples of implementation may be applied. FIGS. 9 and 11 show embodiments of shoulder pads 1915, 2110, to which specific non-limiting examples of implementation may be applied. FIG. 10 shows an embodiment of a hockey player leg pad 2010 to which specific non-limiting examples of implementation may be applied. FIG. 12 shows an embodiment of a goalie blocker 2210 to which specific non-limiting examples of implementation may be applied. FIGS. 13A to 13G show embodiments of a hockey goaltender pad 2310 to which specific non-limiting examples of implementation may be applied.

In this embodiment, as shown in FIGS. 13A to 13G the article is a hockey goalkeeper leg pad 2310. The hockey goalkeeper leg pads 2310 wearable on a hockey goalkeeper's legs $2316_1$, $2316_2$ while playing hockey to protect the legs $2316_1$, $2316_2$ against an impact from a puck, ball, hockey stick or other object and/or to protect the legs $2316_1$, $2316_2$ when moving (e.g., dropping) them onto a playing surface. The hockey goalkeeper may be referred to as a "goalie" and thus the hockey goalkeeper leg pads 2310 may be referred to as "goalie leg pads", "goalie pads", or just "leg pads" of the goalie. In this embodiment, a type of hockey played is ice hockey such that the goalie pads 2310 are ice hockey goalie pads, the goalie is an ice hockey goalie, and the playing surface is ice.

As further discussed later, in this embodiment, protective parts (e.g., pad members) of the goalie pads 2310 are adjustable to adjust how the goalie pads 2310 fit on the goalie's legs $2316_1$, $2316_2$, and their adjustability is provided in a way that is relatively light, easy to use, and simple to manufacture.

The goalie pads 2310 protect various regions of the goalie's legs $2316_1$, $2316_2$. Each leg $2316_x$ of the goalie comprises an upper leg region 2318, a knee 2319, a lower leg region 2320, and a foot 2321. The upper leg region 2318 is above the knee 2319, while the lower leg region 2320 is below the knee 2319 and above the foot 2321. The leg $2316_x$ of the goalie has a front 2322, a back 2323, a medial side 2324 (sometimes referred to as an "inner side"), and a lateral side 2325 (sometimes referred to as an "outer side").

Each goalie pad 2310 comprises an upper leg portion 2330, a knee portion 2331, a lower leg portion 2332, and a foot portion 2333 respectively configured to be positioned adjacent to the upper leg region 2318, the knee 2319, the lower leg region 2320, and the foot 2321 of the goalie's leg $2316_x$ when the goalie pad 2310 is worn on the leg $2316_x$. The upper leg portion 2330 is above the knee portion 2331, while the lower leg portion 2332 is below the knee portion 2331 and above the foot portion 2333. Respective ones of these portions of the goalie pad 2310 comprise frontal, medial, and lateral parts such that the goalie pad 2310 comprises a frontal portion 2326, a medial portion 2327, and a lateral portion 2328 respectively configured to be positioned adjacent to the front 2322, the medial side 2324, and the lateral side 2325 of the goalie's leg $2316_x$ when the goalie pad 2310 is worn on the leg $2316_x$. The frontal portion 2326 comprises a front of the goalie pad 2310, the medial portion 2327 comprises a medial side of the goalie pad 2310, and the lateral portion 2328 comprises a lateral side of the goalie pad 2310. A longitudinal direction of the goalie pad 2310 is substantially parallel to a longitudinal axis of the goalie's leg $2316_x$, a lateral (i.e., widthwise) direction of the goalie pad 2310 is perpendicular to its longitudinal direction and substantially parallel to a dextrosinistral axis of the goalie's leg $2316_x$, and a front-back direction of the goalie pad 2310 is perpendicular to its longitudinal direction and substantially parallel to a dorsoventral axis of the goalie's leg $2316_x$.

In this embodiment, the knee portion 2331 comprises a medial part 4231 including a medial knee wing 2337 and a lateral part 2347 including a lateral knee wing 2339 that project rearwardly and define a knee cradle to receive the goalie's knee 2319. The medial part 2341 of the knee portion 2331 also comprises a knee landing 2343 projecting rearwardly and configured to engage the goalie's knee 2319 when dropping to the ice (e.g., in a butterfly position). Similarly, in this embodiment, the lower leg portion 2332 comprises a medial part 2346 including a medial calf wing 2349 and a lateral part 2348 including a lateral calf wing 2361 that project rearwardly to receive the goalie's lower leg 2320. The medial part 2346 of the lower leg portion 2332 also comprises a calf landing 2363 to engage the goalie's lower leg 2320 when dropping to the ice.

The goalie pad 2310 can be secured to the goalie's leg $2316_x$ in any suitable way. In this embodiment, the goalie pad 2310 comprises straps to secure it to the goalie's leg $2316_x$.

In this embodiment, the leg pad 2310 comprises an outer shell 2342, an inner liner 2344, and protective padding 2340 disposed between the outer shell 2342 and the inner liner 2344.

The outer shell 2342 comprises an outer surface 2351 of the leg pad 2310 that faces away from the goalkeeper's leg $2316_x$. In this embodiment, the outer shell 2342 comprises an upper leg portion 2352, a knee portion 2353, a lower leg portion 2354, and a foot portion 2355 which constitute respective parts of the upper leg portion 2330, the knee portion 2331, the lower leg portion 2332, and the foot portion 2333 of the leg pad 2310. Each of these portions of the outer shell 2342 comprises a frontal part, a medial part, and a lateral part such that the outer shell 2342 comprises a frontal portion 2356, a medial portion 2357, and a lateral portion 2358 which constitute respective parts of the frontal portion 2326, the medial portion 2327, and the lateral portion 2328 of the leg pad 2310.

The protective padding 2340 provides padded protection to the goalkeeper's leg $2316_x$. In this embodiment, the protective padding 2340 comprises an upper leg padding portion $2348_1$, a knee padding portion $2348_2$, a lower leg padding portion $2348_3$ and a foot padding portion $2348_4$ constituting respective parts of the upper leg portion 2330, the knee portion 2331, the lower leg portion 2332, and the foot portion 2333 of the leg pad 2310. In this example, respective ones of the padding portions $2348_1$-$2348_P$ are part of a common continuous pad that extends from the upper leg portion 2330 to the foot portion 2333 of the leg pad 2310.

The inner liner 2344 of the pad 2310 is configured to face the goalie's leg $2316_x$. A material 2376 of the inner layer 2344 may be of any suitable kind. For example, in some embodiments, the material 2376 may be fabric such as a woven fabric, a nonwoven fabric, synthetic microfibers, a synthetic woven knit, a polyurethane laminate, a mesh, or any other suitable fabric. The inner liner 2344 may be implemented in various other ways in other embodiments.

The outer cover 2342, the inner liner 2344, and the protective padding 2340 of the pad 2310 may be connected together in any suitable way. For example, in some embodiments, two or more of the outer cover 2342, the inner liner 2344, and the protective padding 2340 may be fastened by one or more fasteners, such as a stitching (i.e., a series of stitches), an adhesive, a series of staples, one or more laces, etc.

Although in embodiments considered above the article is an article of protective athletic gear and is more specifically a hockey goalkeeper leg pad, in other embodiments, the article of may be any other protective athletic gear usable by a hockey goalie.

For example, the article may be a chest protector for a goalie for protecting the goalie's torso and arms. The chest protector comprises pads and a liner constructed using principles described herein in. The pads may constitute any portion of the chest protector (e.g., a chest portion, an upper arm portion, a lower arm portion, an abdominal portion, etc.).

As another example, as shown in FIG. 12, the article may be a blocker glove 2210 for a goalie for protecting the goalie's hand and deflecting a puck or ball. In this example, the blocker glove 2210 comprises a board portion 2232 which the goalie uses to deflect pucks or balls and a glove portion 2242. The board portion 2232 may comprise padding.

Although in embodiments considered above the article of protective athletic gear is a hockey goalie protective athletic gear, in other embodiments, the article of protective athletic gear may be any other protective athletic gear usable by a player playing another type of contact sport (e.g., a "full-contact" sport) in which there are significant impact forces on the player due to player-to-player and/or player-to-object contact or any other type of sports, including athletic activities other than contact sports.

For example, in some embodiments, as shown in FIG. 8, the article may be an arm guard 1810 (e.g., an elbow guard)

for protecting an arm (e.g., an elbow) of a user, in which the arm guard 1810 comprises a pad 1836 and an inner liner 1844.

As another example, in some embodiments, as shown in FIGS. 9 and 11, the article may be shoulder pads 1915, 2110 for protecting an upper torso (e.g., shoulders and a chest) of a user (e.g., a hockey player, a baseball catcher), in which the shoulder pads 1915, 2110 comprise pads 1936, 2136 and an inner liner 1944, 2144.

As another example, in some embodiments, as shown in FIG. 10, the article may be a leg guard 2010 (e.g., a hockey player leg pad (also referred-to as a shin guard)) for protecting a leg (e.g., a shin) of a user, in which the leg guard comprises pads 2036 and an inner liner 2044.

The article of protective athletic gear, including its components, may be implemented in any other suitable manner in other embodiments.

Footwear, e.g., Skates

In a specific non-limiting example of implementation, the article of sports equipment is footwear, e.g., a skate. FIGS. 14A to 14M show embodiments of a skate 2410 to which specific non-limiting examples of implementation may be applied.

Figure 14A:
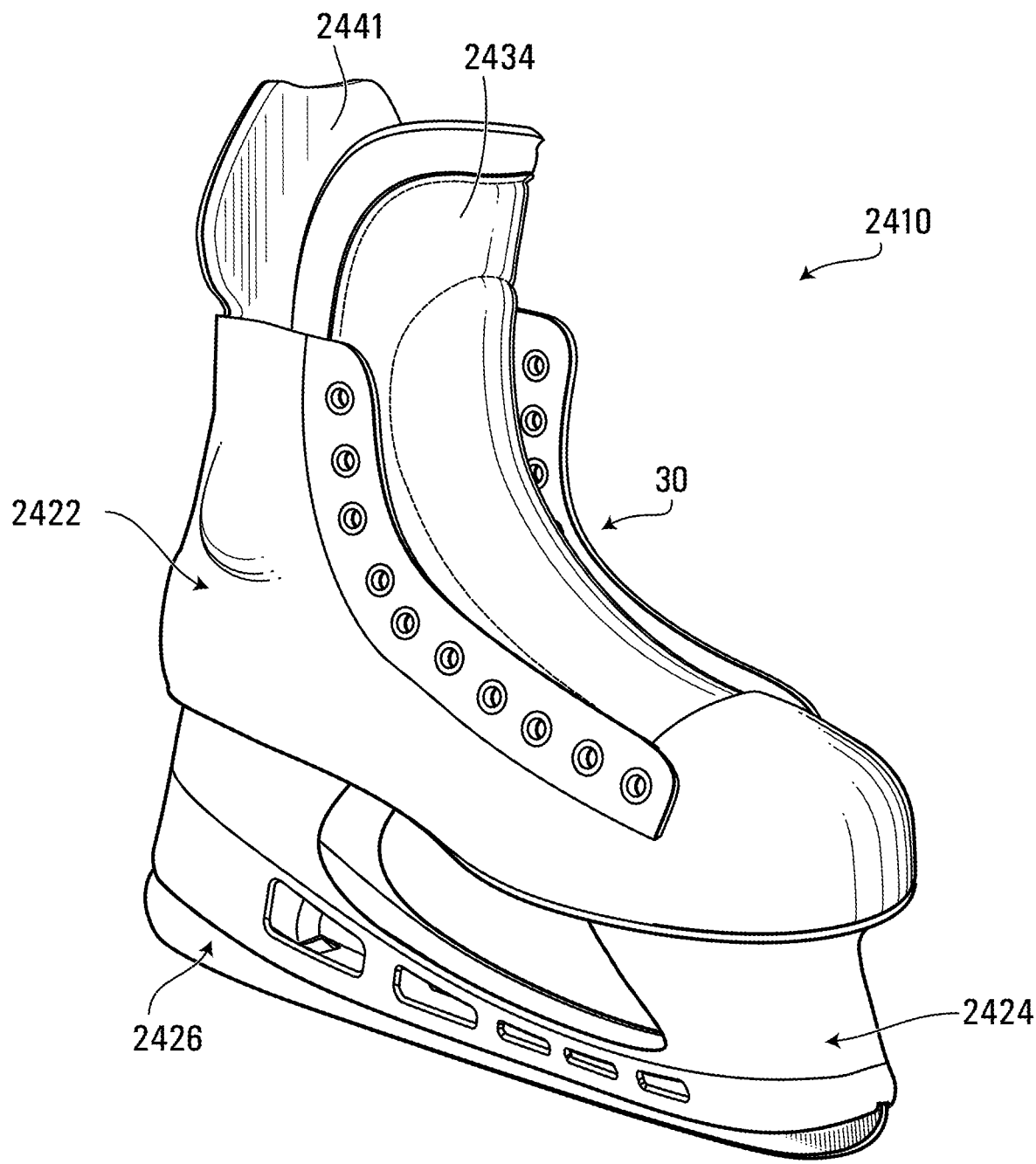
Figure 14B:
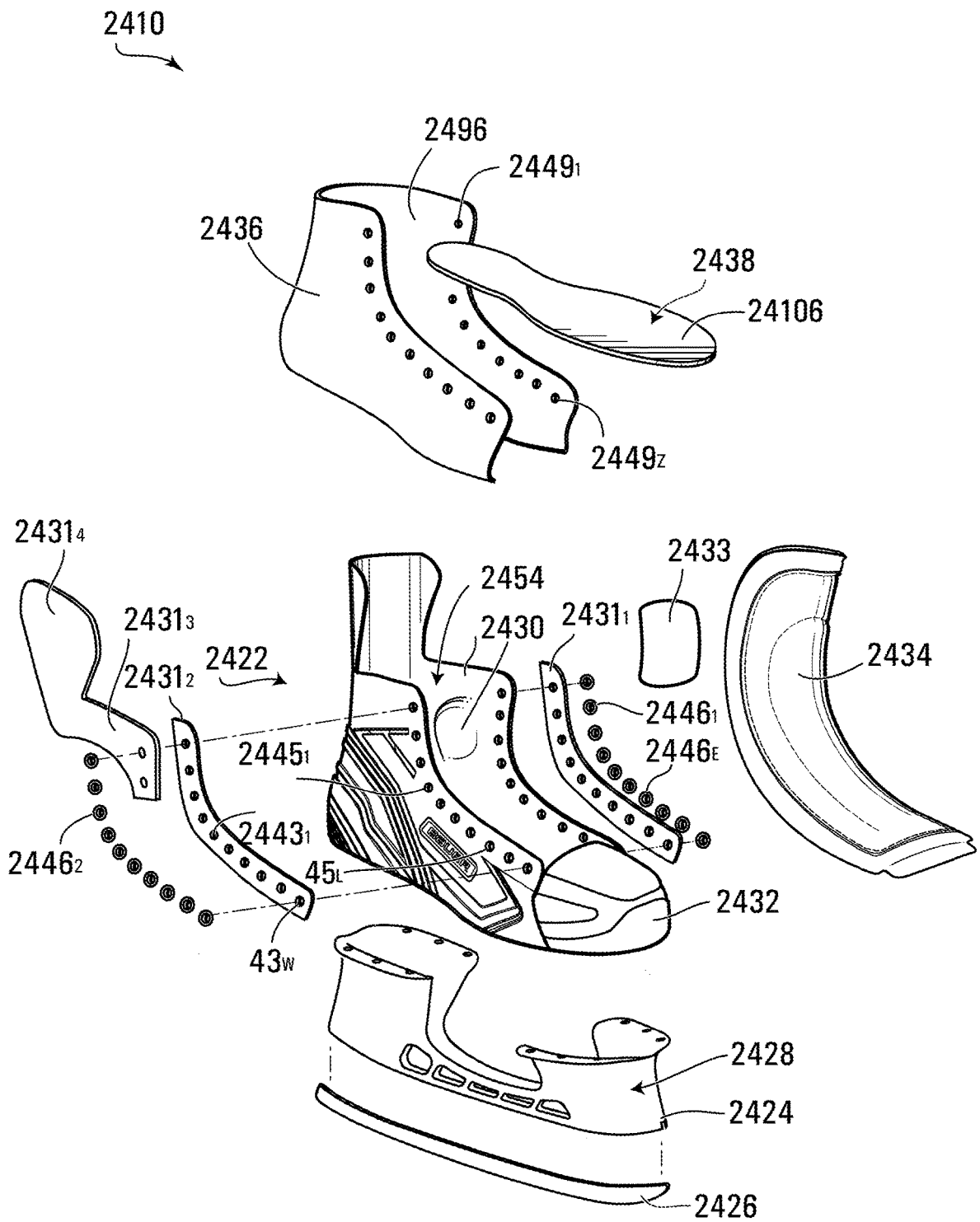
Figure 14C:
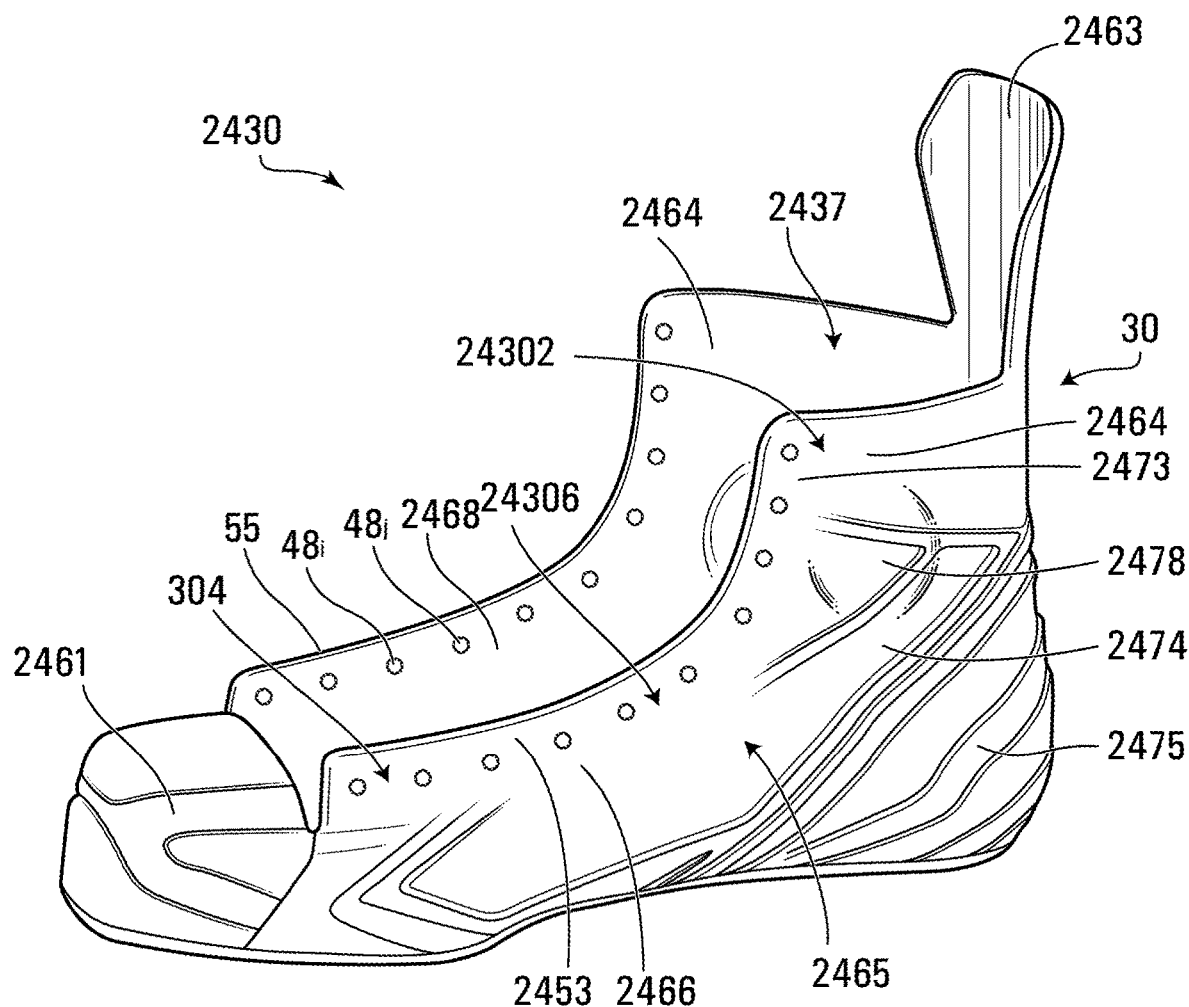
Figure 14D:
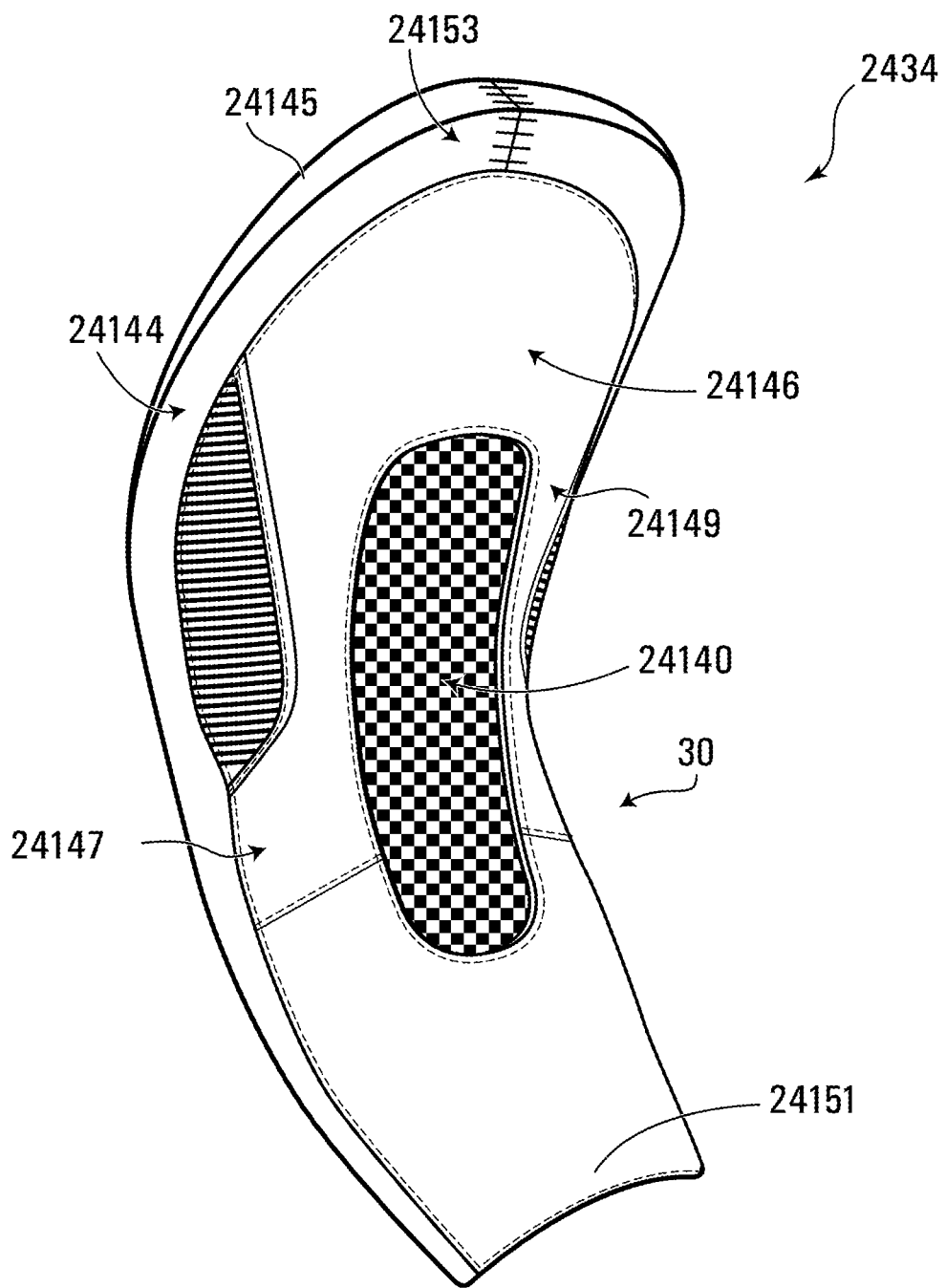
Figure 14E:
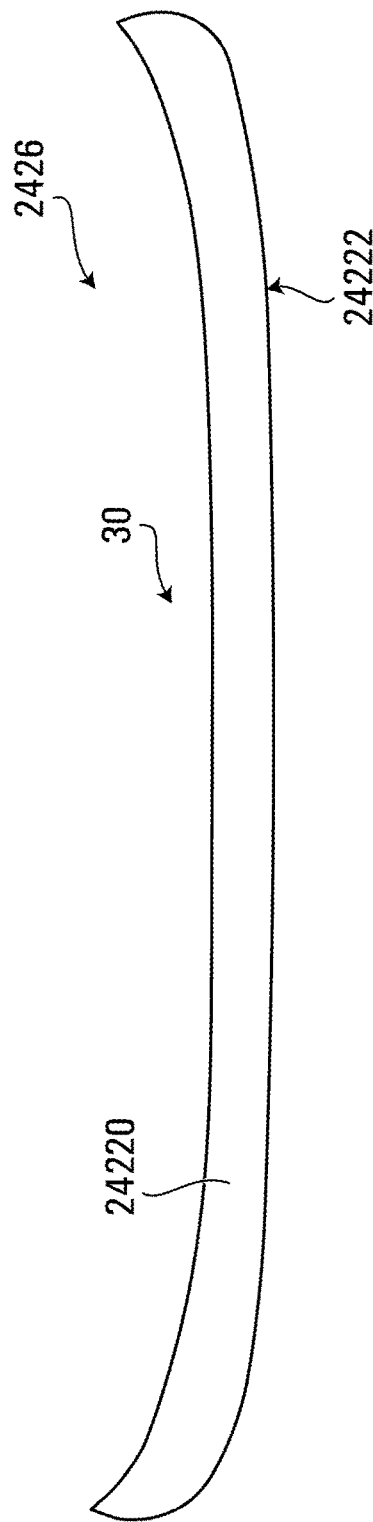
Figure 14G:
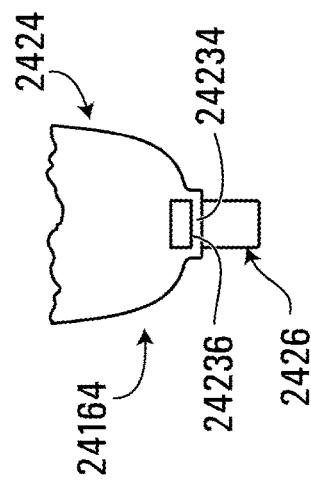
Figure 14F:
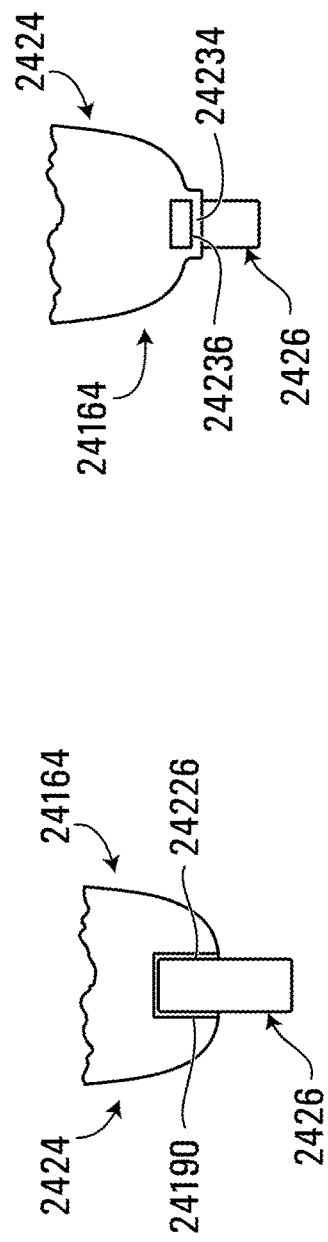
Figure 14H:
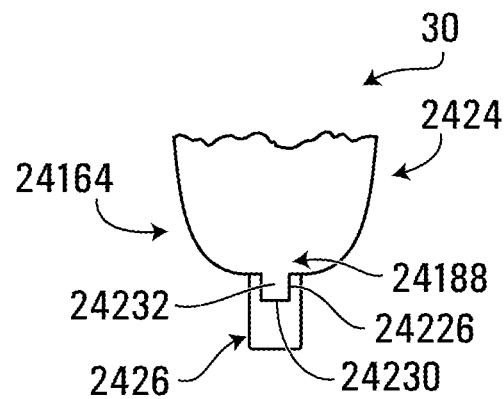
Figure 14I:
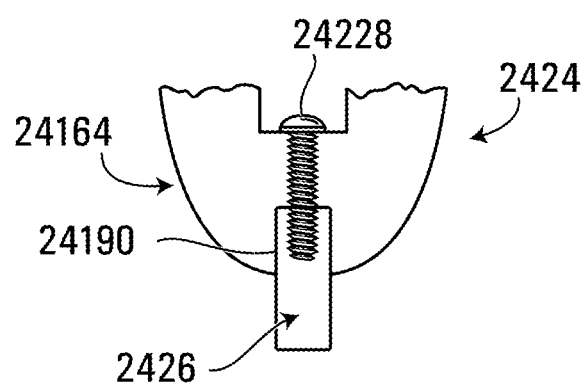
Figure 14J:
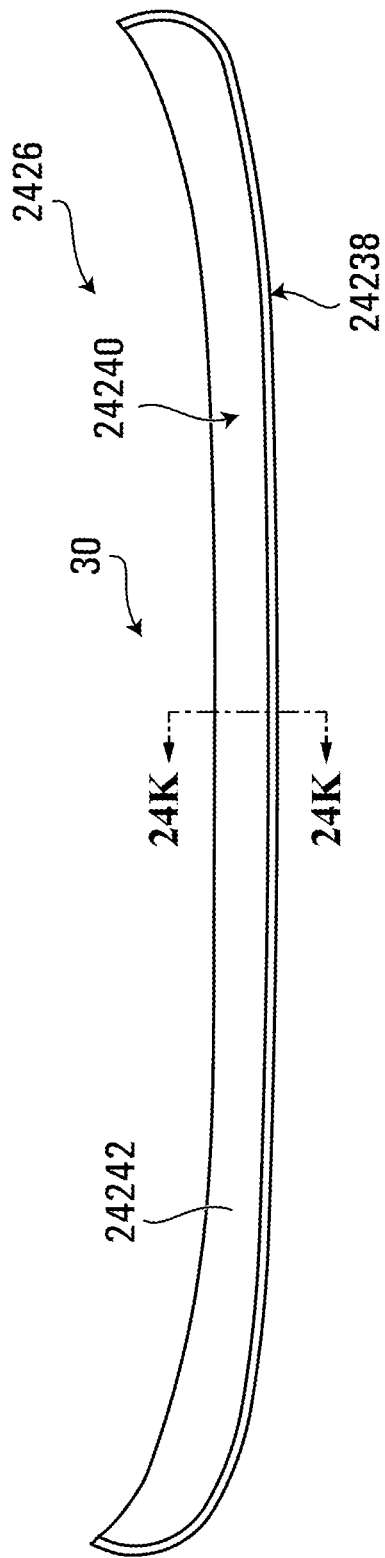
Figure 14K:
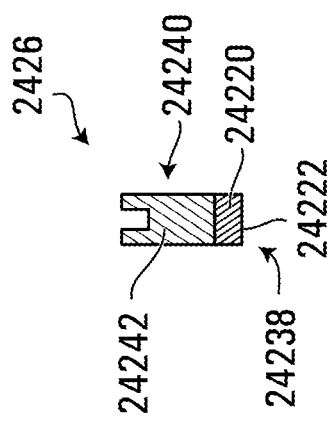
Figure 14L:
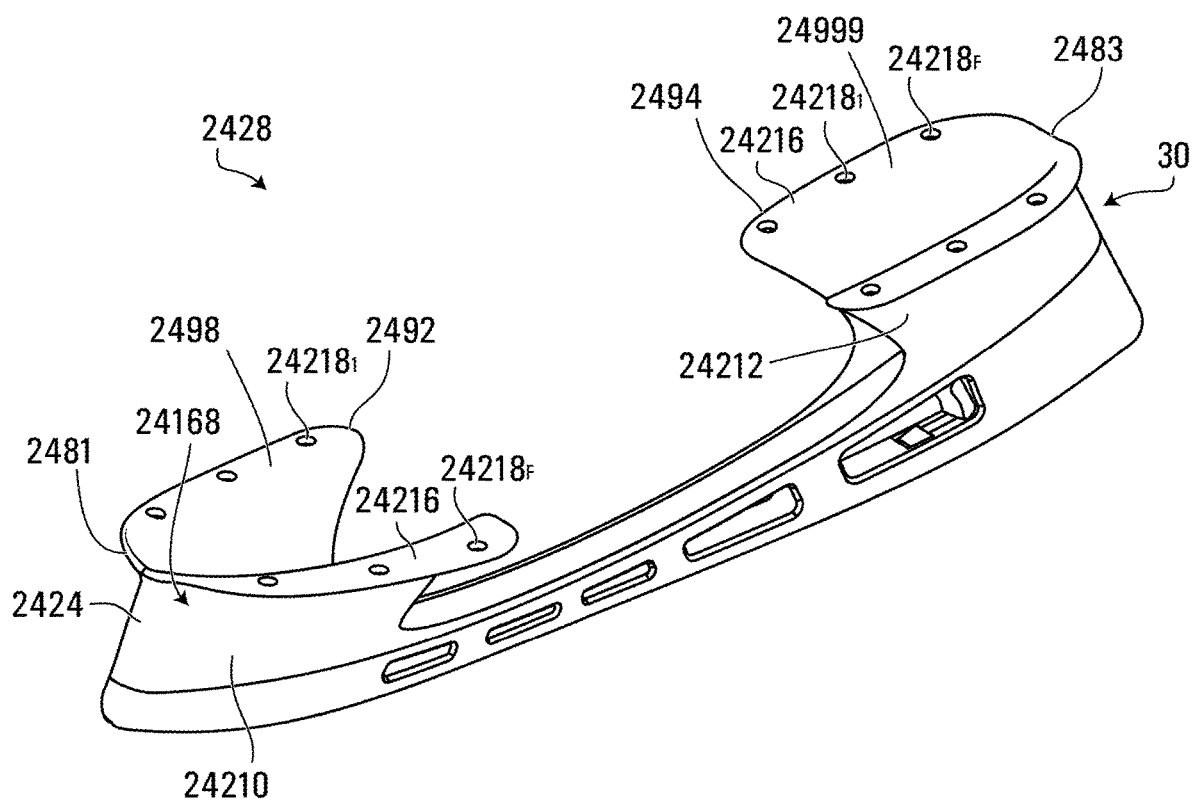
Figure 14M:
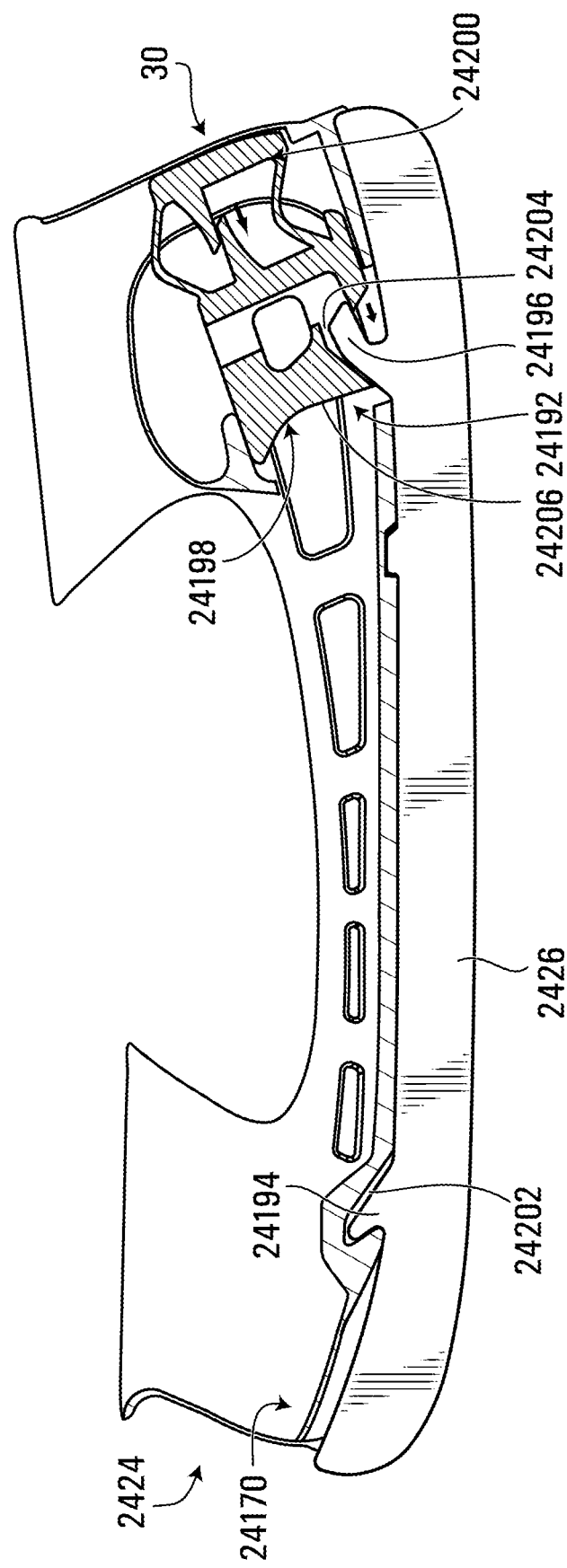
Figure 14N:
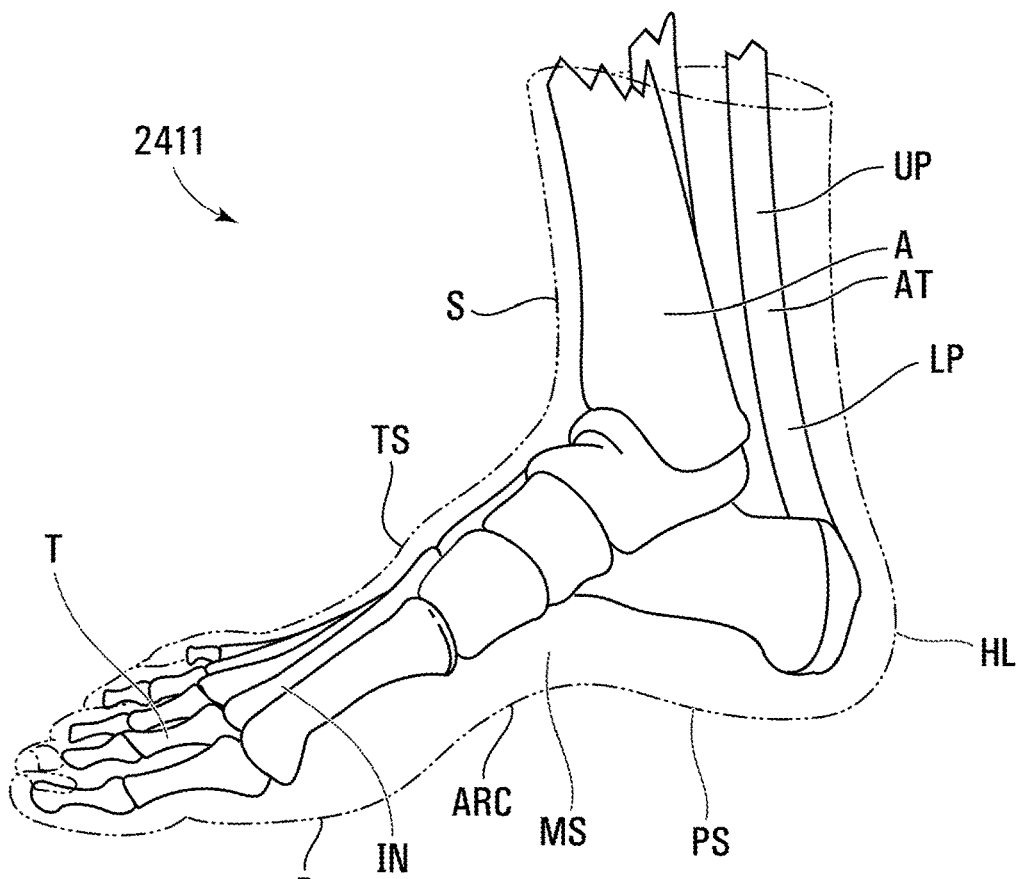
Figure 14O:
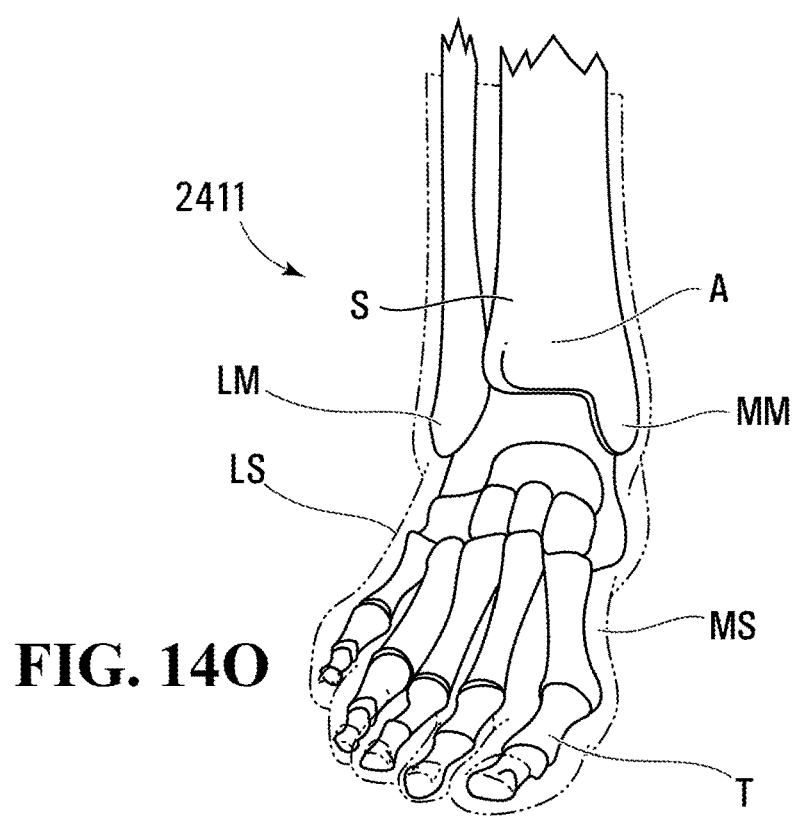
Figure 15A:
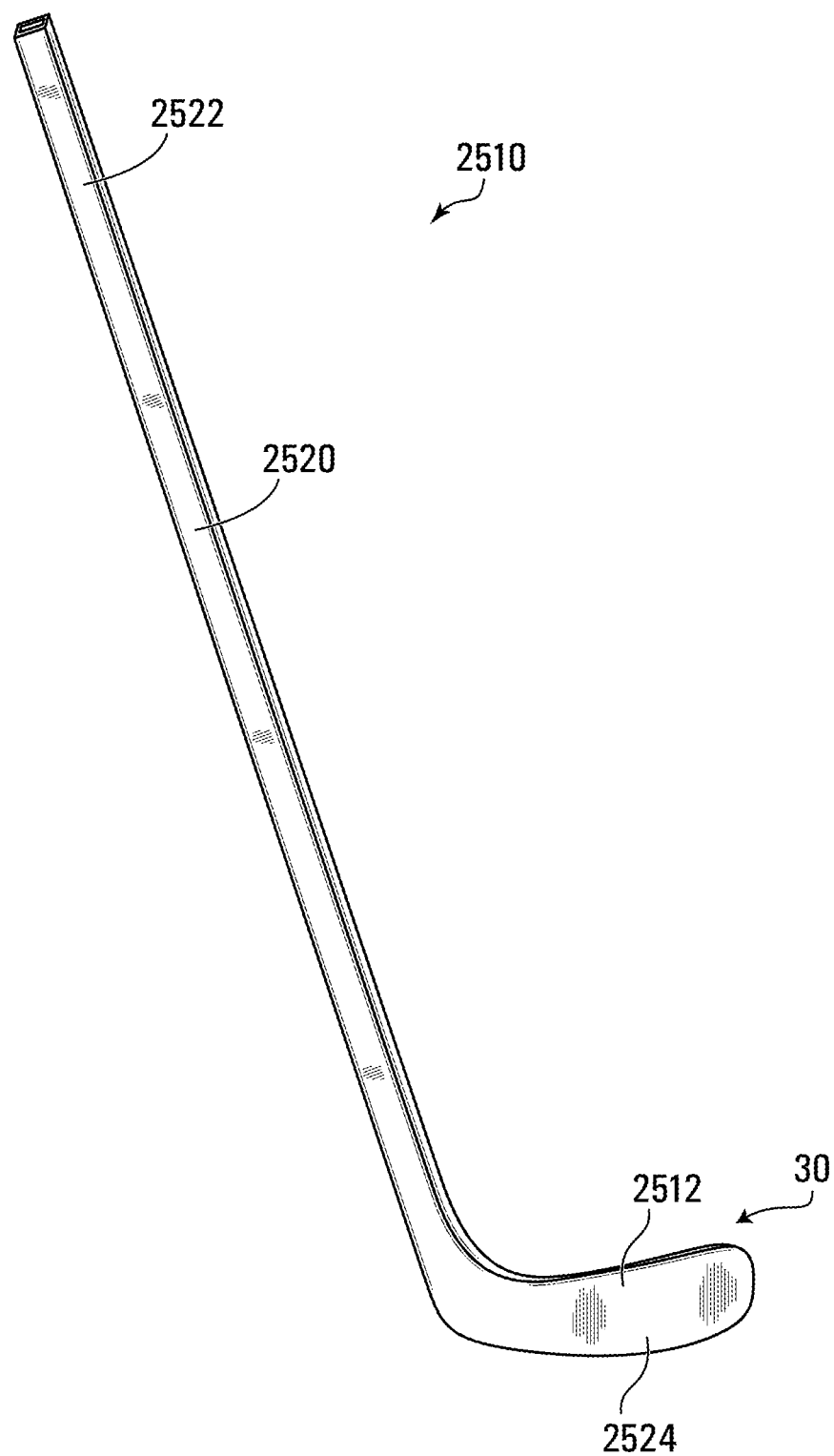
Figure 15B:
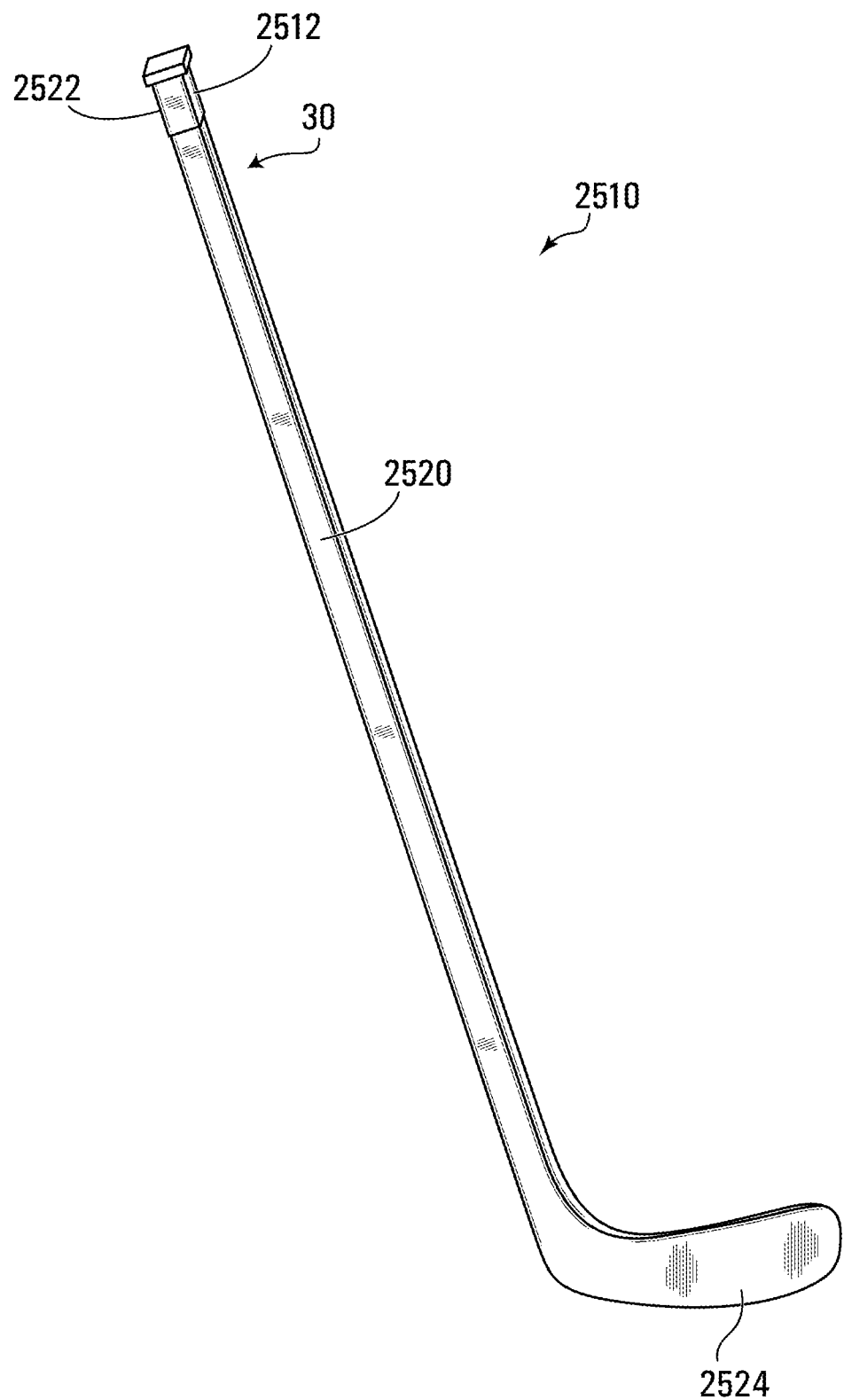

In this embodiment, as shown in FIGS. 14A to 14O, the skate 2410 for a user to skate on a skating surface. In this embodiment, the skate 2410 is a hockey skate for the user who is a hockey player playing hockey. In this example, the skate 2410 is an ice skate, a type of hockey played is ice hockey, and the skating surface is ice.

The skate 2410 comprises a skate boot 2422 for receiving a foot of the player and a skating device 2428 disposed beneath the skate boot 2422 to engage the skating surface. In this embodiment, the skating device 2428 comprises a blade 2426 for contacting the ice and a blade holder 2424 between the skate boot 2422 and the blade 2426. The skate 2410 has a longitudinal direction, a widthwise direction, and a heightwise direction.

The skate boot 2422 defines a cavity for receiving the player's foot. The player's foot may include toes T, a ball B, an arch ARC, a plantar surface PS, a top surface TS including an instep IN, a medial side MS, and a lateral side LS. The top surface TS of the player's foot 2411 is continuous with a lower portion of a shin S of the player. In addition, the player has a heel HL, an Achilles tendon AT, and an ankle A having a medial malleolus MM and a lateral malleolus LM that is at a lower position than the medial malleolus MM. The Achilles tendon AT has an upper part UP and a lower part LP projecting outwardly with relation to the upper part UP and merging with the heel HL. A forefoot of the player includes the toes T and the ball B, a hindfoot of the player includes the heel HL, and a midfoot of the player is between the forefoot and the hindfoot.

The skate boot 2422 comprises a front portion 2456 for receiving the toes T of the player, a rear portion 2458 for receiving the heel HL and at least part of the Achilles tendon AT and the ankle A of the player, and an intermediate portion 2460 between the front portion 2456 and the rear portion 2458.

More particularly, in this embodiment, the skate boot 2422 comprises a body 2430 and a plurality of components affixed to or otherwise supported by the body 2430, which in this embodiment includes overlays 2431$_1$-2431$_N$, a tendon guard 2441, a tongue 2434, a liner 2436 and a footbed 2438. The skate boot 2422 also comprises lacing holes 2445$_1$-2445$_L$ to receive a lace 2447 and extending through the body 2430, the liner 2436, and the overlays 2431$_1$, 2431$_2$ which are medial and lateral facings, respectively. In this example, eyelets 2446$_1$-2446$_E$ are provided in respective ones of the lacing holes 2445$_1$-2445$_L$ to engage the lace 2447.

The body 2430 is a shell which imparts strength and structural integrity to the skate 2410 to support the player's foot 2411. In this embodiment, the shell 2430 comprises a heel portion 2462 for receiving the heel HL of the player, an ankle portion 2464 for receiving the ankle A of the player, and medial and lateral side portions 2466, 2468 for respectively facing the medial and lateral sides MS, LS of the player's foot. The shell 2430 thus includes a quarter 2475 which comprises a medial quarter part 2477, a lateral quarter part 2479, and a heel quarter 2481. The heel portion 2462 may be formed such that it is substantially cup-shaped for following a contour of the heel HL of the player. The ankle portion 2464 comprises medial and lateral ankle sides 2474, 2476. The medial ankle side 2474 has a medial depression 2478 for receiving the medial malleolus MM of the player and the lateral ankle side 2476 has a lateral depression 2480 for receiving the lateral malleolus LM of the player. The lateral depression 2480 is located slightly lower than the medial depression 2478 for conforming to the morphology of the player's foot 2411. In this example, the shell 2430 also comprises a sole portion 2469 for facing the plantar surface PS of the player's foot 2411 and a toe portion 2461 for enclosing the toes T of the player.

In this embodiment, the shell 2430 may be manufactured by any suitable way, and any suitable material M may be used to make the shell 2430. For example, in this embodiment, a polymeric material such as polyethylene, polypropylene, polyurethane (PU), ethylene-vinyl acetate (EVA), nylon, polyester, vinyl, polyvinyl chloride, polycarbonate, an ionomer resin (e.g., Surlyn®), styrene-butadiene copolymer (e.g., K-Resin®) etc.), self-reinforced polypropylene composite (e.g., Curv®), glass reinforced materials and/or any other thermoplastic or thermosetting polymer may be used. Different parts of the shell 2430 may vary in material composition, stiffness and/or in thickness for fit, comfort, performance, and/or other reasons.

In this embodiment, the liner 2436 of the skate boot 2422 is affixed to an inner surface 2437 of the shell 2430 and comprises an inner surface 2496 for facing the heel HL and medial and lateral sides MS, LS of the player's foot 2411 and ankle A. The liner 2436 may be affixed to the shell 2430 by stitching or stapling the liner 2436 to the shell 2430, gluing with an adhesive and/or any other suitable technique. The inner lining 2436 may be made of a soft material (e.g., a fabric made of NYLON® fibers, polyester fibers or any other suitable fabric). The footbed 2438 may include a foam layer, which may be made of a polymeric material. For example, the footbed 2438, in some embodiments, may include a foam-backed fabric. The footbed 2438 is mounted inside the shell 2430 and comprises an upper surface 24106 for receiving the plantar surface PS of the player's foot 2411. In this embodiment, the footbed 38 affixed to the sole portion 2469 of the shell 2430 by an adhesive and/or any other suitable technique. In other embodiments, the footbed 2438 may be removable. In some embodiments, the footbed 2438 may also comprise a wall projecting upwardly from the upper surface 24106 to partially cup the heel HL and extend up to a medial line of the player's foot 2411.

The lacing holes 2445$_1$-2445$_L$ are configured to receive the lace 2447. In this embodiment, the lacing holes 2445$_1$-2445$_L$ extend through the shell 2430, the liner 2436, and the medial and lateral facings 2431$_1$, 2431$_2$. Thus, in this case, each lacing hole 2445$_x$ comprises an opening 2448$_x$ in the shell 2430, an opening 2449$_x$ in the liner 2436, and an opening 2443$_x$ in a given one of the medial and lateral facings 2431$_1$, 2431$_2$ that are aligned with one another to create the lacing hole 2445$_x$. In this embodiment, respective ones of the lacing holes 2445$_1$-2445$_L$ are disposed in the medial side portion 2466, the lateral side portion 2468 and the ankle portion 2464. In this embodiment, upper ones of the lacing holes 2445$_1$-2445$_L$ extend through the upper part 24302 of the shell 2430 and lower ones of the lacing holes 2445$_1$-2445$_L$ extend through the lower part 24304 of the shell 2430.

The tongue 2434 extends upwardly and rearwardly from the toe portion 2461 for overlapping the top surface TS of the player's foot 2411. In this embodiment, the tongue 2434 is affixed to the shell 2430. In particular, in this embodiment, the tongue 2434 is fastened to the toe portion 2461. In some embodiments, the tongue 2434 comprises a core 24140 defining a section of the tongue 2434 with increased rigidity, a padding member (not shown) for absorbing impacts to the tongue 2434, a peripheral member 24144 for at least partially defining a periphery 24145 of the tongue 2434, and a cover member 24146 configured to at least partially define a front surface of the tongue 2434. The tongue 2434 defines a lateral portion 24147 overlying a lateral portion of the player's foot 2411 and a medial portion 24149 overlying a medial portion of the player's foot 2411. The tongue 2434 also defines a distal end portion 24151 for affixing to the toe portion 2461 (e.g., via stitching or riveting) and a proximal end portion 24153 that is nearest to the player's shin S. The core 24140 may be made of foam or similar materials to that of the shell 2430 and may be formed by injection molding in a similar manner to that of the shell 2430, as described herein.

The tendon guard 2441 may be fastened to the shell 2430, such as via a mechanical fastener (e.g., via stitching, stapling, a screw, etc.) or in any other suitable way, or may be integrally made with the shell 2430. For instance, in some embodiments, the ankle portion 2464, the heel portion 2462, the medial side portion 2466, the lateral side portion 2468, the sole portion 2469, and the toe portion 2461 may be molded together and integral with one another and the tendon guard 2441 may be formed separately and attached to the shell 2430 after it has been molded, while in some embodiments the ankle portion 2464, the heel portion 2462, the medial side portion 2466, the lateral side portion 2468, the sole portion 2469, the toe portion 2461 and the tendon guard 2441 may be molded together and integral with one another.

In this embodiment, the blade 2426 comprises a lower portion and an upper portion. In this embodiment, the upper portion of the blade 2426 includes a plurality of projections 24194, 24196 which can be used to attach the blade to the blade holder 2424. The lower portion may comprise an ice-contacting material 24220 including an ice-contacting surface 24222 for sliding on the ice surface while the player skates. In this embodiment, the ice-contacting material 24220 is a metallic material (e.g., stainless steel). The ice-contacting material 24220 may be any other suitable material in other embodiments. In this embodiment, the lower portion and the upper portion of the blade 2426 are unitary and comprise the same material.

The blade 2426 may be implemented in any other suitable way in other embodiments. For example, in some embodiments, the blade 2426 may comprise a lower member 24238 that is made of the ice-contacting material 24220 and includes the ice-contacting surface 24222 and an upper member 24240 connected to the lower member 24238 and made of a material 24242 different from the ice-contacting material 24220. The lower member 24238 and the upper member 24240 of the blade 2426 may be retained together in any suitable way. For example, in some cases, the lower member 238 may be adhesively bonded to the upper member 24240 using an adhesive. As another example, in addition to or instead of being adhesively bonded, the lower member 24238 and the upper member 24240 may be fastened using one or more fasteners (e.g., rivets, screws, bolts, etc.). As yet another example, the lower member 24238 and the upper member 24240 may be mechanically interlocked by an interlocking portion of one of the lower member 24238 and the upper member 24240 that extends into an interlocking space (e.g., one or more holes, one or more recesses, and/or one or more other hollow areas) of the other one of the lower member 24238 and the upper member 24240 (e.g., the upper member 24240 may be overmolded onto the lower member 24238).

The blade holder 2424 comprises a lower portion 24162 comprising a blade-retaining base 24164 that retains the blade 2426 and an upper portion 24166 comprising a support 24168 that extends upwardly from the blade-retaining base 24164 towards the skate boot 2422 to interconnect the blade holder 2424 and the skate boot 2422. A front portion 24170 of the blade holder 2424 and a rear portion 24172 of the blade holder 2424 define a longitudinal axis 24174 of the blade holder 2424. The front portion 24170 of the blade holder 2424 includes a frontmost point 24176 of the blade holder 2424 and extends beneath and along the player's forefoot in use, while the rear portion 24172 of the blade holder 2424 includes a rearmost point 24178 of the blade holder 2424 and extends beneath and along the player's hindfoot in use. An intermediate portion 24180 of the blade holder 2424 is between the front and rear portions 24170, 24172 of the blade holder 2424 and extends beneath and along the player's midfoot in use. The blade holder 2424 comprises a medial side 24182 and a lateral side 24184 that are opposite one another.

The blade-retaining base 24164 is elongated in the longitudinal direction of the blade holder 2424 and is configured to retain the blade 2426 such that the blade 2426 extends along a bottom portion 24186 of the blade-retaining base 24164 to contact the ice surface. To that end, the blade-retaining base 24164 comprises a blade-retention portion 24188 to face and retain the blade 2426. In this embodiment, the blade-retention portion 24188 comprises a recess 24190 in which an upper portion of the blade 2426 is disposed.

The blade holder 2424 can retain the blade 2426 in any suitable way. For example, in this embodiment, the blade holder 2424 comprises a blade-detachment mechanism 24192 such that the blade 2426 is selectively detachable and removable from, and attachable to, the blade holder 2424 (e.g., when the blade 2426 is worn out or otherwise needs to be replaced or removed from the blade holder 2424).

More particularly, in this embodiment, the blade-detachment mechanism 24192 includes an actuator 24198 and a biasing element 24200 which biases the actuator 24198 in a direction towards the front portion 24170 of the blade holder 2424. In this embodiment, the actuator 24198 comprises a trigger. To attach the blade 2426 to the blade holder 2424, the front projection 24194 is first positioned within a hollow space 24202 (e.g., a recess or hole) of the blade holder 2424. The rear projection 24196 can then be pushed upwardly into a hollow space 24204 (e.g., a recess or hole) of the blade holder 2424, thereby causing the biasing element 24200 to bend and the actuator 24198 to move in a rearward direction. In this embodiment, the rear projection 24196 will eventually reach a position which will allow the biasing element 24200 to force the actuator 24198 towards the front portion 24170 of the blade holder 2424, thereby locking the blade 2426 in place. The blade 2426 can then be removed by pushing against a finger-actuating surface 24206 of the actuator 24198 to release the rear projection 24196 from the hollow space 24204 of the blade holder 2424. Thus, in this embodiment, the blade-detachment mechanism 24192 is free of any threaded fastener (e.g., a screw or bolt) to be manipulated to detach and remove the blade 2426 from the blade holder 2424 or to attach the blade 2426 to the blade holder 2424.

Further information on examples of implementation of the blade-detachment mechanism 24192 in some embodiments may be obtained from U.S. Pat. No. 8,454,030 hereby incorporated by reference herein. The blade-detachment mechanism 24192 may be configured in any other suitable way in other embodiments.

The support 24168 is configured for supporting the skate boot 2422 above the blade-retaining base 24164 and transmit forces to and from the blade-retaining base 24164 during skating. In this embodiment, the support 24168 comprises a front pillar 24210 and a rear pillar 24212 which extend upwardly from the blade-retaining base 24164 towards the skate boot 2422. The front pillar 24210 extends towards the front portion 2456 of the skate boot 2422 and the rear pillar 24212 extends towards the rear portion 2458 of the skate boot 2422. The blade-retaining base 24164 extends from the front pillar 24210 to the rear pillar 24212. More particularly, in this embodiment, the blade-retaining base 24164 comprises a bridge 24214 interconnecting the front and rear pillars 24210, 24212.

The skate 2410, including the skate boot 2422, the blade holder 2424 and the blade 2426, may be implemented in any other suitable manner in other embodiments.

Sticks

In another specific non-limiting example of implementation, the article of sports equipment is a stick. FIGS. 15A to 15E at 2510 and FIG. 16 at 2610 show embodiments of a hockey stick, and FIGS. 17A and 17B show an embodiment of a lacrosse stick at 2710, to which specific non-limiting examples of implementation may be applied.

FIGS. 15A to 15E show embodiments of a sporting implement 2510 for use by a user engaging in a sport. The sporting implement 2510 comprises an elongate holdable member 2512 configured to be held by the user and an object-contacting member 2514 configured to contact an object (e.g., a puck or ball) intended to be moved in the sport. In this embodiment, the sport is hockey and the sporting implement 2510 is a hockey stick for use by the user, who is a hockey player, to pass, shoot or otherwise move a puck or ball. The elongate holdable member 2512 of the hockey stick 2510 is a shaft, which comprises a handle 2520 of the hockey stick 2510, and the object-contacting member 2514 of the hockey stick 2510 is a blade.

In this embodiment, as further discussed later, the hockey stick 2510 is designed to enhance its use, performance and/or manufacturing, including, for example, by being lightweight, having improved strength, flex, stiffness, impact resistance and/or other properties, reducing scrap or waste during its construction, and/or enhancing other aspects of the hockey stick 2510.

The shaft 2512 is configured to be held by the player to use the hockey stick 2510. A periphery 2530 of the shaft 2512 includes a front surface 2516 and a rear surface 2518 opposite one another, as well as a top surface 2522 and a bottom surface 2524 opposite one another. Proximal and distal end portions 2526, 2528 of the shaft 2512 are spaced apart in a longitudinal direction of the shaft 2512, respectively adjacent to the handle 2520 and the blade 2514, and define a length of the shaft 2512. A length of the hockey stick 2510 is measured from a proximal end 2534 of the shaft 2512 along the top surface 2522 of the shaft 2512 through the blade 2514.

A cross-section of the shaft 2512 may have any suitable configuration. For instance, in this embodiment, the cross-section of the shaft 2512 has a major axis 2536 which defines a major dimension D of the shaft's cross-section and a minor axis 2538 which defines a minor dimension W of the shaft's cross-section. In this example, the cross-section of the shaft 2512 is generally polygonal. More particularly, in this example, the cross-section of the shaft 2512 is generally rectangular, with the front surface 2516, the rear surface 2518, the top surface 2522, and the bottom surface 2524 being generally flat. Corners between these surfaces of the shaft 2512 may be rounded or beveled.

The shaft 2512 may have any other suitable shape and/or be constructed in any other suitable way in other embodiments. For example, in some embodiments, the cross-section of the shaft 2512 may have any other suitable shape (e.g., the front surface 2516, the rear surface 2518, the top surface 2522, and/or the bottom surface 2524 may be curved and/or angular and/or have any other suitable shape, possibly including two or more sides or segments oriented differently, such that the cross-section of the shaft 2512 may be pentagonal, hexagonal, heptagonal, octagonal, partly or fully curved, etc.). As another example, the cross-section of the shaft 2512 may vary along the length of the shaft 2512.

The blade 2514 is configured to allow the player to pass, shoot or otherwise move the puck or ball. A periphery 2550 of the blade 2514 comprises a front surface 2552 and a rear surface 2554 opposite one another, as well as a top edge 2556, a toe edge 2558, a heel edge 2559, and a bottom edge 2560. The blade 2514 comprises a toe region 2561, a heel region 2562, and an intermediate region 2563 between the toe region 2561 and the heel region 2562. The blade 2514 has a longitudinal direction that defines a length of the blade 2514, a thicknesswise direction that is normal to the longitudinal direction and defines a thickness of the blade 2514, and a heightwise direction that is normal to the longitudinal direction and defines a height of the blade 2514.

A cross-section of the blade 2514 may have any suitable configuration. For instance, in this embodiment, the cross-section of the blade 2514 varies along the longitudinal direction of the blade 2514 (e.g., tapers towards the toe region 2561 of the blade 2514), with the front surface 2552 and the rear surface 2554 curving so that the front surface 2552 is concave and the rear surface 2554 is convex. Corners between the front surface 2552, the rear surface 2554, the top edge 2556, the toe edge 2558, the heel edge 2559, and the bottom edge 2560 may be rounded or beveled.

The blade 2514 may have any other suitable shape and/or be constructed in any other suitable way in other embodiments. For example, in some embodiments, the cross-section of the blade 2514 may have any other suitable shape (e.g., the front surface 2552, the rear surface 2554, the top edge 5256, the toe edge 2558, the heel edge 2559, and the bottom edge 2560 may be curved differently and/or angular and/or have any other suitable shape, etc.).

The shaft 2512 and the blade 2514 may be interconnected in any suitable way. For instance, in this embodiment, the shaft 2512 and the blade 2514 are integrally formed with one another (i.e., at least part of the shaft 2512 and at least of the blade 2514 are integrally formed together) such that they constitute a one-piece stick. In other embodiments, the blade 2514 may be secured to and removable from the shaft 2512 (e.g., by inserting a shank of the blade 2514, which may include a tenon, into a cavity of the shaft 2512).

Figure 16:
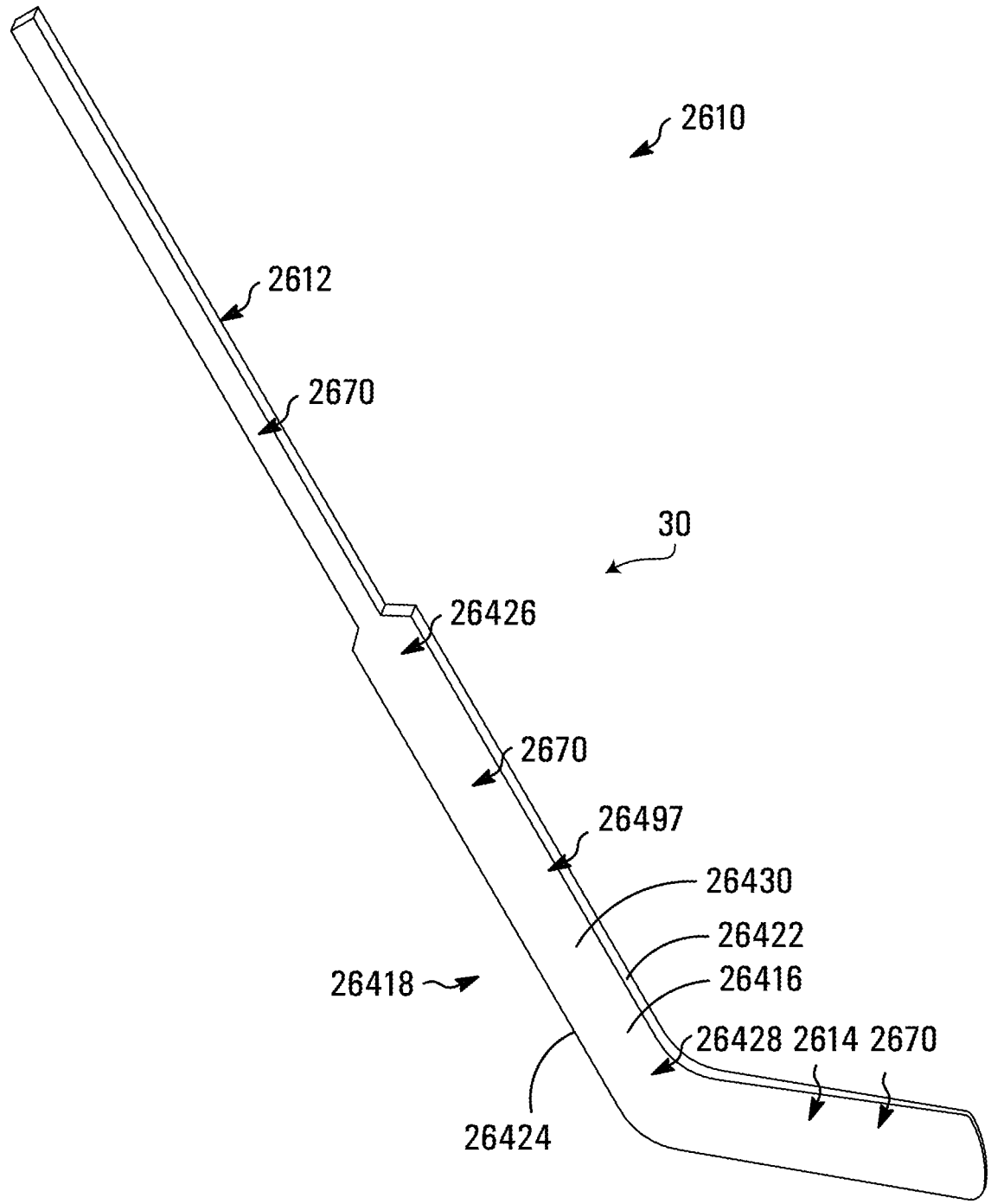
Figure 17A:
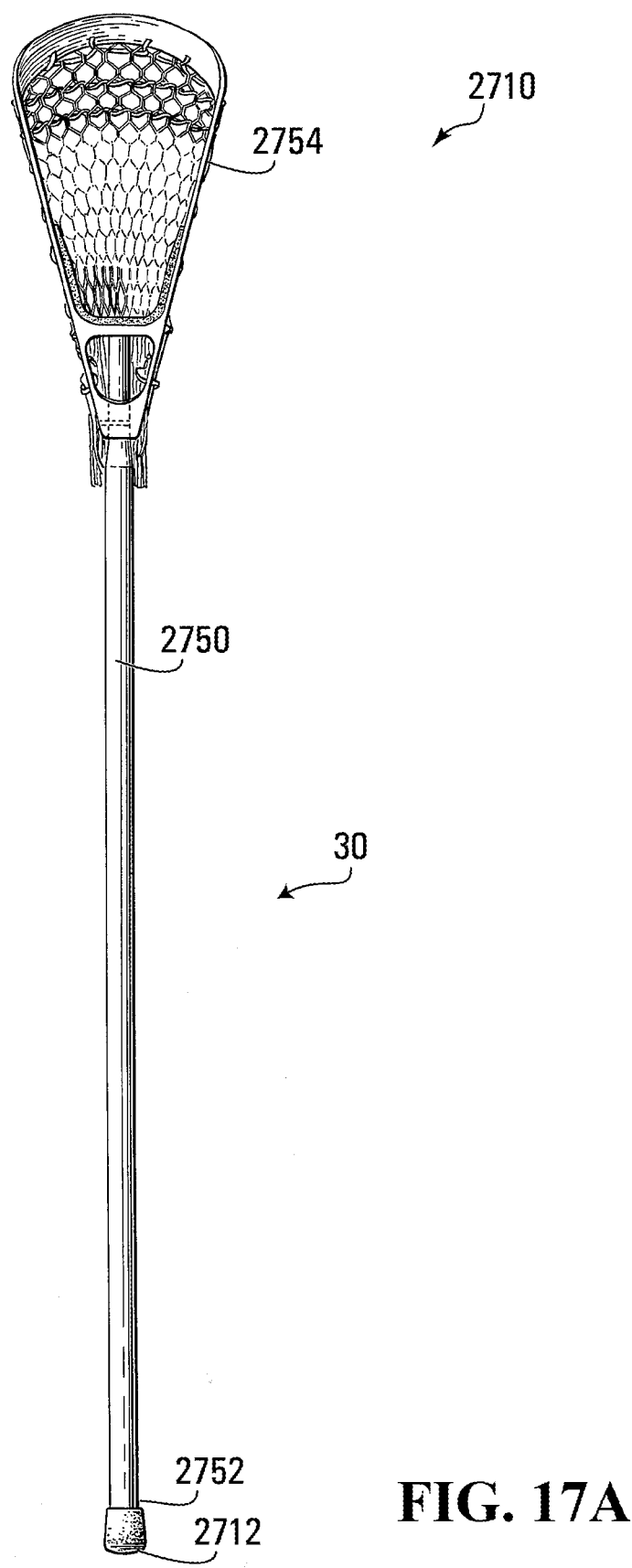
Figure 17B:
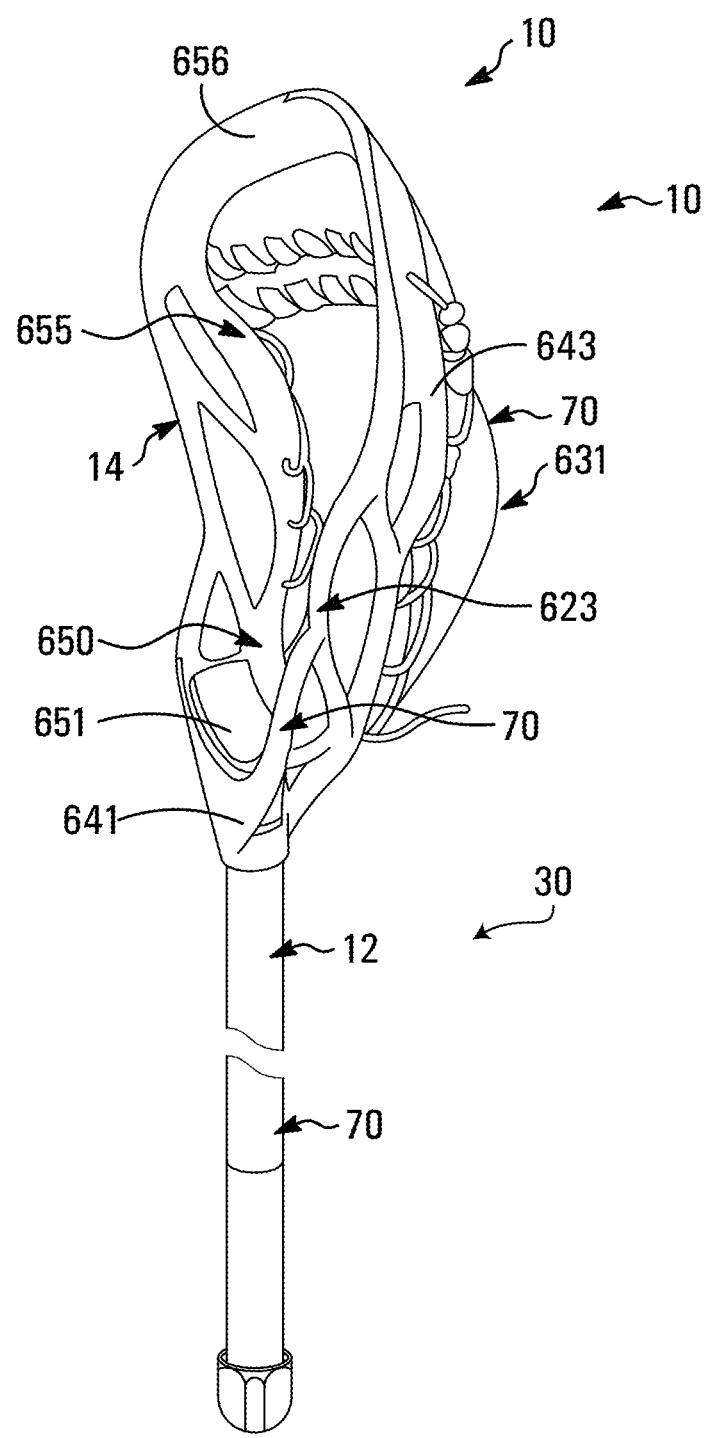

While in this embodiment the hockey stick 2510 is a player stick for the user that is a forward, i.e., right wing, left wing, or center, or a defenseman, in other embodiments, as shown in FIG. 16, the article may be a goalie stick 2610 where the user is a goalie. The goalie stick 2610 may be constructed according to principles discussed herein.

In this embodiment, the goalie stick 2610 comprises a paddle 26497 that may be constructed according to principles discussed herein. For instance, in some embodiments, the paddle 26497 may be disposed between the shaft 2612 and the blade 2614. The paddle 26497 is configured to block hockey pucks from flying into the net. A periphery 26430 of the paddle 26497 includes a front surface 26416 and a rear surface 26418 opposite one another, as well as a top edge 26422 and a bottom edge 26424 opposite one another. Proximal and distal end portions 26426, 26428 of the paddle 26497 are spaced apart in a longitudinal direction of the paddle 26497, respectively adjacent to the shaft 2612 and the blade 2614, and define a length of the paddle 26497.

Although in this embodiment the article is a sport implement that is a hockey stick, in other embodiments, the article may be any other implement used for striking, propelling or otherwise moving an object in a sport.

For example, in other embodiments, as shown in FIGS. 17A and 17B, the article may be a lacrosse stick 2710 for a lacrosse player, in which the object-contacting member 2714 of the lacrosse stick 2710 comprises a lacrosse head for carrying, shooting and passing a lacrosse ball.

The lacrosse head 2714 comprises a frame 2723 and a pocket 2731 connected to the frame 2723 and configured to hold the lacrosse ball. The frame 2723 includes a base 2741 connected to the shaft 2712 and a sidewall 2743 extending from the base 2741. In this embodiment, the sidewall 2743 is shaped to form a narrower area 2750 including a ball stop 2751 adjacent to the base 2741 and an enlarged area 2755 including a scoop 2756 opposite to the base 2741. Also, in this embodiment, the pocket 2731 includes a mesh 2760.

The stick 1210, 2510, 2610, 2710 including its components, may be implemented in any other suitable manner in other embodiments.

While the present description has been primarily focused on ice hockey, those skilled in the art would appreciate that certain of the teachings herein may be applicable to other sports, including but not limited to roller hockey, field hockey, soccer, American football, baseball, softball, tennis and lacrosse.

In some embodiments, any feature of any embodiment described herein may be used in combination with any feature of any other embodiment described herein.

Certain additional elements that may be needed for operation of certain embodiments have not been described or illustrated as they are assumed to be within the purview of those of ordinary skill in the art. Moreover, certain embodiments may be free of, may lack and/or may function without any element that is not specifically disclosed herein.

In describing the embodiments, specific terminology has been resorted to for the sake of description but this is not intended to be limited to the specific terms so selected, and it is understood that each specific term comprises all equivalents.

In case of any discrepancy, inconsistency, or other difference between terms used herein and terms used in any document incorporated by reference herein, meanings of the terms used herein are to prevail and be used.

Although various embodiments have been illustrated, this was purposes of describing, but should not be limiting. Various modifications will become apparent to those skilled in the art.

What is claimed is:

1. A non-transitory computer-readable storage medium storing computer-readable instructions which, when executed by a processor of a computing device, cause the computing device to carry out a method that comprises:
    obtaining sensor data indicative of a parameter sensed by a sensor associated with a hockey skate;
    obtaining position data indicative of a spatial position of the sensor or of the hockey skate;
    obtaining interaction data indicative of interactions between a wearer of the hockey skate and other players and/or a hockey puck;
    jointly processing the sensor data, the position data and the interaction data to derive a hybrid metric indicative of an aspect of performance involving the hockey skate;
    creating a digital message containing the hybrid metric; and
    sending the digital message over a data network to an address associated with a player.

2. The computer-readable storage medium defined in claim 1, further comprising determining an identity of the player by consulting a database based on sensor identification information carried in the sensor data.

3. The computer-readable storage medium defined in claim 1, wherein the hybrid metric comprises skating efficiency, wherein the hybrid metric is indicative of the wearer belonging to one of a plurality of efficiency categories.

4. The computer-readable storage medium defined in claim 3, wherein the plurality of efficiency categories includes a high efficiency skater and a low efficiency skater.

5. The computer-readable storage medium defined in claim 1, wherein the method further comprises time-aligning the sensor data and the position data to a common time reference, wherein the jointly processing is carried out on the time-aligned sensor data and position data.

6. The computer-readable storage medium defined in claim 5, wherein the jointly processing comprises determining a first contribution of the sensor data, determining a second contribution of the position data and weighting a combination of the first and second contributions by the interaction data to obtain the hybrid metric.

7. The computer-readable storage medium defined in claim 1, wherein the method further comprises determining an action from the sensor data and/or the position data, wherein the jointly processing is carried out as a function of the determined action.

8. The computer-readable storage medium defined in claim 7, wherein determining the action comprises detecting in the position data a movement pattern from a plurality of predetermined movement patterns.

9. The computer-readable storage medium defined in claim 1, wherein obtaining the position data comprises receiving images from a camera system and processing the images to track the position of the hockey skate in the images.

10. The computer-readable storage medium defined in claim 1, wherein obtaining the position data comprises receiving the position data from a fixed indoor localization system.

11. The computer-readable storage medium defined in claim 1, wherein obtaining the position data comprises:
   obtaining identification information together with the sensor data for a particular sensor, the identification information identifying the particular sensor; and
   deriving the position data based on correlating receipt of the identification information identifying the particular sensor at a plurality of receivers.

12. The computer-readable storage medium defined in claim 1, wherein the method further comprises:
   consulting a database based on an identity of the sensor to obtain an identity of the player; and
   storing the hybrid metric in memory in association with the player.

13. The computer-readable storage medium defined in claim 12, wherein the sensor data comprises data indicative of a heart rate of the player, and wherein the jointly processing comprises determining a displacement based on the position data and combining the displacement with the data indicative of the heart rate of the player.

14. The computer-readable storage medium defined in claim 13, wherein the method further comprises obtaining biometric information associated with the player, and normalizing the hybrid metric by the biometric information.

15. The computer-readable storage medium defined in claim 1, further comprising obtaining force or pressure applied to a first part of the hockey skate from the sensor data, obtaining changes in a position of a second part of the hockey skate from the position data, and wherein the hybrid metric is derived from at least the force or pressure applied to the first part of the hockey skate and the changes in the position of the second part of the hockey skate.

16. The computer-readable storage medium defined in claim 1, wherein the sensor data and the position data are collected over a time period, and wherein the interaction data is indicative of a number of interactions between the wearer of the hockey skate and the other players and/or the puck over the time period.

17. The computer-readable storage medium defined in claim 16, wherein the hybrid metric comprises skating efficiency, wherein the method further comprises determining the skating efficiency for a left skate and for a right skate worn simultaneously and computing an average skating efficiency therefrom.

18. The computer-readable storage medium defined in claim 17, wherein the hybrid metric comprises skating efficiency, wherein the skating efficiency of the player over the time period is computed based on a total impulse determined from the sensor data and divided by distance traveled during the time period.

19. The computer-readable storage medium defined in claim 18, wherein the method further comprises determining the total impulse by integration of net force from sensed data received from a pressure sensor or strain gage.

20. The computer-readable storage medium defined in claim 18, wherein the method further comprises normalizing the total impulse by a weight of the wearer.

21. The computer-readable storage medium defined in claim 17, wherein the skating efficiency is proportional to a duration of a glide phase in the time period.

22. The computer-readable storage medium defined in claim 1, wherein the jointly processing comprises determining an input energy be put into a shot, an output energy released by the shot and a shot efficiency based on the input energy and output energy.

23. The computer-readable storage medium defined in claim 22, wherein determining the shot efficiency includes computing a ratio of the output energy to the input energy.

24. The computer-readable storage medium defined in claim 1, wherein the sensor data is obtained from at least one of an accelerometer, a gyroscope, a magnetometer, an inertial measurement unit, a pressure sensor, a strain gauge, a body motion sensor, a heart rate monitor and a thermometer.

25. The computer-readable storage medium defined in claim 1, wherein the method further comprises:
   storing the hybrid metric in a computer-readable memory as a hybrid metric for the hockey skate;
   obtaining a plurality of hybrid metrics for a plurality of reference hockey skates;
   comparing the hybrid metric for the hockey skate with each of the plurality of obtained hybrid metrics for the plurality of reference hockey skates;
   selecting one of the plurality of reference hockey skates based on the comparing; and
   outputting a message conveying the selected reference hockey skate.

26. A non-transitory computer-readable storage medium storing computer-readable instructions which, when executed by a processor of a computing device, cause the computing device to carry out a method that comprises:
   obtaining sensor data indicative of a parameter sensed by a sensor associated with a hockey skate;
   obtaining position data indicative of a spatial position of the sensor or of the hockey skate;
   obtaining interaction data indicative of interactions between a wearer of the hockey skate and other players and/or a hockey puck;
   jointly processing the sensor data, the position data and the interaction data to derive a hybrid metric indicative of an aspect of performance involving the hockey skate; and
   outputting a signal conveying the hybrid metric on a network or storing the hybrid metric in a computer-readable memory;
   wherein the hybrid metric comprises skating efficiency; and the jointly processing comprises determining the skating efficiency for a left skate and for a right skate worn simultaneously and computing an average skating efficiency therefrom.

27. The computer-readable storage medium defined in claim 26, wherein obtaining the position data comprises receiving images from a camera system and processing the images to track the position of the hockey skate in the images.

28. The computer-readable storage medium defined in claim 26, wherein obtaining the position data comprises receiving the position data from a fixed indoor localization system.

29. The computer-readable storage medium defined in claim 26, wherein obtaining the position data comprises:
   obtaining identification information together with the sensor data for a particular sensor, the identification information identifying the particular sensor; and
   deriving the position data based on correlating receipt of the identification information identifying the particular sensor at a plurality of receivers.

30. The computer-readable storage medium defined in claim 26, further comprising obtaining force or pressure applied to a first part of the hockey skate from the sensor data, obtaining changes in a position of a second part of the hockey skate from the position data, and wherein the hybrid metric is derived from at least the force or pressure applied to the first part of the hockey skate and the changes in the position of the second part of the hockey skate.

31. The computer-readable storage medium defined in claim 26, wherein the sensor data and the position data are collected over a time period, and wherein the interaction data is indicative of a number of interactions between the wearer of the hockey skate and the other players and/or the puck over the time period.

32. The computer-readable storage medium defined in claim 26, wherein the skating efficiency is proportional to a duration of a glide phase in a time period when the sensor data and position data are collected.

33. The computer-readable storage medium defined in claim 26, wherein the sensor data comprises data indicative of a heart rate of a player, and wherein the jointly processing comprises determining a displacement based on the position data and combining the displacement with the data indicative of the heart rate of the player.

34. The computer-readable storage medium defined in claim 33, wherein the method further comprises obtaining biometric information associated with the player, and normalizing the hybrid metric by the biometric information.

35. The computer-readable storage medium defined in claim 26, wherein the jointly processing comprises determining an input energy be put into a shot, an output energy released by the shot and a shot efficiency based on the input energy and output energy.

36. The computer-readable storage medium defined in claim 35, wherein determining the shot efficiency includes computing a ratio of the output energy to the input energy.

37. The computer-readable storage medium defined in claim 26, wherein the method further comprises:
storing the hybrid metric in a computer-readable memory as a hybrid metric for the hockey skate;
obtaining a plurality of hybrid metrics for a plurality of reference hockey skates;
comparing the hybrid metric for the hockey skate with each of the plurality of obtained hybrid metrics for the plurality of reference hockey skates;
selecting one of the plurality of reference hockey skates based on the comparing; and
outputting a message conveying the selected reference hockey skate.

38. The computer-readable storage medium defined in claim 26, wherein the skating efficiency of a player over a time period when the sensor data and the position data is collected is computed based on a total impulse determined from the sensor data and divided by a distance traveled during the time period.

39. The computer-readable storage medium defined in claim 38, wherein the method further comprises determining the total impulse by integration of net force from sensed data received from a pressure sensor or strain gage.

40. The computer-readable storage medium defined in claim 38, wherein the method further comprises normalizing the total impulse by a weight of the wearer.

41. The computer-readable storage medium defined in claim 26, wherein the hybrid metric is indicative of the wearer belonging to one of a plurality of efficiency categories.

42. The computer-readable storage medium defined in claim 41, wherein the plurality of efficiency categories includes a high efficiency skater and a low efficiency skater.

43. A non-transitory computer-readable storage medium storing computer-readable instructions which, when executed by a processor of a computing device, cause the computing device to carry out a method that comprises:

obtaining sensor data indicative of a parameter sensed by a sensor associated with a hockey skate;
obtaining position data indicative of a spatial position of the sensor or of the hockey skate;
obtaining interaction data indicative of interactions between a wearer of the hockey skate and other players and/or a hockey puck;
jointly processing the sensor data, the position data and the interaction data to derive a hybrid metric indicative of an aspect of performance involving the hockey skate; and
outputting a signal conveying the hybrid metric on a network or storing the hybrid metric in a computer-readable memory
wherein the hybrid metric comprises a shot efficiency; and
the jointly processing comprises determining an input energy put into a shot, an output energy released by the shot and the shot efficiency based on the input energy and output energy.

44. The computer-readable storage medium defined in claim 43, wherein the jointly processing comprises determining a first contribution of the sensor data, determining a second contribution of the position data and weighting a combination of the first and second contributions by the interaction data to obtain the hybrid metric.

45. The computer-readable storage medium defined in claim 43, wherein obtaining the position data comprises:
obtaining identification information together with the sensor data for a particular sensor, the identification information identifying the particular sensor; and
deriving the position data based on correlating receipt of the identification information identifying the particular sensor at a plurality of receivers.

46. The computer-readable storage medium defined in claim 43, wherein the method further comprises:
consulting a database based on an identity of the sensor to obtain an identity of a player; and
storing the hybrid metric in memory in association with the player.

47. The computer-readable storage medium defined in claim 46, wherein the sensor data comprises biological data relating to the player.

48. The computer-readable storage medium defined in claim 43, further comprising obtaining force or pressure applied to a first part of the hockey skate from the sensor data, obtaining changes in a position of a second part of the hockey skate from the position data, and wherein the hybrid metric is derived from at least the force or pressure applied to the first part of the hockey skate and the changes in the position of the second part of the hockey skate.

49. The computer-readable storage medium defined in claim 43, wherein the hybrid metric further comprises skating efficiency, wherein the method further comprises determining the skating efficiency for a left skate and for a right skate worn simultaneously and computing an average skating efficiency therefrom.

50. The computer-readable storage medium defined in claim 49, wherein the skating efficiency is proportional to a duration of a glide phase in a time period when the sensor data and position data are collected.

51. The computer-readable storage medium defined in claim 43, wherein the sensor data comprises data indicative of a heart rate of a player, and wherein the jointly processing comprises determining a displacement based on the position data and combining the displacement with the data indicative of the heart rate of the player.

52. The computer-readable storage medium defined in claim 51, wherein the method further comprises obtaining biometric information associated with the player, and normalizing the hybrid metric by the biometric information.

53. The computer-readable storage medium defined in claim 43, wherein determining the shot efficiency includes computing a ratio of the output energy to the input energy.

54. The computer-readable storage medium defined in claim 43, wherein the method further comprises:
   storing the hybrid metric in a computer-readable memory as a hybrid metric for the hockey skate;
   obtaining a plurality of hybrid metrics for a plurality of reference hockey skates;
   comparing the hybrid metric for the hockey skate with each of the plurality of obtained hybrid metrics for the plurality of reference hockey skates;
   selecting one of the plurality of reference hockey skates based on the comparing; and
   outputting a message conveying the selected reference hockey skate.

55. The computer-readable storage medium defined in claim 43, wherein the hybrid metric further comprises a skating efficiency of a player over a time period when the sensor data and the position data is collected, wherein the jointly processing further comprises determining the skating efficiency by computing a total impulse determined from the sensor data and divided by a distance traveled during the time period.

56. The computer-readable storage medium defined in claim 55, wherein the method further comprises determining the total impulse by integration of net force from sensed data received from a pressure sensor or strain gage.

57. The computer-readable storage medium defined in claim 55, wherein the method further comprises normalizing the total impulse by a weight of the wearer.

58. The computer-readable storage medium defined in claim 43, wherein the hybrid metric is indicative of the wearer belonging to one of a plurality of efficiency categories.

59. The computer-readable storage medium defined in claim 58, wherein the plurality of efficiency categories includes a high efficiency skater and a low efficiency skater.

60. A system comprising:
   at least one sensor associated with a hockey skate, the at least one sensor outputting sensor data indicative of a parameter sensed by the at least one sensor;
   a positioning sub-system configured to obtain position data indicative of a spatial position of the at least one sensor or of the hockey skate;
   a computing device configured for:
      jointly processing the sensor data and the position data to derive a hybrid metric indicative of skating efficiency, based on the sensor data, the position data and interaction data indicative of on-ice interactions involving the hockey skate;
      creating a digital message containing the hybrid metric; and
      sending the digital message over a data network to an address associated with a player.

* * * * *